US008440705B2

(12) United States Patent
Lindquist et al.

(10) Patent No.: US 8,440,705 B2
(45) Date of Patent: May 14, 2013

(54) COMPOUNDS, COMPOSITIONS AND METHODS OF INHIBITING ALPHA-SYNUCLEIN TOXICITY

(75) Inventors: Susan L. Lindquist, Chestnut Hill, MA (US); Tiago Outeiro, Cambridge, MA (US); Richard Labaudinière, Sherborn, MA (US)

(73) Assignees: Whitehead Institute for Biomedical Research, Cambridge, MA (US); FoldRx Pharmaceuticals, Inc., Cambridge, MA (US)

( * ) Notice: Subject to any disclaimer, the term of this patent is extended or adjusted under 35 U.S.C. 154(b) by 1284 days.

(21) Appl. No.: 11/575,481

(22) PCT Filed: Sep. 16, 2005

(86) PCT No.: PCT/US2005/033050
§ 371 (c)(1), (2), (4) Date: Jan. 11, 2008

(87) PCT Pub. No.: WO2006/034003
PCT Pub. Date: Mar. 30, 2006

(65) Prior Publication Data
US 2008/0261953 A1 Oct. 23, 2008

Related U.S. Application Data

(60) Provisional application No. 60/610,796, filed on Sep. 17, 2004.

(51) Int. Cl.
*C07D 277/82* (2006.01)
*A61K 31/428* (2006.01)

(52) U.S. Cl.
USPC .......................................... 514/367; 548/161

(58) Field of Classification Search .................... None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,761,490 A | 9/1973 | Schafer et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 4,710,384 A | 12/1987 | Rotman |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,106,851 A | 4/1992 | Turconi et al. |
| 5,120,548 A | 6/1992 | McClelland et al. |
| 5,308,857 A | 5/1994 | Takasugi et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,709,874 A | 1/1998 | Hanson et al. |
| 5,733,566 A | 3/1998 | Lewis |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,968,952 A | 10/1999 | Venet et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |

(Continued)

FOREIGN PATENT DOCUMENTS

DE 2 418 913 10/1975
EP 0417751 9/1991

(Continued)

OTHER PUBLICATIONS

Derwent Abstract of JP 48-76867, Oct. 16, 1973, Derwent ACC No. 1974-04822V.*
Broe et al., "Anti-Inflammatory Drugs Protect Against Alzheimer Disease at Low Doses", Archives of Neurology, 57, 1586-1591, Nov. 2000.*
Pendick, D., "Alzheimer's Medications: Dosing Side Effects and Drug Interactions", Memory Loss and the Brain, http://memoryloss-online.com/summer2002.alzdrugs.htm, 2002.*
Gasparini, L. et al., "Non-Steroidal Anti-Inflammatory Drugs (NSAIDs) in Alzheimer's Disease: Old and New Mechanisms of Action", Journal of Neurochemistry, 91, 521-536, Nov. 2004.*
Fleming, James et al., "Detection of Compounds That Rescue Rab1-Synuclein Toxicity", Methods in Enzymology, 2008, 439 (Small GTPAses in Disease, Part B), 339-351.*
Kakimura et al., "Release and aggregation of cytochrome c and α-synuclein are inhibited by the antiparkinsonian drugs, talipexole and pramipexole," Eur J Pharmacol, 2001, 417:59-67.

(Continued)

*Primary Examiner* — Michael Barker
(74) *Attorney, Agent, or Firm* — Fish & Richardson P.C.

(57) ABSTRACT

Compounds and compositions are provided for treatment or amelioration of one or more symptoms of α-synuclein toxicity, α-synuclein mediated diseases or diseases in which α-synuclein fibrils are a symptom or cause of the disease. In one embodiment, the compounds for use in the compositions and methods are heteroaryl acylguanidines, heteroarylhydrazones, dihydropyridones, heteroaryl and aryl styryl ketones, and heteroarylpyrazoles.

18 Claims, 34 Drawing Sheets

U.S. PATENT DOCUMENTS

| | | | |
|---|---|---|---|
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,506,782 | B1 | 1/2003 | Thorsett et al. |
| 6,569,851 | B1 | 5/2003 | Thompson et al. |
| 2003/0073610 | A1 | 4/2003 | Lindquist et al. |
| 2004/0067991 | A1 | 4/2004 | Greig et al. |
| 2005/0064548 | A1 | 3/2005 | Lindquist et al. |
| 2010/0004277 | A1* | 1/2010 | Bulawa et al. ............ 514/284 |

FOREIGN PATENT DOCUMENTS

| | | |
|---|---|---|
| GB | 158076 A | 12/1980 |
| JP | 48-76867 * | 10/1973 |
| WO | WO 98/28268 | 7/1998 |
| WO | WO 98/38177 | 9/1998 |
| WO | WO0026203 A1 | 5/2000 |
| WO | 01/94340 | 12/2001 |
| WO | 03/059346 | 7/2003 |
| WO | WO03072554 A1 | 9/2003 |
| WO | WO03101927 A1 | 12/2003 |
| WO | 2005/030128 | 1/2005 |

OTHER PUBLICATIONS

Srivastava, "Some mono- or disubstituted benzothiazolylguanidines as tuberculostatic, antibacterial, and antifungal agents," Allgemeine und Praktische Chemie, 1969, 20(2):35-36 (Abstract only).

Database Accession No. RN 695212-02-3 dated Jun. 18, 2004 (Abstract only).

Supplementary European Search Report in EP 05 81 3951 mailed Nov. 18, 2009, 11 pages.

Arai et al., "Argyrophilic glial inclusions in the midbrain of patients with Parkinson's disease and diffuse Lewy body disease are immunopositive for NACP/alpha-synuclein," Neurosci. Lett., 1999, 259:83-86.

Auluck et al., "Chaperone suppression of alpha-synuclein toxicity in a Drosophila model for Parkinson's disease," Science, 2002, 295(5556):865-868.

Chartier-Harlin et al., "Alpha-synuclein locus duplication as a cause of familial Parkinson's disease," Lancet, 2004, 364:1167-1169.

Conway et al., "Accelerated in vitro fibril formation by a mutant alpha-synuclein linked to early-onset Parkinson disease," Nature Med., 1998, 4:1318-1320.

Hashimoto et al., "Transgenic models of alpha-synuclein pathology: past, present, and future," Ann. NY Acad. Sci., 2003, 991:171-188.

Hashimoto et al., "Human recombinant NACP/alpha-synuclein is aggregated and fibrillated in vitro: relevance for Lewy body disease," Brain Res., 1998, 799:301-306.

Ibanez et al., "Causal relation between alpha-synuclein gene duplication and familial Parkinson's disease," Lancet, 2004, 364:1169-1171.

Klucken et al., "Hsp70 Reduces alpha-Synuclein Aggregation and Toxicity," J. Biol. Chem., 2004, 279(24):25497-25502.

Kruger et al., "Ala30Pro mutation in the gene encoding alpha-synuclein in Parkinson's disease," Nature Genet., 1998, 18(2):106-108.

Lee et al., "Human alpha-synuclein-harboring familial Parkinson's disease-linked Ala-53→Thr mutation causes neurodegenerative disease with alpha-synuclein aggregation in transgenic mice," Proc. Natl. Acad. Sci. USA, 2002, 99(13):8968-8973.

Lewy, "Paralysis agitans," Handbuch der Neurologie, 1912, Lewandowski (ed.), Springer, Berlin, pp. 920-933 (including English translation).

Lo Bianco et al., "α-Synucleinopathy and selective dopaminergic neuron loss in a rat lentiviral-based model of Parkinson's disease," Proc. Natl. Acad. Sci. USA, 2002, 99(16):10813-10818.

Marín et al., "Promoter-specific inhibition of transcription by daunorubicin in Saccharomyces cerevisiae," Biochem. J., 2002, 368:131-136.

Masliah et al., "Dopaminergic loss and inclusion body formation in alpha-synuclein mice: implications for neurodegenerative disorders," Science, 2000, 287(5456):1265-1269.

Miller et al., "Alpha-synuclein in blood and brain from familial Parkinson disease with SNCA locus triplication," Neurology, 2004, 62:1835-1838.

Murray et al., "Synucleinopathies: a pathological and molecular review," Clinical Neurosc. Res., 2001, 1:445-455.

Narhi et al., "Both familial Parkinson's disease mutations accelerate alpha-synuclein aggregation," J. Biol. Chem., 1999, 274:9843-9846.

Nogrady, Medicinal Chemistry A Biochemical Approach, 1985, Oxford University Press, New York, pp. 388-392.

Oluwatosin-Chigbu et al., "Parkin suppresses wild-type alpha-synuclein-induced toxicity in SHSY-5Y cells," Biochem. Biophys. Res. Commun., 2003, 309(3):679-684.

Outeiro et al., "Yeast cells provide insight into alpha-synuclein biology and pathobiology," Science, 2003, 302(5651):1772-1775.

Pollanen et al., "Pathology and biology of the Lewy body," J. Neuropath. Exp. Neurol., 1993, 52:183-191.

Polymeropoulos et al., "Mutation in the alpha-synuclein gene identified in families with Parkinson's disease," Science, 1997, 276(5321):2045-2047.

Singleton et al., "α-Synuclein Locus Triplication Causes Parkinson's Disease," Science, 2003, 302(5646):841.

Spillantini et al., "Alpha-Synuclein in filamentous inclusions of Lewy bodies from Parkinson's disease and dementia with lewy bodies," Proc. Natl. Acad. Sci. USA, 1998, 95:6469-6473.

Trojanowski and Lee, "Parkinson's disease and related synucleinopathies are a new class of nervous system amyloidoses," Neurotoxicology, 2002, 23:457-460.

Ueda et al., "Molecular cloning of cDNA encoding an unrecognized component of amyloid in Alzheimer disease," Proc. Natl. Acad. Sci. USA, 1993, 90:11282-11286.

Wood et al., "Alpha-synuclein fibrillogenesis is nucleation-dependent. Implications for the pathogenesis of Parkinson's disease," J. Biol. Chem., 1999, 274:19509-19512.

Zarranz et al., "The new mutation, E46K, of alpha-synuclein causes Parkinson and Lewy body dementia," Ann. Neurol., 2004, 55:164-173.

Authorized Officer Dwayne C. Jones, International Search Report and Written Opinion for corresponding PCT Application No. PCT/US05/33050, mailed May 30, 2006, 10 pages.

Authorized Officer Phyllis G. Spivack, International Preliminary Report on Patentability for corresponding PCT Application No. PCT/US05/33050, mailed Jan. 17, 2007, 5 pages.

Shikhaliev et al., "Condensation of Isatoic Anhydride with Hetarylguanidines", Russian Journal of General Chemistry, 2003, 73(7), pp. 1147-1150.

O'zbekiston Kimyo Jumali, 2002, vol. 4, pp. 39-41 (abstract only).

Peishan et al., "Solid-phase synthesis of N-acyl-N-carbamoylguanidines", Tetrahedron Letters, 1998, 39(52), pp. 9789-9792.

R. Evers, "Struktur und Reaktionsyerhalten aktivierter C=N-Doppelbindungen: Synthese heterocyclisch substituierter Guanidinderivate," Z. Chem., 29(12): 448-449 (1989) (with English translation).

Furukawa et al., "Reaction of Biguanides and Related Compounds. XV.1) Cyclizations of Arylbiguanides and 2-Guanidino benzimidazole with Bifunctional Unsatureated Dicarboxylates to s-Triazines and Imidazolines", Chemical & Pharmaceutical Bulletin, 1983, 31 (7), pp. 2473-2479.

Martin, Journal filer Praktische Chemie, 1981, 323(2), pp. 303-310 (with English translation).

Capuano et al., Chemische Berichte, 1974,107(1), pp. 62-67 (with English abstract only).

Database Accession No. 1160 dated 1979, XP-002669290 (With abstract).

* cited by examiner

COMPOUNDS, COMPOSITIONS AND METHODS OF INHIBITING ALPHA-SYNUCLEIN TOXICITY

CROSS-REFERENCE TO RELATED APPLICATIONS

This Application is a national phase filing under 35 U.S.C. §371 of international application number PCT/US2005/033050, filed Sep. 16, 2005, which claims priority from U.S. Provisional Application No. 60/610,796, filed Sep. 17, 2004. The entire content of the prior applications are incorporated herein by reference in their entirety.

STATEMENT AS TO FEDERALLY SPONSORED RESEARCH

Funds used to support some of the studies disclosed herein were provided by grant number NIH NS 44829 awarded by the National Institutes of Health. The Government may have certain rights in the invention.

FIELD

The subject matter provided herein relates to compounds, composition and methods of inhibiting α-synuclein toxicity. In one embodiment, the compounds are benzothiazolyl, benzoxazolyl and benzimidazolyl guanidines, benzimidazolyl hydrazones, benzodihydropyridones, dihydropyridones, thienyl styryl ketones and N-benzimidazolyl-aminopyrazoles. In another embodiment, the compounds are used in methods of treatment of α-synuclein fibril mediated diseases, such as Parkinson's disease.

BACKGROUND

Parkinson's disease is a neurodegenerative disorder that is pathologically characterized by the presence of intracytoplasmic Lewy bodies (Lewy in *Handbuch der Neurologie*, M. Lewandowsld, ed., Springer, Berlin, pp. 920-933, 1912; Pollanen et al., *J. Neuropath. Exp. Neurol.* 52:183-191, 1993), the major components of which are filaments consisting of α-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in α-synuclein causing familial early onset Parlinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998; Zarranz et al., *Ann. Neurol.* 55:164-173, 2004). Triplication and duplication mutation of the α-synuclein gene have been linked to early-onset of Parkinson's disease (Singleton et al., Science 302:841, 2003; Chartier-Harlin at al. *Lancet* 364:1167-1169, 2004; Ibanez et al., *Lancet* 364:1169-1171, 2004). In vitro studies have demonstrated that recombinant α-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999). Both Parkinson's disease-linked α-synuclein mutations accelerate this aggregation process, demonstrating that such in vitro studies may have relevance for Parkinson's disease pathogenesis. Alpha-synuclein aggregation and fibril formation fulfills of the criteria of a nucleation-dependent polymerization process (Wood et al., *J. Biol. Chem.* 274:19509-19512, 1999). In this regard α-synuclein fibril formation resembles that of Alzheimer's β-amyloid protein (Aβ) fibrils. Alpha-synuclein recombinant protein, and non-Aβ component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of α-, β-, and γ-synucleins, of which only α-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, alpha-synuclein) in the etiology of a number of neurodegenerative and/or amyloid diseases has developed from several observations. Pathologically, α-synuclein was identified as a major component of Lewy bodies, the hallmark inclusions of Parkinson's disease, and a fragment thereof was isolated from amyloid plaques of a different neurological disease, Alzheimer's disease. Biochemically, recombinant α-synuclein was shown to form amyloid-like fibrils that recapitulated the ultrastructural features of alpha-synuclein isolated from patients with dementia with Lewy bodies, Parlinson's disease and multiple system atrophy. Additionally, the identification of mutations within the α-synuclein gene, albeit in rare cases of familial Parkinson's disease, demonstrated an unequivocal link between synuclein pathology and neurodegenerative diseases. The common involvement of α-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies."

Fibrillization and aggregation of α-synuclein is thought to play major role in neuronal dysfunction and death of dopaminergic neurons in PD. Mutations in α-synuclein or genomic triplication of wild type α-synuclein (leading to its overexpression) cause certain rare familial forms of Parkinson's disease. In vitro and in vivo models suggest that over-expression of wild-type α-synuclein induces neuronal cell death. See, e.g., Polymeropoulos, et al. (1997) *Science* 276(5321): 2045-7, Kruger, et al. (1998) *Nat. Genet.* 18(2):106-8, Singleton, et al. (2003) *Science* 302(5646):841, Miller, et al. (2004) *Neurology* 62(10):1835-8, Hashimoto, et al. (2003) *Ann NY Acad Sci.* 991:171-88, Lo Bianco, et al. (2002) *Proc Natl Acad Sci USA.* 99(16):10813-8, Lee, et al. (2002) *Proc Natl Acad Sci USA.* 99(13):8968-73, Masliah, et al. (2000) *Science* 287(5456):1265-9, Auluck, et al. (2002) *Science* 295(5556): 865-8, Oluwatosin-Chigbu et al. (2003) *Biochem Biophys Res Commun* 309(3): 679-84, Klucken et al. (2004) *J Biol. Chem.* 279(24):25497-502. Protecting neurons from the toxic effects of α-synuclein is a promising strategy for treating Parkinson's disease and other synucleinopathies such as Lewy body dementia.

Thus, there is a need for compounds and compositions that prevent α-synuclein toxicity and/or aggregation and/or promote α-synuclein fibril disaggregation. Such compounds and composition are useful in treating or ameliorating one or more symptoms of α-synuclein mediated diseases and disorders, or diseases and disorders in which a-synuclein fibril formation is implicated, including but not limited to, Parkinson's disease, dementia with Lewy bodies, multiple system atrophy and the Lewy body variant of Alzheimer's disease.

SUMMARY

Provided herein are compounds, compositions containing the compounds, and methods of use of the compounds as α-synuclein inhibitors. Also provided are methods of treatment or amelioration of one or more symptoms of diseases and disorders associated with α-synuclein toxicity. Also provided are methods of treatment or amelioration of one or more symptoms of diseases and disorders associated with α-synuclein fibril formation. Such diseases and disorders include, but are not limited to, Parkinson's disease and Lewy body dementia. Other diseases and disorders include tauopathies, such as, but not limited to, Alzheimer's disease.

Use of any of the described compounds for the treatment or amelioration of one or more symptoms of diseases and disorders associated with α-synuclein toxicity or α-synuclein fibril formation is also contemplated. Furthermore, use of any of the described compounds for the manufacture of a medicament for the treatment of diseases and disorders associated with α-synuclein toxicity or α-synuclein fibril formation is also contemplated.

In one embodiment, the compounds for use in the compositions and methods provided herein have Formula I:

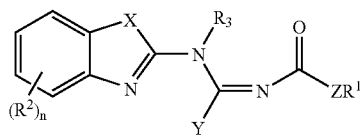

where X is O, S or NR, where R is hydrogen, alkyl, alkenyl, alkynyl, cycloalkyl, heterocyclyl, aryl, heteroaryl or aralkyl;

Y is NRR' or OH; where R' is hydrogen, alkyl, alkenyl, alkynyl, cycloalkyl, heterocyclyl, aryl, heteroaryl or aralkyl;

Z is a direct bond or NR;

$R^1$ is hydrogen, alkyl, alkenyl, alkynyl, cycloalkyl, heterocyclyl, aryl, heteroaryl, aralkyl, aralkenyl, heteroaralkyl or heteroaralkenyl;

n is 0 to 4;

$R^2$ is selected from (i) or (ii) as follows:
(i) hydrogen, alkyl, alkenyl, alkynyl, aryl, heteroaryl, heteroarylium, cycloalkyl, heterocyclyl, $C(A)R^{110}$, halo, pseudohalo, $OR^{111}$, $S(D)_aR^{112}$, $NR^{115}R^{116}$ or $N^+R^{115}R^{116}R^{117}$; or
(ii) any two $R^2$ groups, which substitute adjacent atoms on the ring, together form alkylene, alkenylene, alkynylene or heteroalkylene;

A is O, S or $NR^{125}$;

$R^{110}$ is hydrogen, alkyl, alkenyl, alkynyl, aryl, heteroaryl, heteroarylium, cycloalkyl, heterocyclyl, $C(A)R^{126}$, halo pseudohalo, $OR^{125}$, $SR^{125}$, $NR^{127}R^{128}$ and $SiR^{122}R^{123}R^{124}$;

$R^{111}$ is hydrogen, alkyl, alkenyl, alkynyl, aryl, heteroaryl, heteroarylium, cycloalkyl, heterocyclyl, $C(A)R^{129}$, $NR^{130}R^{131}$ and $SiR^{122}R^{123}R^{124}$;

D is O or $NR^{125}$;

a is 0, 1 or 2;

when a is 1 or 2, $R^{112}$ is selected from hydrogen, alkyl, alkenyl, alkynyl, aryl, heteroaryl, heteroarylium, cycloalkyl, heterocyclyl, halo, pseudohalo, $OR^{125}$, $SR^{125}$ and $NR^{132}R^{133}$;

when a is 0, $R^{112}$ is selected from hydrogen, alkyl, alkenyl, alkynyl, aryl, heteroaryl, heteroarylium, cycloalkyl, heterocyclyl, $SR^{125}$ and $C(A)R^{129}$;

$R^{115}$, $R^{116}$ and $R^{117}$ are each independently selected from (a) and (b) as follows:

(a) hydrogen, alkyl, alkenyl, alkynyl, aryl, heteroaryl, heteroarylium, cycloalkyl, heterocyclyl, $C(A)R^{129}$, $OR^{125}$ or $NR^{132}R^{133}$; or
(b) any two of $R^{115}$, $R^{116}$ and $R^{117}$ together form alkylene, alkenylene, alkynylene, heteroalkylene, and the other is selected as in (a);

$R^{122}$, $R^{123}$ and $R^{124}$ are selected as in (i) or (ii) as follows:
(i) $R^{122}$, $R^{123}$ and $R^{124}$ are each independently hydrogen, alkyl, alkenyl, alkynyl, aryl, heteroaryl, heteroarylium, cycloalkyl, heterocyclyl, $OR^{125}$ or $N^{132}R^{133}$; or
(ii) any two of $R^{122}$, $R^{123}$ and $R^{124}$ together form alkylene, alkenylene, alkynylene, heteroalkylene; and the other is selected as in (i);

$R^{125}$ is hydrogen, alkyl, alkenyl, alkynyl, aryl, heteroaryl, heteroarylium, cycloalkyl or heterocyclyl;

$R^{126}$ is hydrogen, alkyl, alkenyl, alkynyl, aryl, heteroaryl, heteroarylium, cycloalkyl, heterocyclyl, $OR^{125}$ or $N^{134}R^{135}$; where $R^{134}$ and $R^{135}$ are each independently hydrogen, alkyl, alkenyl, alkynyl, aryl, heteroaryl, heteroarylium, cycloalkyl, heterocyclyl, $OR^{136}$ or $NR^{132}R^{133}$, or $R^{134}$ and $R^{135}$ together form alkylene, alkenylene, alkynylene, heteroalkylene, where $R^{136}$ is hydrogen, alkyl, alkenyl, alkynyl, aryl, heteroaryl, heteroarylium, cycloalkyl or heterocyclyl;

$R^{127}$ and $R^{128}$ are selected as in (i) or (ii) as follows:
(i) $R^{127}$ and $R^{128}$ are each independently hydrogen, alkyl, alkenyl, alkynyl, aryl, heteroaryl, heteroarylium, cycloalkyl, heterocyclyl, $OR^{125}$, $NR^{137}R^{138}$ or $C(A)R^{39}$, where $R^{137}$ and $R^{138}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and $R^{139}$ is hydrogen, alkyl, alkenyl, alkynyl, aryl, heteroaryl, heteroarylium, cycloalkyl, heterocyclyl, $OR^{140}$ or $NR^{132}R^{133}$, where $R^{140}$ is alkyl, alkenyl, alkynyl, aryl, heteroaryl, heteroarylium, cycloalkyl, heterocyclyl; or
(ii) $R^{127}$ and $R^{128}$ together form alkylene, alkenylene, alkynylene, heteroalkylene;

$R^{129}$ is hydrogen, alkyl, alkenyl, alkynyl, aryl, heteroaryl, heteroarylium, cycloalkyl, heterocyclyl, $OR^{140}$ or $NR^{132}R^{133}$;

$R^{130}$ and $R^{131}$ are each independently hydrogen, alkyl, alkenyl, alkynyl, aryl, heteroaryl, heteroarylium, cycloalkyl, heterocyclyl or $C(A)R^{141}$, where $R^{141}$ is alkyl, alkenyl, alkynyl, aryl, heteroaryl, heteroarylium, cycloalkyl, heterocyclyl, $OR^{125}$ or $NR^{132}R^{133}$; or $R^{130}$ and $R^{131}$ together form alkylene, alkenylene, alkynylene, heteroalkylene;

$R^{132}$ and $R^{133}$ are each independently hydrogen, alkyl, alkenyl, alkynyl, aryl, heteroaryl, heteroarylium, cycloalkyl, heterocyclyl, or $R^{132}$ and $R^{133}$ together form alkylene, alkenylene, alkynylene, heteroalkylene; and $R^3$ is hydrogen, alkyl, alkenyl, alkynyl, cycloalkyl, heterocyclyl, aryl or heteroaryl;

wherein X, Y, Z, $R^1$, $R^2$ and $R^3$ are each independently unsubstituted or substituted with one or more substituents, in one embodiment one, two or three substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, hydroxycarbonylalkenyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, alkoxyxarbonylalkoxy, aryloxycarbonyl, aryloxycarbonylalkyl, aralkoxycarbonyl, aralkoxycarbonylalkyl, aralkoxycarbonylalkoxy, arylcarbonylalkyl, aminocarbonyl, aminocarbonylalkyl, aminocarbonylalkoxy, alkylaminocarbonyl, alkylaminocarbonylalkyl, alkylaminocarbonylalkoxy, dialkylaminocarbonyl, dialkylaminocarbonylalkyl, dialkylaminocarbonylalkoxy, arylaminocarbonyl, arylaminocarbonylalkyl, arylaminocarbonylalokoxy, diarylaminocarbonyl, diarylaminocarbonylalkyl, diarylaminocarbonyl alkoxy, arylalkylaminocarbonyl, arylalkylaminocarbonylalkyl, arylalkylaminocarbonylalkoxy, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-diarylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N⁺R¹⁵¹R¹⁵²R¹⁵³, P(R¹⁵⁰)₂, P(=O)(R¹⁵⁰)₂, OP(=O)(R¹⁵⁰)₂, —NR¹⁶⁰C(=O)R¹⁶³, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; azido, tetrazolyl or two $Q^1$ groups, which substitute atoms in a 1,2 or 1,3 arrangement, together form alkylenedioxy (i.e., —O—(CH₂)ᵧ—O—), thioalkylenoxy (i.e., —S—(CH₂)ᵧ—O—) or alkylenedithioxy (i.e., —S—(CH₂)ᵧ—S—) where y is 1 or 2; or two $Q^1$ groups, which substitute the same atom, together form alkylene; and each $Q^1$ is independently unsubstituted or substituted with one or more substituents, in one embodiment one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, hydroxycarbonylalkenyl alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N', N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N⁺R¹⁵¹R¹⁵²R¹⁵³, P(R¹⁵⁰)₂, P(=O)(R¹⁵⁰)₂, OP(=O)(R¹⁵⁰)₂, —NR¹⁶⁰C(=O)R¹⁶³, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., —O—(CH₂)ᵧ—O—), thioalkylenoxy (i.e., —S—(CH₂)ᵧ—O—) or alkylenedithioxy (i.e., —S—(CH₂)ᵧ—S—) where y is 1 or 2; or two $Q^2$ groups, which substitute the same atom, together form alkylene;

$R^{150}$ is hydroxy, alkoxy, aralkoxy, alkyl, heteroaryl, heterocyclyl, aryl or —NR¹⁷⁰R¹⁷¹, where $R^{170}$ and $R^{171}$ are each independently hydrogen, alkyl, aralkyl, aryl, heteroaryl, heteroaralkyl or heterocyclyl, or $R^{170}$ and $R^{171}$ together form alkylene, azaalkylene, oxaalkylene or thiaalkylene;

$R^{151}$, $R^{152}$ and $R^{153}$ are each independently hydrogen, alkyl, aryl, aralkyl, heteroaryl, heteroaralkyl, heterocyclyl or heterocyclylalkyl;

$R^{160}$ is hydrogen, alkyl, aryl, aralkyl, heteroaryl, heteroaralkyl, heterocyclyl or heterocyclylalkyl; and $R^{163}$ is alkoxy, aralkoxy, alkyl, heteroaryl, heterocyclyl, aryl or —NR¹⁷⁰R¹⁷¹.

In one embodiment, $R^1$ is substituted with one or more substituents independently selected from aryloxy, aryl, heteroaryl, halo, pseudohalo, alkyl, alkoxy, cycloalkyl, alkoxycarbonyl, hydroxycarbonyl, alkylamino, and dialkylamino.

As one of skill in the art will recognize, Formula I structurally sets forth one tautomeric form of the compounds encompassed therein; all such tautomeric forms are contemplated herein.

In another embodiment, the compounds for use in the compositions and methods provided herein have Formula II:

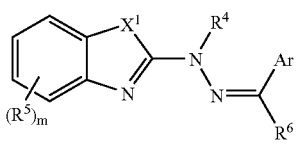

where $X^1$ is O, S and NR;
Ar is aryl or heteroaryl;
$R^4$ is hydrogen, alkyl, alkenyl, alkynyl, cycloalkyl, heterocyclyl, aryl or heteroaryl;
$R^5$ is selected as for $R^2$;
m is 0 to 4; and
$R^6$ is hydrogen, alkyl, alkenyl, alkynyl, cycloalkyl, heterocyclyl, aryl or heteroaryl;
where $X^1$, Ar, $R^4$, $R^5$ and $R^6$ are each independently unsubstituted or substituted with one or more, in one embodiment one, two or three substituents, each independently selected from $Q^1$.

In another embodiment, the compounds for use in the compositions and methods provided herein have Formula III:

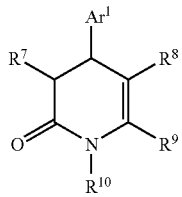

where $Ar^1$ is aryl, heteroaryl, or cycloalkyl;
$R^7$ is hydrogen, alkyl, alkenyl, alkynyl, cycloalkyl, heterocyclyl, aryl, heteroaryl or NRR, where R is hydrogen or alkyl;
$R^8$ and $R^9$ are each independently selected as for $R^2$; and
$R^{10}$ is hydrogen, alkyl, alkenyl, alkynyl, cycloalkyl, heterocyclyl, aryl or heteroaryl;
where $Ar^1$, $R^7$, $R^8$, $R^9$ and $R^{10}$ are each independently unsubstituted or substituted with one or more, in one embodiment one, two or three substituents, each independently selected from $Q^1$.

In some embodiments, $Ar^1$ is aryl, heteroaryl or cycloalkyl, and is unsubstituted or substituted with alkyl, alkenyl, alkynyl, aryl, heteroaryl, halo, pseudohalo, dialkylamino, aryloxy, aralkoxy, haloalkyl, alkoxy, haloalkoxy, cycloalkyl, heteroaryl, or COOR, where R is hydrogen or alkyl.

In some embodiments, $R^8$ and $R^9$ are each independently selected from (i) and (ii) as follows:
(i) $R^8$ and $R^9$ together with the atoms to which they are attached form a fused phenyl ring; and
(ii) $R^8$ is CN or $COOR^{200}$, where $R^{200}$ is hydrogen, alkyl, alkenyl, alkynyl, cycloalkyl, heterocyclyl, aryl or heteroaryl; and $R^9$ is hydrogen, alkyl or alkylthio; and
$R^{10}$ is hydrogen.

In one embodiment of (i) above, $R^8$ and $R^9$ together with the atoms to which they are attached form a fused phenyl ring, which is unsubstituted or substituted with halo, pseudohalo, alkyl, alkoxy, cycloalkyl, fused cycloalkyl, fused heterocyclyl, fused heteroaryl, aryl (e.g., phenyl), and fused aryl (e.g., fused phenyl ring), which is unsubstituted or substituted with halo, pseudohalo, alkyl, alkoxy, aryl, cycloalkyl, heterocyclyl, fused aryl, fused heteroaryl, and fused cycloalkyl.

In another embodiment, $Ar^1$ is phenyl, naphthyl, pyridyl, furyl, or thienyl, and is unsubstituted or substituted with alkyl, alkenyl, halo, pseudohalo, dialkylamino, aryloxy, haloalkyl, alkoxy, aryloxy, cycloalkyl, heterocyclyl, fused heterocyclyl, aryl, fused aryl, heteroaryl, fused heteroaryl, or COOR, where R is hydrogen or alkyl.

In another embodiment, the compounds for use in the compositions and methods provided herein have Formula IV:

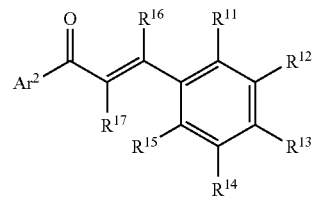

where $Ar^2$ is aryl or heteroaryl; and
$R^{11}$, $R^{12}$, $R^{13}$, $R^{14}$, $R^{15}$, $R^{16}$ and $R^{17}$ are each independently selected as for $R^2$;
where $Ar^2$, $R^{11}$, $R^{12}$, $R^{13}$, $R^{14}$, $R^{15}$, $R^{16}$ and $R^{17}$ are each independently unsubstituted or substituted with one or more substituents, in one embodiment one, two or three substituents, each independently selected from $Q^1$.

In another embodiment, the compounds for use in the compositions and methods provided herein have Formula V:

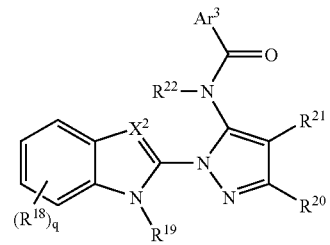

where $X^2$ is N or CR;
$Ar^3$ is aryl, alkyl, cycloalkyl, heterocyclyl, heteroaryl, alkenyl, alkynyl or COO-alkyl;
$R^{18}$, $R^{20}$ and $R^{21}$ are each independently selected as for $R^2$;
q is 0 to 4; and
$R^{19}$ and $R^{20}$ are each independently hydrogen, alkyl, alkenyl, alkynyl, cycloalkyl, heterocyclyl, aryl or heteroaryl;
where $X^2$, $Ar^2$, $R^{18}$, $R^{20}$, $R^{21}$, $R^{19}$ and $R^{22}$ are each independently unsubstituted or substituted with one or more substituents, in one embodiment one, two or three substituents, each independently selected from $Q^1$.

In another embodiment, the compounds for use in the compositions and methods provided herein have Formula VI:

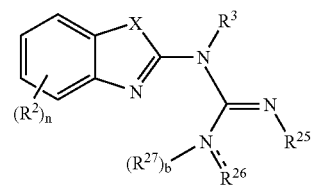

where X, $R^2$, $R^3$ and n are as defined elsewhere herein;
$R^{25}$ and $R^{26}$, together with the atoms to which they are attached, form a heterocyclyl or heteroaryl ring;
b is 1 when the N—$R^{26}$ bond is a single bond;
b is 0 when the N—$R^{26}$ bond is a double bond; and $R^{27}$ is hydrogen, alkyl, alkenyl, alkynyl, cycloalkyl, heterocyclyl, aryl or heteroaryl where X, $R^2$, $R^3$, $R^{25}$, $R^{26}$ and $R^{27}$ are each independently unsubstituted or substituted with one or more substituents, in one embodiment one, two or three substituents, each independently selected from $Q^1$.

In another embodiment, the compounds for use in the compositions and methods provided herein have Formula VII:

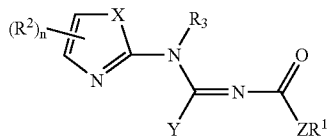

where X is O, S or NR, where R is hydrogen or alkyl;
Y is NRR or OH;
Z is a direct bond or NR;
$R^1$ is alkyl, alkenyl, alkynyl, cycloalkyl, aryl, heteroaryl, aralkyl, or aralkenyl;
$R^2$ is halo, pseudohalo, alkyl, cycloalkyl, alkoxy, aryl, aralkoxy, heteroaryl, aralkyl, or heteroaralkyl;
n is 0, 1, or 2;
$R^3$ is hydrogen or alkyl; and
where X, Y, Z, $R^1$, $R^2$ and $R^3$ are each independently unsubstituted or substituted with one or more substituents, in one embodiment one, two or three substituents, each independently selected from $Q^1$. As one of skill in the art will recognize, Formula VII structurally sets forth one tautomeric form of the genus of compounds; all such tautomeric forms are contemplated herein.

Also provided are pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Further provided are pharmaceutical compositions containing the compounds provided herein and a pharmaceutically acceptable carrier. In one embodiment, the pharmaceutical compositions are formulated for single dosage administration.

Also provided are methods of treating or ameliorating one or more symptoms of α-synuclein-mediated diseases or disorders. Such diseases and disorders include, but are not limited to, Parkinson's disease, dementia with Lewy bodies, multiple system atrophy and the Lewy body variant of Alzheimer's disease.

Method of treating or ameliorating one or more symptoms associated with α-synuclein toxicity are provided. Methods of prevention of α-synuclein fibril formation are provided. Methods of disruption or disaggregation of α-synuclein fibrils are provided. In further embodiments, methods of restoring vesicle trafficking and/or reversing changes in lipid metabolism are provided. In another embodiment, methods of slowing or reversing or ameliorating neurodegeneration are provided.

In practicing the methods, effective amounts of the compounds or compositions containing therapeutically effective concentrations of the compounds are administered.

Articles of manufacture are provided containing packaging material, a compound or composition provided herein which is useful for treating or ameliorating one or more symptoms of α-synuclein-mediated diseases or disorders, and a label that indicates that the compound or composition is useful for treating or ameliorating one or more symptoms of α-synuclein-mediated diseases or disorders.

DETAILED DESCRIPTION

A. Definitions

Figure 1:
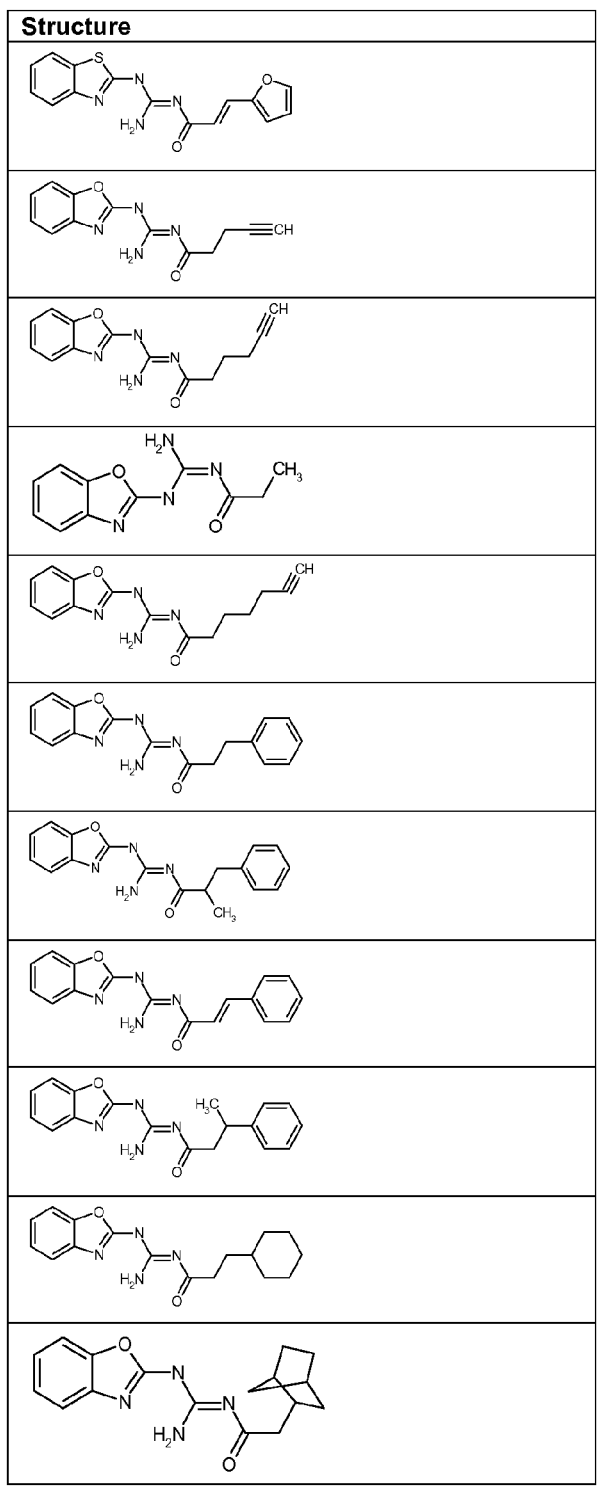
FIG. 1 sets forth the structures for certain compounds according to Formula I, as described herein.
Figure 1:
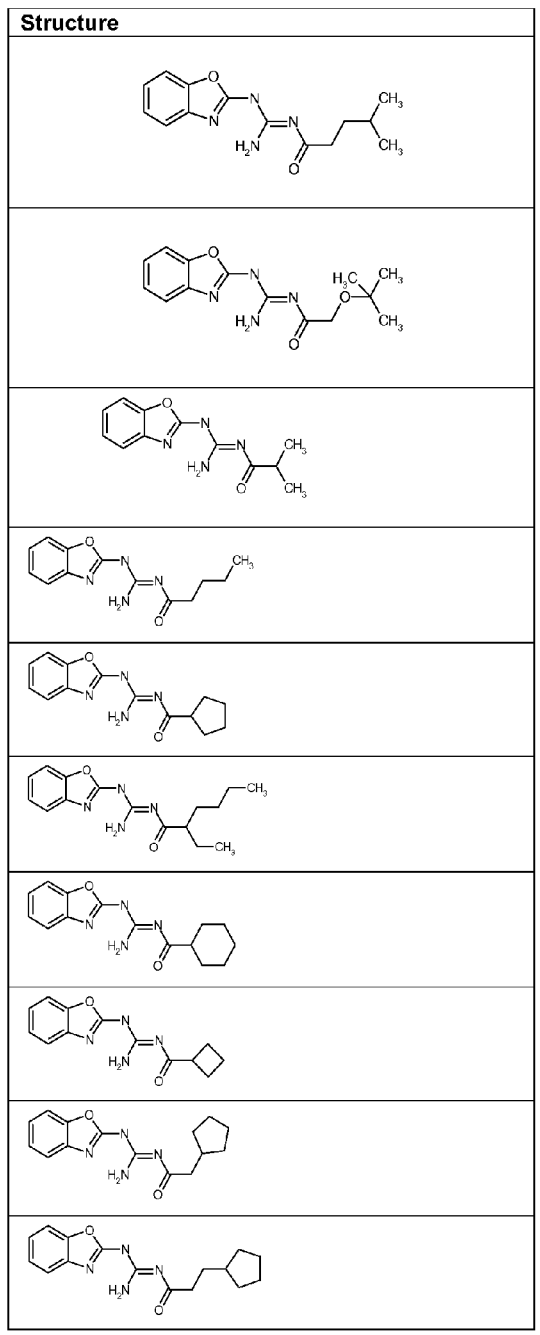
Figure 1:
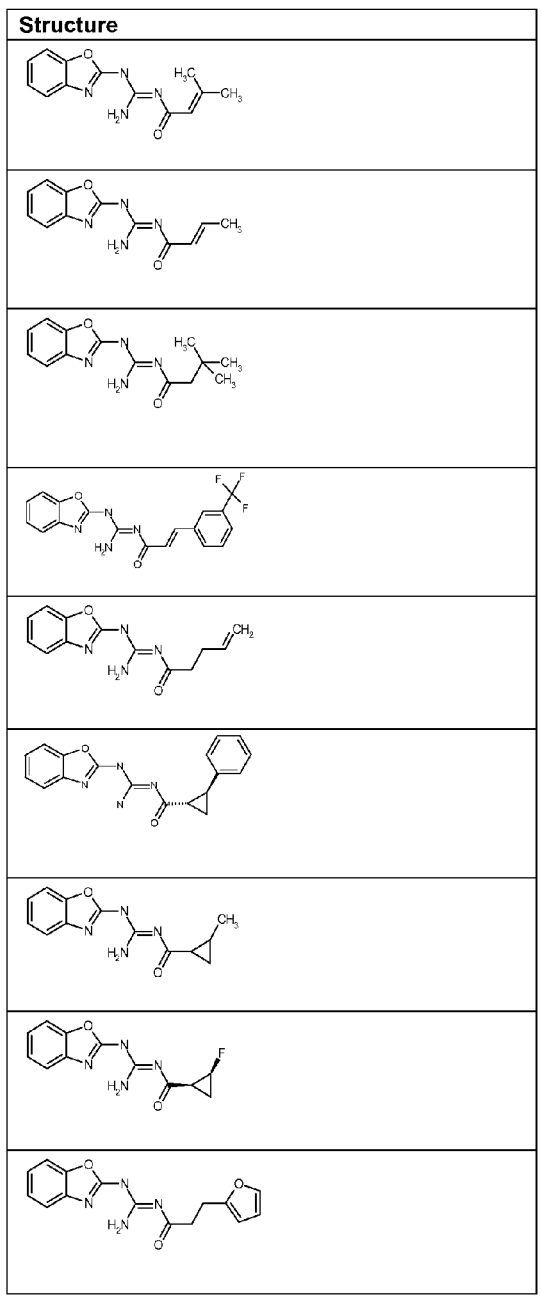
Figure 1:
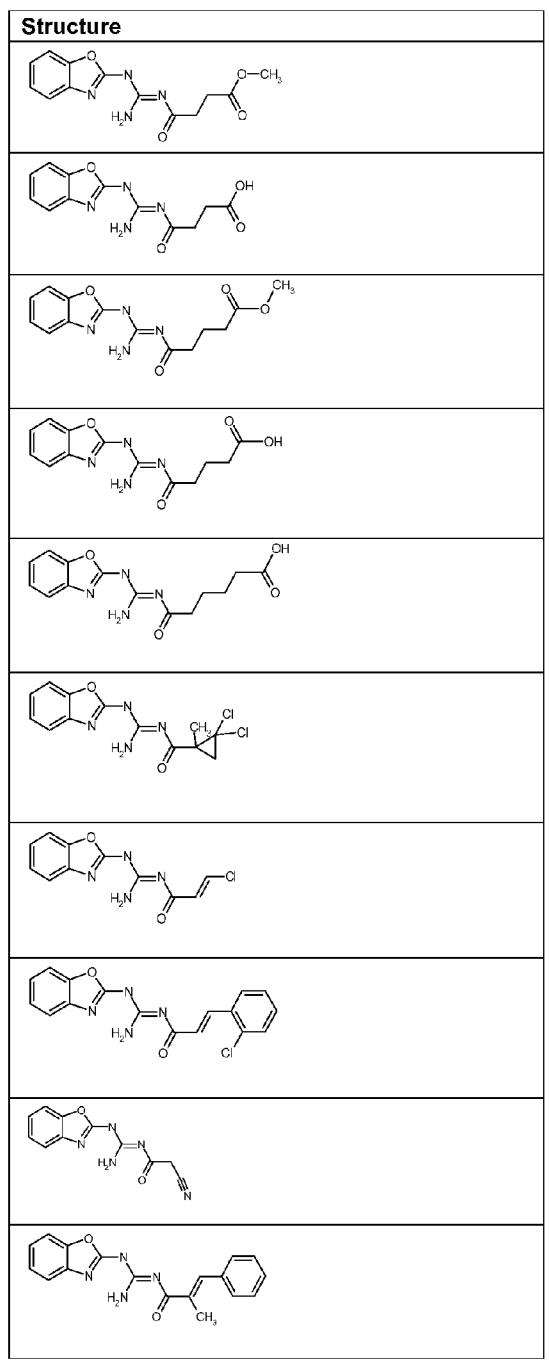
Figure 1:
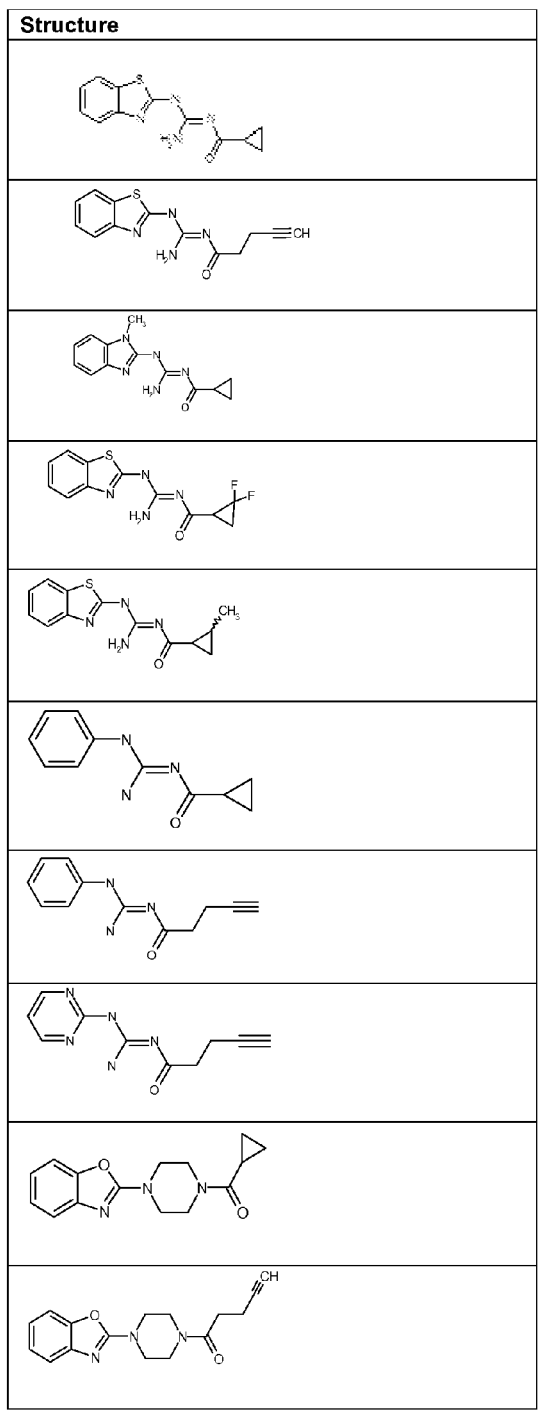
Figure 1:
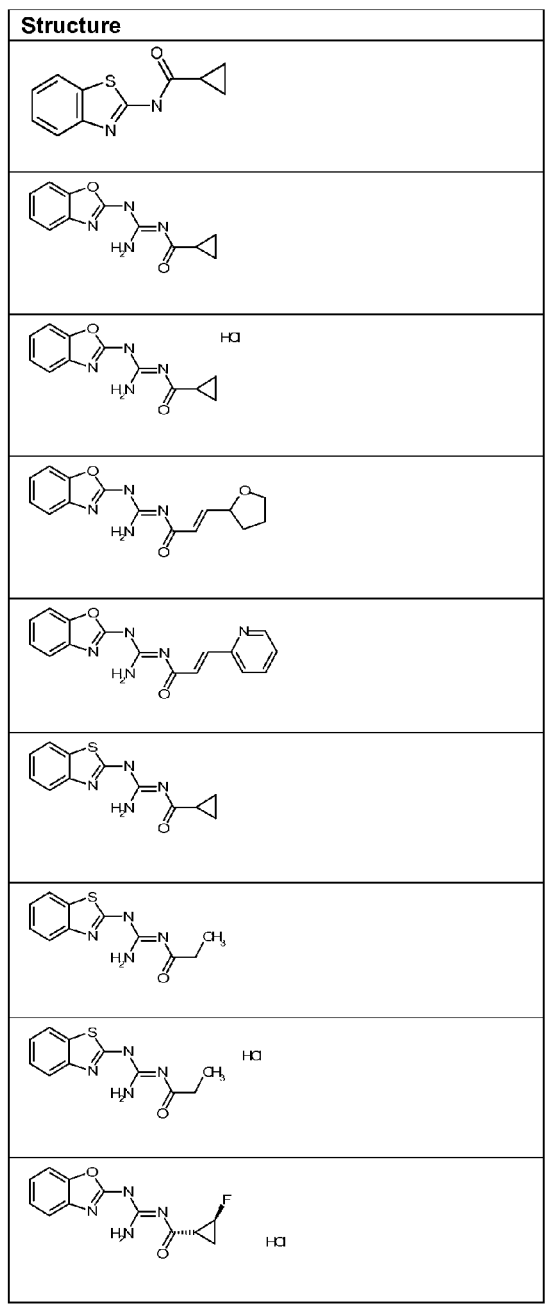
Figure 1:
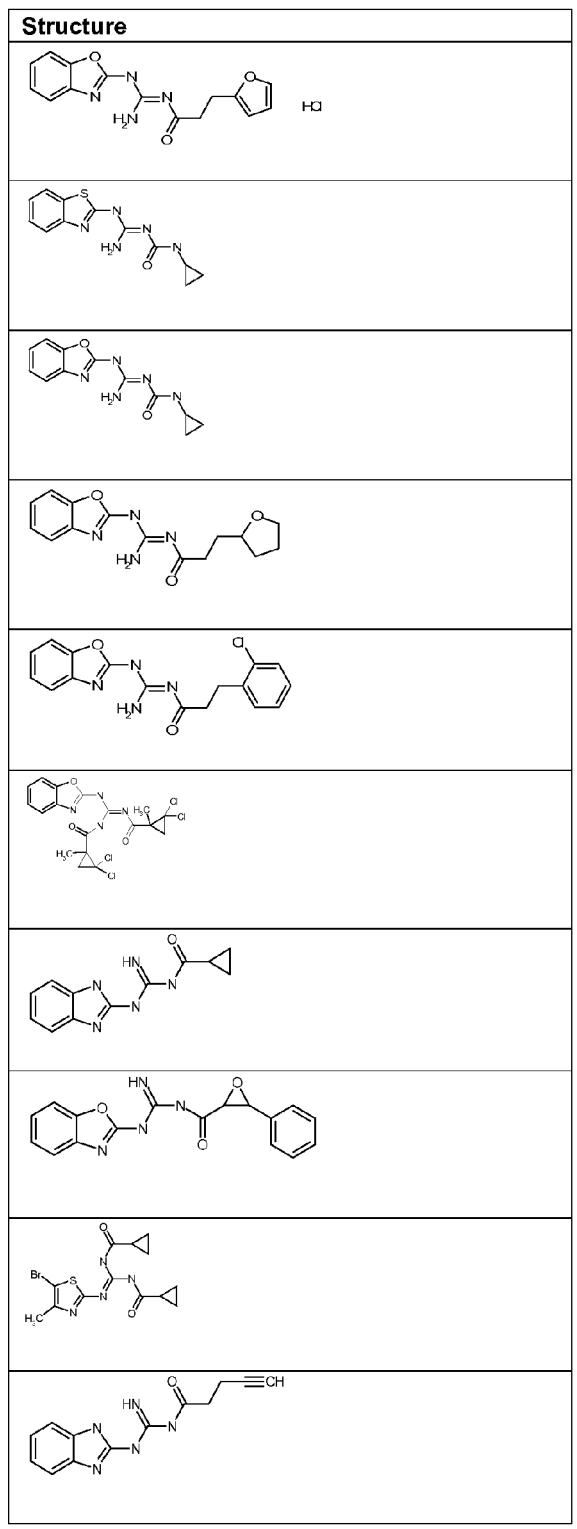
Figure 1:
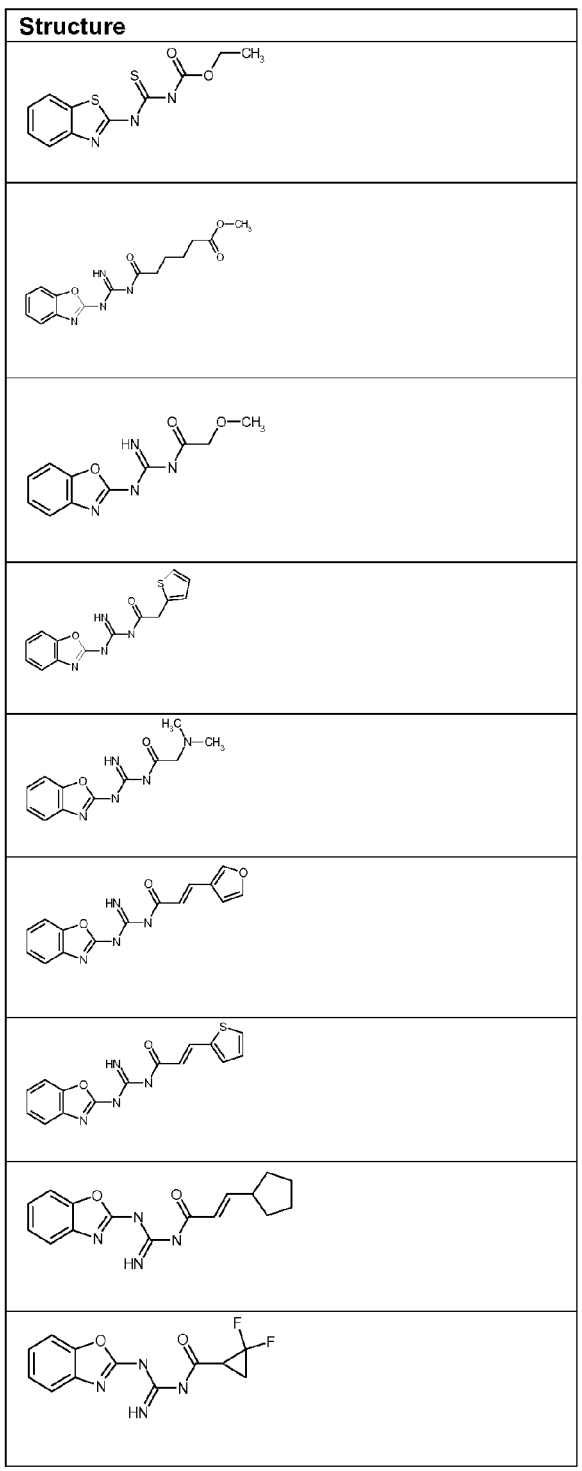
Figure 1:
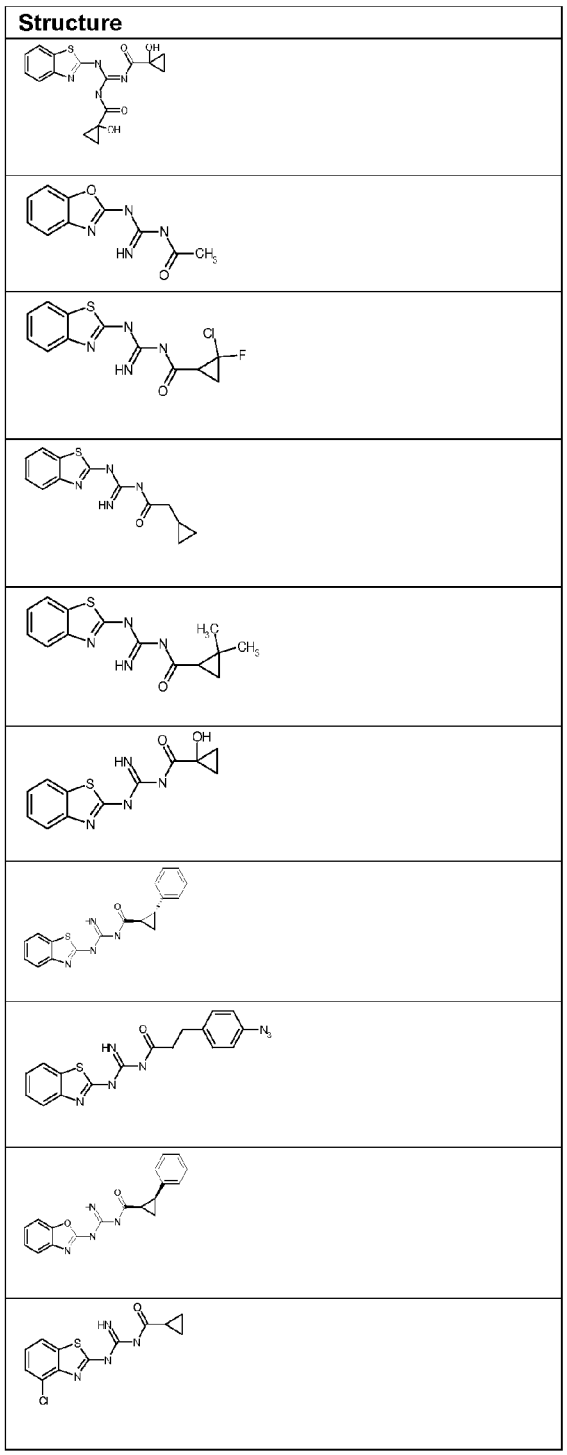
Figure 1:
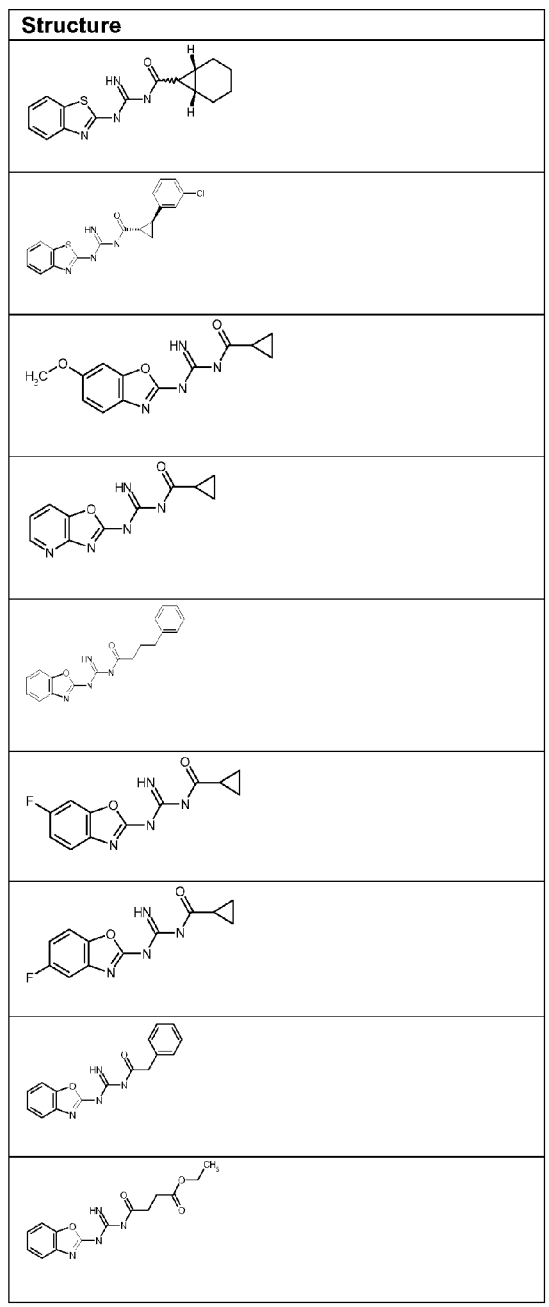
Figure 1:
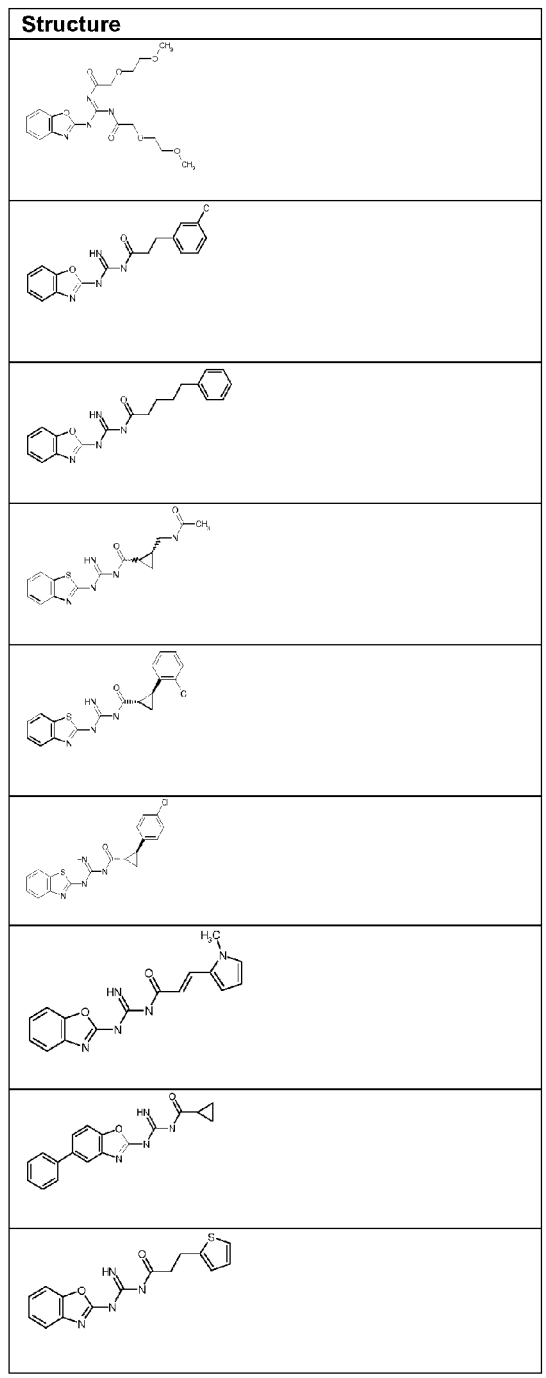
Figure 1:
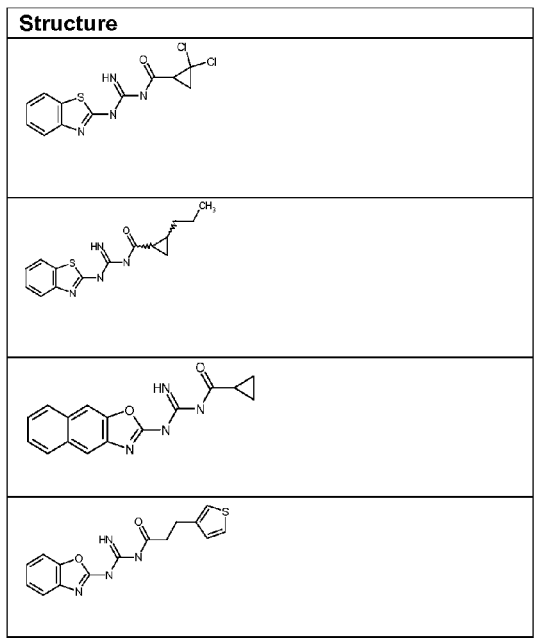

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, α-synuclein refers to one in a family of structurally related proteins that are prominently expressed in the central nervous system. Aggregated α-synuclein proteins form brain lesions that are hallmarks of some neurodegenerative diseases (synucleinopathies). The gene for α-synuclein, which is called SNCA, is on chromosome 4q21. One form of hereditary Parkinson disease is due to mutations in SNCA. Another form of hereditary Parkinson disease is due to a triplication of SNCA.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which α-synuclein fibril formation is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of α-synuclein fibril formation, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, alkyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O) NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O) NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O) NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR— (CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S(=O)— (CRR)$_m$—, and —(CRR)$_n$—S(=O)$_2$—(CRR)$_m$, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH— CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C≡C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylid-ene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO$_2$NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

The compounds provided herein for use in the compositions and methods provided herein exhibit in vitro and in vivo activity against α-synuclein mediated diseases and disorders. In one embodiment, the compounds treat or ameliorate one or more symptoms associated with α-synuclein toxicity. In one embodiment, the compounds affect aggregation of α-synuclein or fragments thereof. In another embodiment, the compounds do not affect aggregation, but still exert a therapeutic affect on α-synuclein toxicity.

In one embodiment, the compounds for use in the compositions and methods provided herein have Formula I:

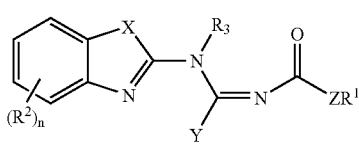

where X is O, S or NR, where R is hydrogen or alkyl;

Y is NRR' or OH, where R' is hydrogen or alkyl;

Z is a direct bond or NR;

$R^1$ is alkyl, alkenyl, alkynyl, cycloalkyl, aryl, heterocyclyl, heteroaryl, aralkyl, aralkenyl, heteroaralkyl, or heteroaralkenyl;

$R^2$ is halo, pseudohalo, alkoxy or alkyl;

n is 0 or 1;

$R^3$ is hydrogen or alkyl;

wherein X, Y, Z, $R^1$, $R^2$ and $R^3$ are each independently unsubstituted or substituted with one or more substituents, in one embodiment one, two or three substituents, each independently selected from $Q^1$.

In one embodiment, $R^1$ is substituted with one or more substituents independently selected from aryloxy, aryl, heteroaryl, halo, pseudohalo, alkyl, alkoxy, cycloalkyl, alkoxycarbonyl, hydroxycarbonyl, alkylamino, and dialkylamino.

In another embodiment, the compounds have Formula I where R is hydrogen.

In another embodiment, the compounds have Formula I where n is 0 or 1.

In another embodiment, the compounds have Formula I where X is S, O or NH.

In another embodiment, the compounds have Formula I where Y is $NH_2$.

In another embodiment, the compounds have Formula I where Z is a direct bond or NH.

In another embodiment, the compounds have Formula I where R is ethyl, 2-(2-furyl)ethenyl, phenyl, methyl, 2-naphthyloxymethyl, benzyl, 3-chloro-2-benzothienyl, cyclopropyl, cyclopropylmethyl, isobutyl, 4-tert-butylphenyl, 4-biphenyl, tert-butyl, 3-chlorophenyl, 2-furyl, 2,4-dichlorophenyl, 3,4-dimethoxyphenyl, 2-(4-methoxyphenyl)ethenyl, 4-methoxyphenoxymethyl, isopentyl, isopropyl, 2-cyclopentylethyl, cyclopentylmethyl, 2-phenylpropyl, 2-phenylethyl, 1-methyl-2-phenylethyl, 1-methyl-2-phenylethenyl, 2-benzylethyl, 2-phenylethenyl, 5-hexynyl, 3-butynyl, 4-pentynyl, propyl, butyl, pentyl, hexyl, t-butoxymethyl, t-butylmethyl, 1-ethylpentyl, cyclopentyl, cyclohexyl, cyclobutyl, 2-cyclopentylethyl, cyclopentylmethyl, 2-fluorocyclopropyl, 2-methylcyclopropyl, 2-phenylcyclopropyl, 2,2-dimethylethenyl, 1,2-propenyl, 2-(3-trifluoromethylphenyl)ethenyl, 3,4-butenyl, 2-(2-furyl)ethyl, 2-chloroethenyl, 2-(2-chlorophenyl)ethenyl, 1-methyl-2,2-dichlorocyclopropyl, 2,2-difluorocyclopropyl, methylpropionate, proprionic acid, methylbutyrate, butyric acid, pentanoic acid, methyl-t-butylether, dimethylaminomethyl, 2-(2-tetrahydrofuryl)-ethyl, or 2-(2-tetrahydrofuryl)-methyl.

In another embodiment, $R^2$ is halo or alkyl. In another embodiment, $R^2$ is chloro or methyl.

In another embodiment, $R^3$ is hydrogen.

In another embodiment, compounds of Formula I include:

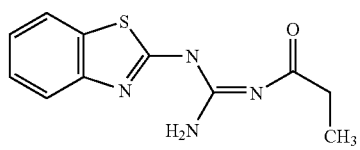

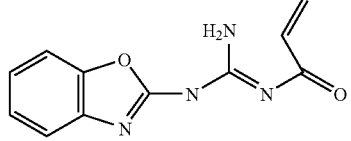

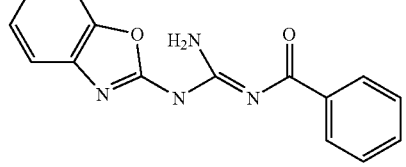

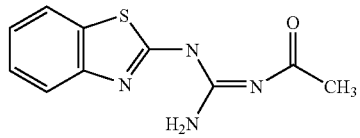

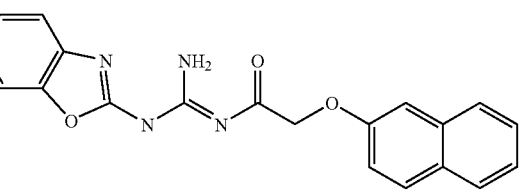

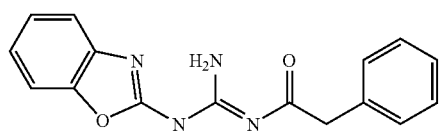

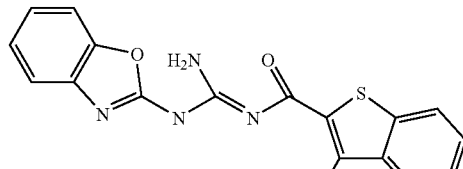

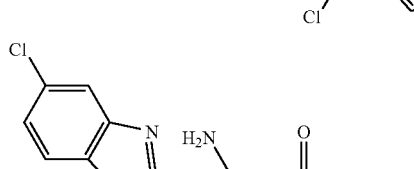

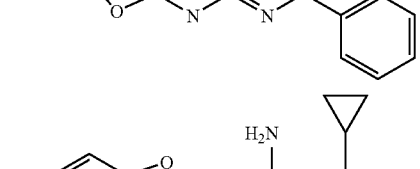

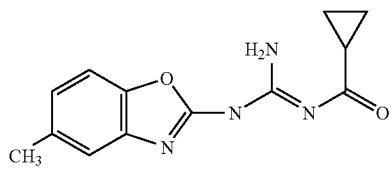

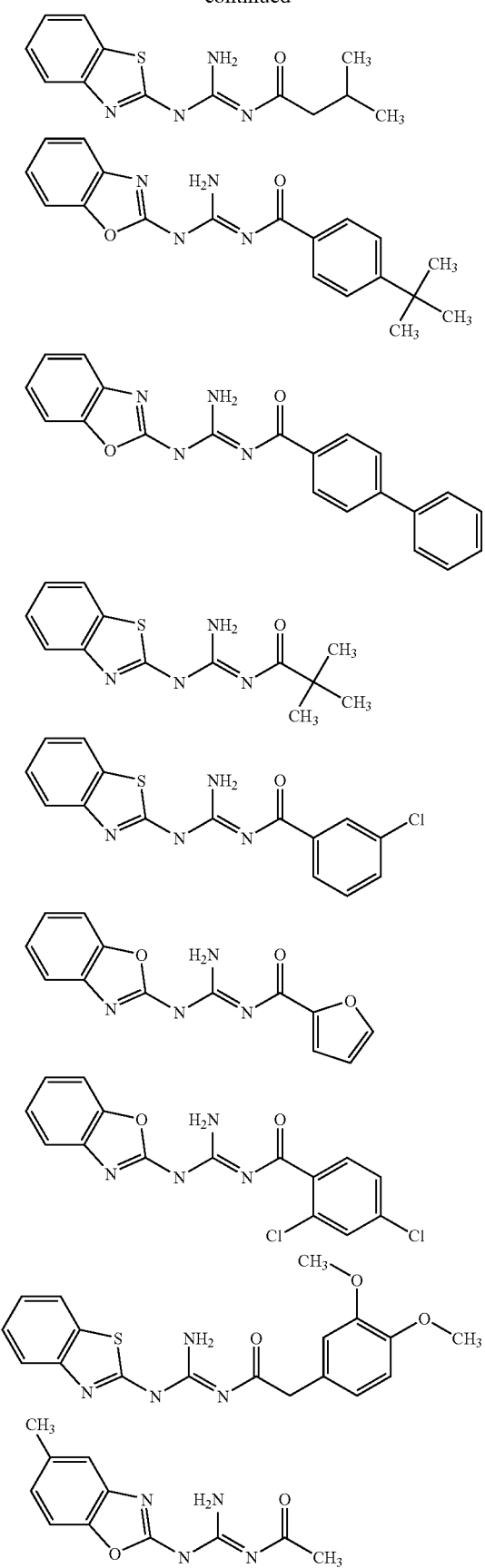
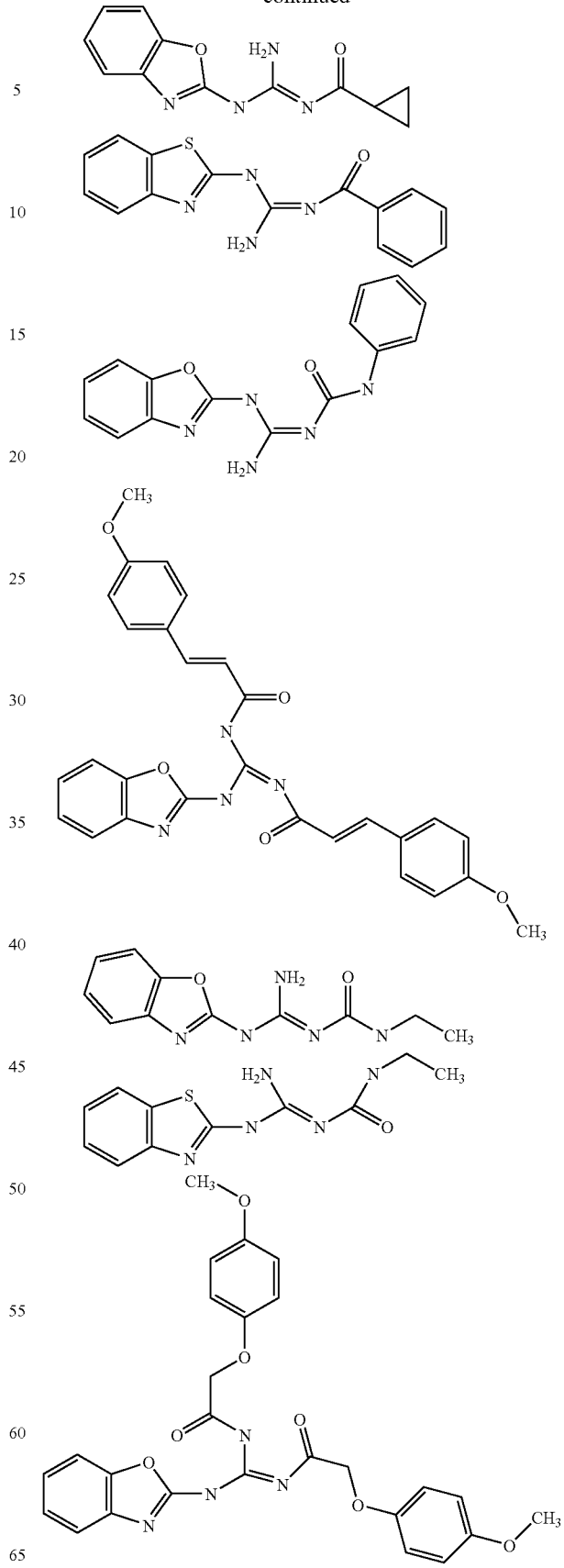

In another embodiment, the compounds of Formula I can have a structure as set forth in FIG. 1.

In another embodiment, the compounds for use in the compositions and methods provided herein have Formula II:

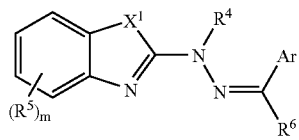

where $X^1$ is O or NR, where R is H or alkyl;

Ar is aryl or heteroaryl, and is unsubstituted or substituted with alkoxy, alkyl, hydroxy, alkylenedioxy, dialkylamino, heterocyclyl or carboxy;

$R^4$ is alkyl or hydrogen;

$R^5$ is halo or pseudohalo;

m is 0 or 1;

$R^6$ is hydrogen or alkyl;

wherein $X^1$, Ar, $R^4$, $R^5$ and $R^6$ are each independently unsubstituted or substituted with one or more substituents, in one embodiment one, two or three substituents, each independently selected from $Q^1$.

In another embodiment, the compounds have Formula II where $X^1$ is O or NH.

In another embodiment, the compounds have Formula II where Ar is phenyl, naphthyl, indolyl, pyridyl, thienyl or furyl, and is unsubstituted or substituted with alkoxy, alkyl, hydroxy, alkylenedioxy, dialkylamino, heterocyclyl or carboxy. In another embodiment, the compounds have Formula II where Ar is phenyl, naphthyl, indolyl, pyridyl, thienyl or furyl, and is unsubstituted or substituted with methoxy, tert-butyl, hydroxy, methylenedioxy, methyl, dimethylamino, morpholinyl or carboxy. In another embodiment, the compounds have Formula II where Ar is 4,8-dimethoxy-1-naphthyl, 3-indolyl, phenyl, 3-pyridyl, 3,5-di-tert-butyl-4-hydroxyphenyl, 2,3-dimethoxyphenyl, 3,4-methylenedioxyphenyl, 2-thienyl, 3,4-dimethoxyphenyl, 5-methyl-2-furyl, 4-dimethylaminophenyl, 4-(4-morpholinyl)phenyl, 3-methoxyphenyl, 2-naphthyl, 2-pyridyl, 5-(4-carboxyphenyl)-2-furyl or 4-methoxyphenyl.

In another embodiment, the compounds have Formula II where $R^4$ is H.

In another embodiment, the compounds have Formula II where $R^5$ is Cl.

In another embodiment, the compounds have Formula II where m is 0 or 1.

In another embodiment, the compounds have Formula II where $R^6$ is H, In another embodiment, compounds of Formula II include:

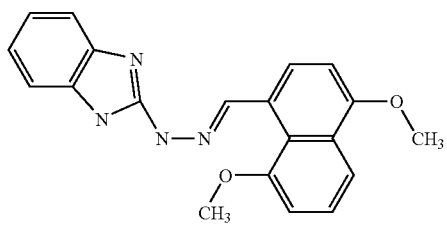

-continued

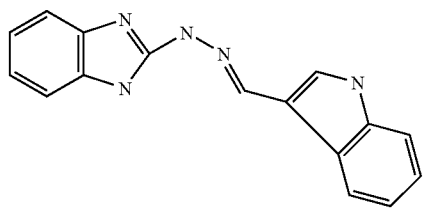

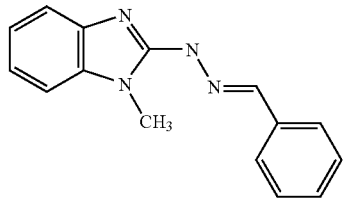

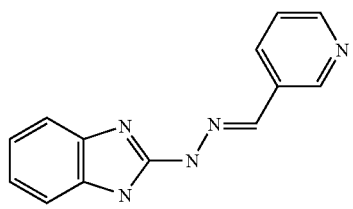

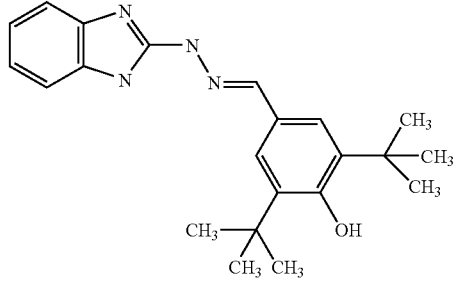

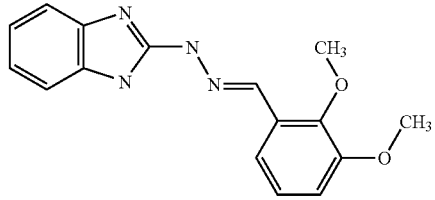

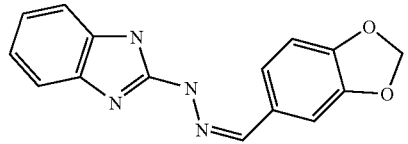

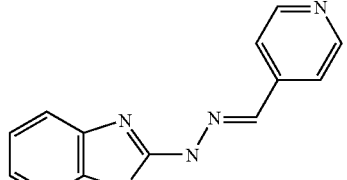

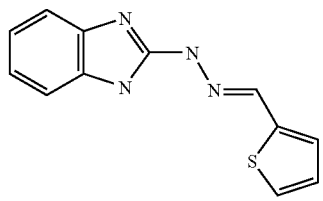

-continued

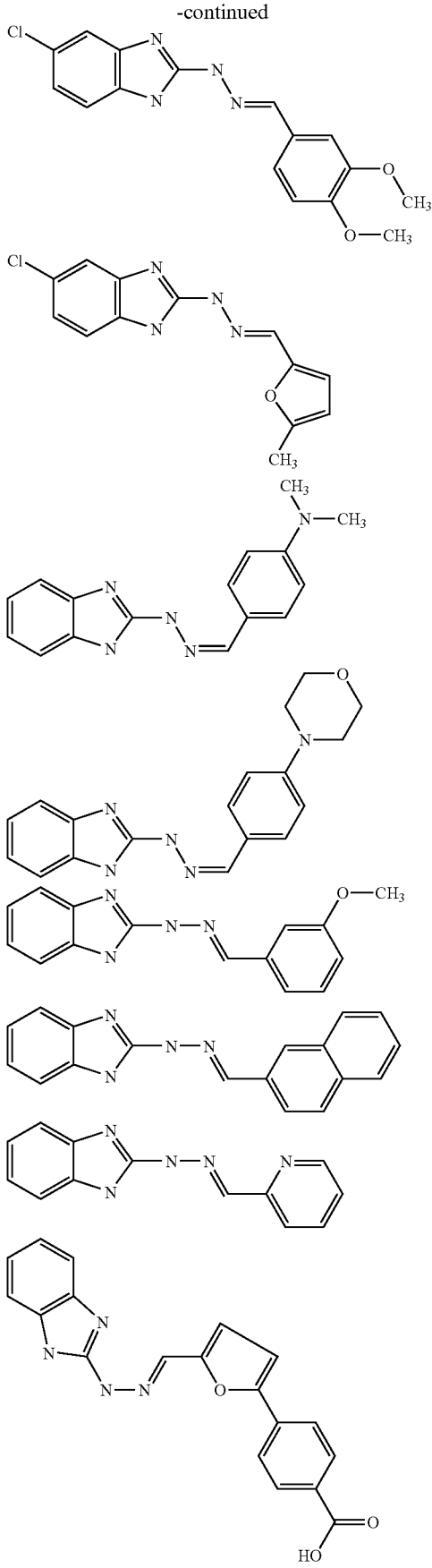

-continued

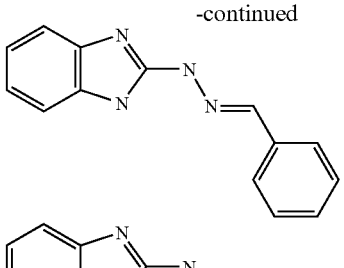

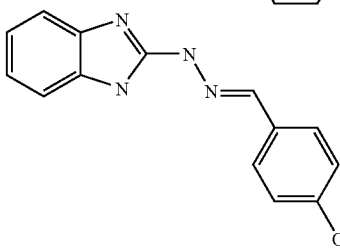

In another embodiment, the compounds for use in the compositions and methods provided herein have Formula III:

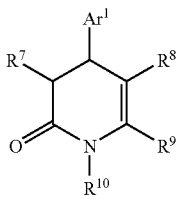

where $Ar^1$ is aryl or heteroaryl, and is unsubstituted or substituted with alkyl, alkenyl, halo, pseudohalo, dialkylamino, aryloxy, haloalkyl, alkoxy, cycloalkyl, heteroaryl, or COOR, where R is hydrogen or alkyl;

$R^7$ is hydrogen or NRR, where R is hydrogen or alkyl;

$R^8$ and $R^9$ are each independently selected from (i) and (ii) as follows:

(i) $R^8$ and $R^9$ together with the atoms to which they are attached form a fused phenyl ring; and (ii) $R^8$ is CN or COOR$^{200}$, where $R^{200}$ is hydrogen, alkyl, alkenyl, alkynyl, cycloalkyl, heterocyclyl, aryl or heteroaryl; and $R^9$ is hydrogen, alkyl or alkylthio; and $R^{10}$ is hydrogen;

where $Ar^1$, $R^7$, $R^8$, $R^9$ and $R^{10}$ are each independently unsubstituted or substituted with one or more, in one embodiment one, two or three substituents, each independently selected from $Q^1$.

In one embodiment of (i) above, $R^8$ and $R^9$ together with the atoms to which they are attached form a fused phenyl ring, which is unsubstituted or substituted with halo, pseudohalo, alkyl, alkoxy, cycloalkyl, fused cycloalkyl, fused heterocyclic, fused heteroaryl, aryl (e.g., phenyl), and fused aryl (e.g., fused phenyl ring), which is unsubstituted or substituted with halo, pseudohalo, alkyl, alkoxy, aryl, cycloalkyl, heterocyclyl, fused aryl, fused heterocyclyl, and fused cycloalkyl.

In another embodiment, $Ar^1$ is phenyl, naphthyl, pyridyl, furyl, or thienyl, and is unsubstituted or substituted with alkyl, alkenyl, halo, pseudohalo, dialkylamino, aryloxy, haloalkyl, alkoxy, aryloxy, cycloalkyl, heterocyclyl, fused heterocyclyl, aryl, fused aryl, heteroaryl, fused heteroaryl, or COOR, where R is hydrogen or alkyl.

In another embodiment, $Ar^1$ is substituted with methyl, fluoro, bromo, chloro, iodo, dimethylamino, phenoxy, trifluoromethyl or methoxycarbonyl.

In another embodiment, $Ar^1$ is phenyl, 2-thienyl, 3-thienyl, 2-furyl, 3-furyl, 5-chloro-2-thienyl, 5-bromo-2-thienyl, 3-methyl-2-thienyl, 5-methyl-2-thienyl, 5-ethyl-2-thienyl, 2-methylphenyl, 3-methylphenyl, 3-trifluoromethyl, 3-bromophenyl, 4-fluoro-3-bromophenyl, 2-fluorophenyl, 3,4-difluorophenyl, 2-chlorophenyl, 3-chlorophenyl, 3,4-dichlorophenyl, 3,4,5,-methoxyphenyl, 2,4-methoxyphenyl, 2-fluoro-5-bromophenyl, 4-dimethylaminophenyl, 2-trifluoromethyl-4-fluorophenyl, 3-trifluoromethyl-4-fluorophenyl, 2-fluoro-3-chlorophenyl, 3-bromo-4-fluorophenyl, perfluorophenyl, 3-pyridyl, 4-pyridyl, 4-bromophenyl, 4-chlorophenyl, 3-phenoxyphenyl, 2,4-dichlorophenyl, 2,3-difluorophenyl, 2-chlorophenyl, 2-fluoro-6-chlorophenyl, 1-naphthyl, 4-trifluoromethylphenyl, 2-trifluoromethylphenyl, 4-trifluoromethoxyphenyl, or 4-methoxycarbonylphenyl.

In another embodiment, $R^7$ is hydrogen or dialkylamino. In another embodiment, $R^7$ is hydrogen or diethylamino.

In another embodiment, $R^8$ and $R^9$ are each independently selected from (i) and (ii) as follows:

(i) $R^8$ and $R^9$ together with the atoms to which they are attached form a fused phenyl ring, which is unsubstituted or substituted with methyl, chloro, methoxy or another fused phenyl ring, which is unsubstituted or substituted with bromo; and (ii) $R^8$ is CN or $COOR^{200}$, where $R^{200}$ is methyl, benzyl, ethyl, 4-methoxybenzyl or 2-phenylethyl; and $R^9$ is methyl, methylthio or phenylaminocarbonylmethylthio.

In another embodiment, compounds of Formula III include:

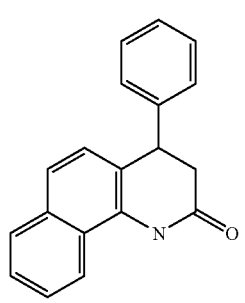
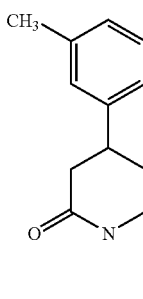
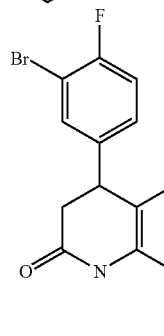
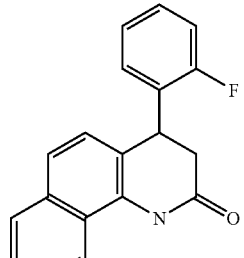
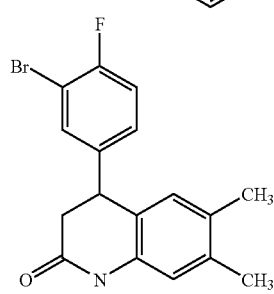
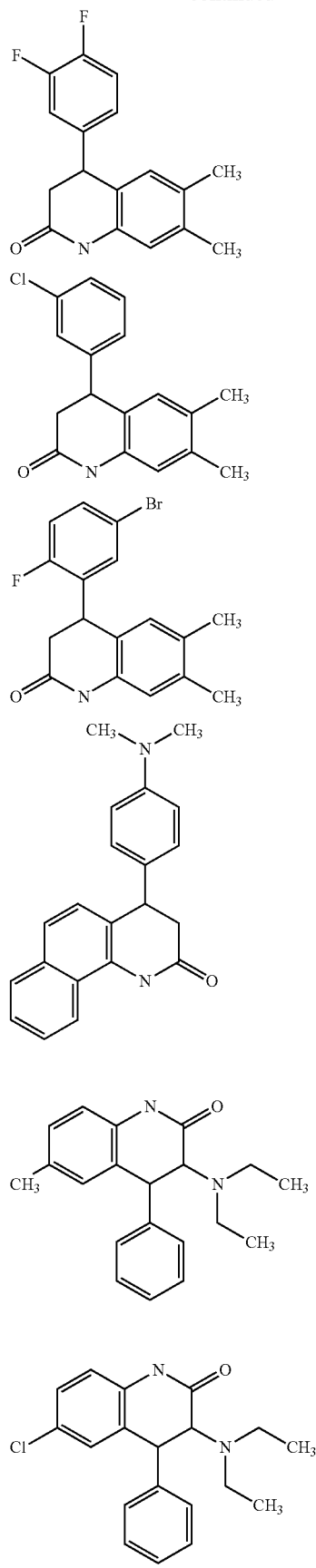

-continued
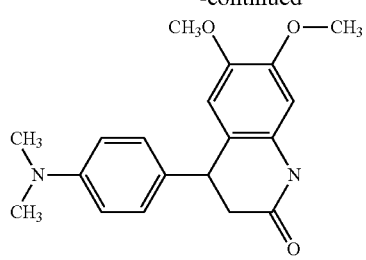
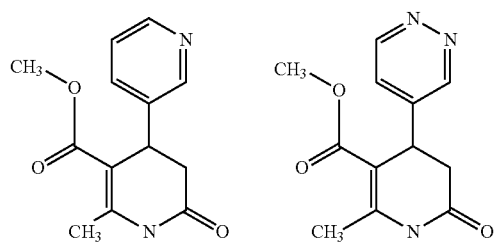
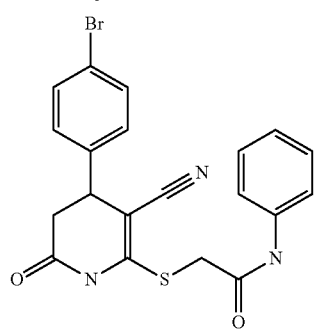
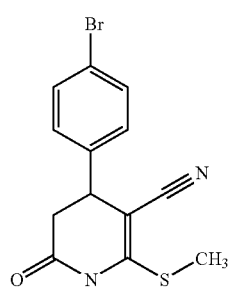
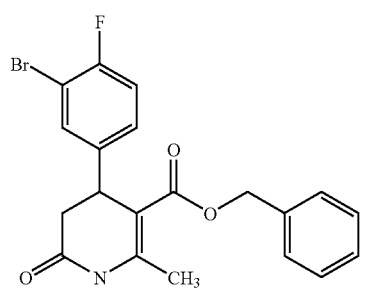
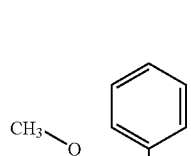
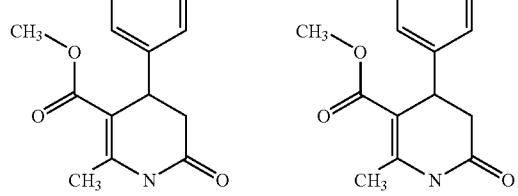
-continued
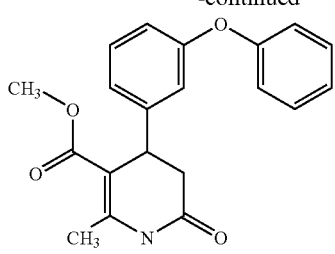
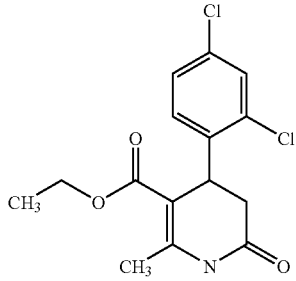
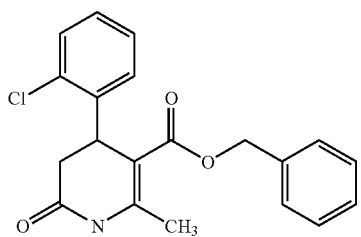
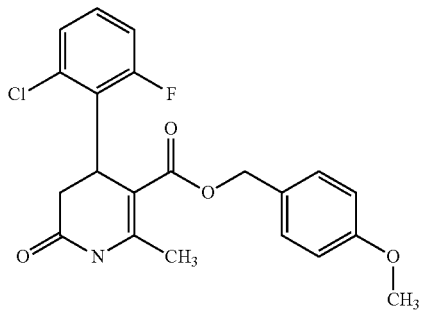
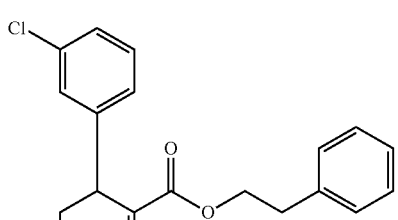
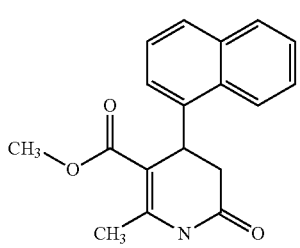

-continued

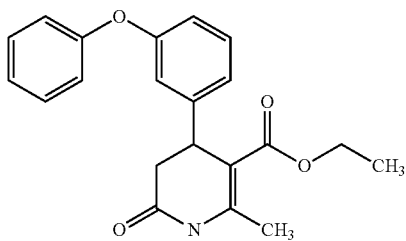

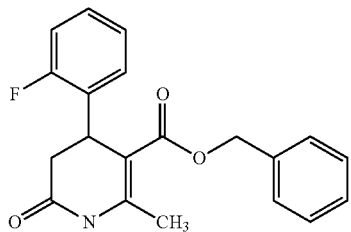

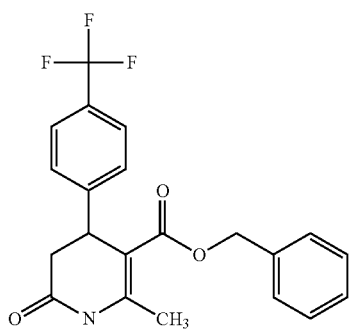

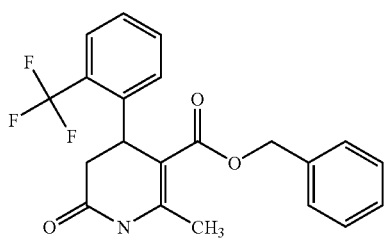

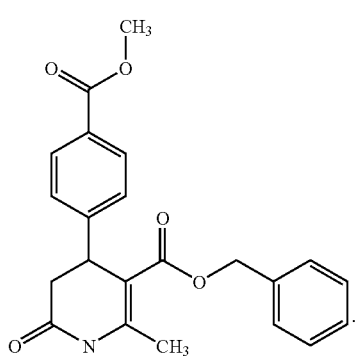

Figure 3:
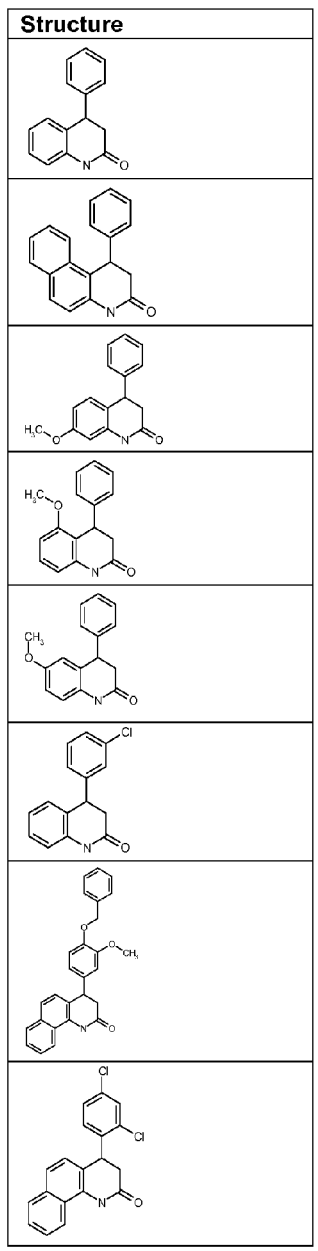
FIG. 3 sets forth the structures for certain compounds according to Formula III, as described herein.
Figure 3:
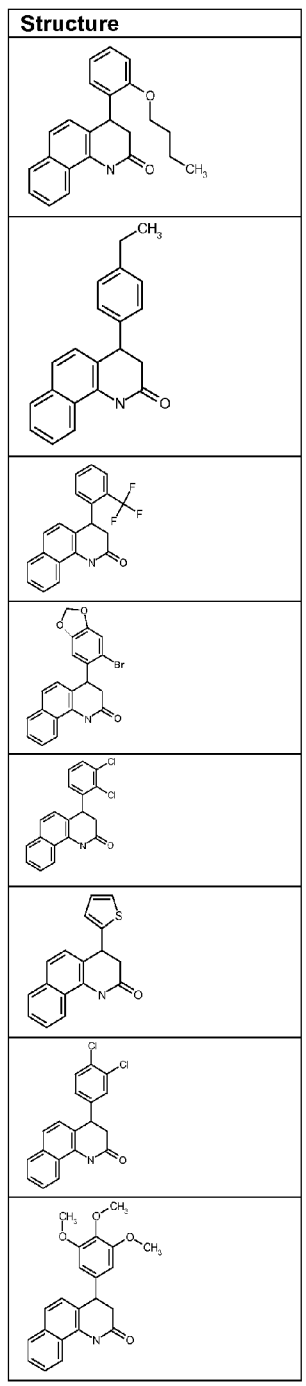
Figure 3:
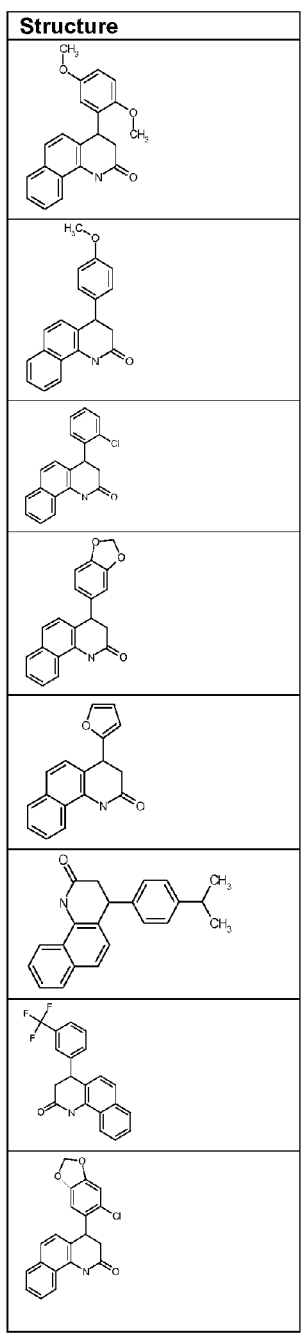
Figure 3:
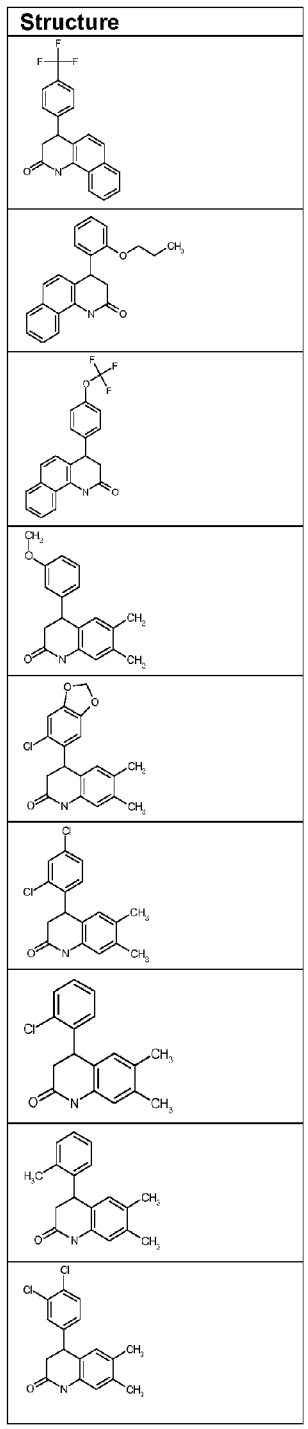
Figure 3:
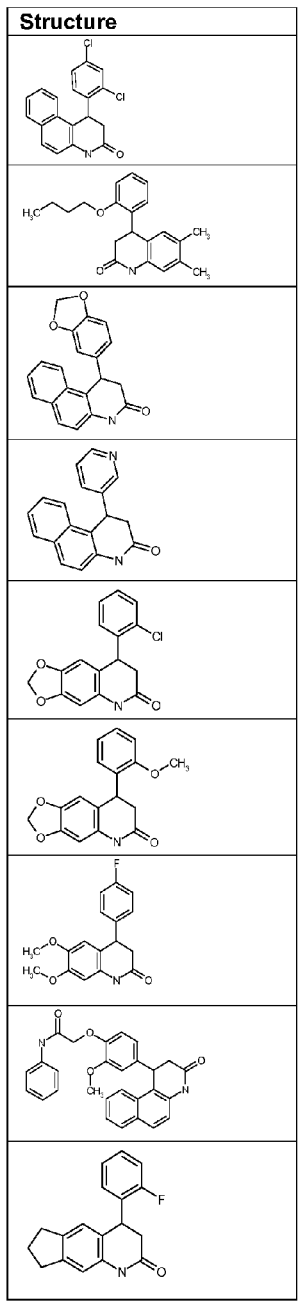
Figure 3:
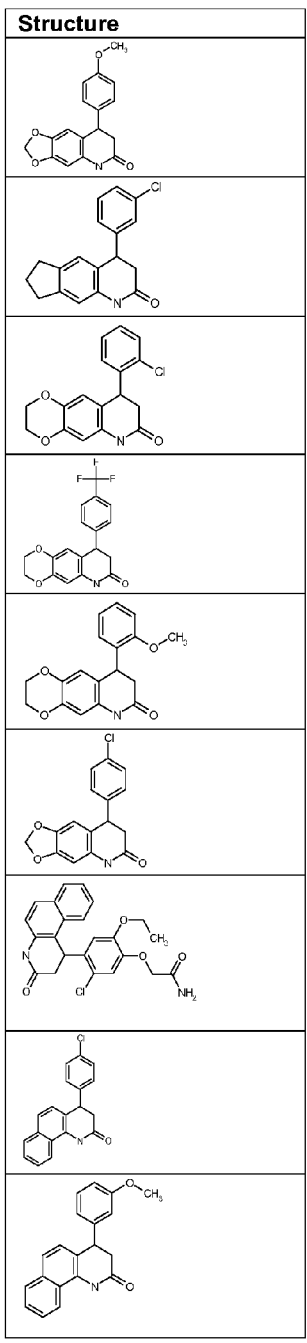
Figure 3:
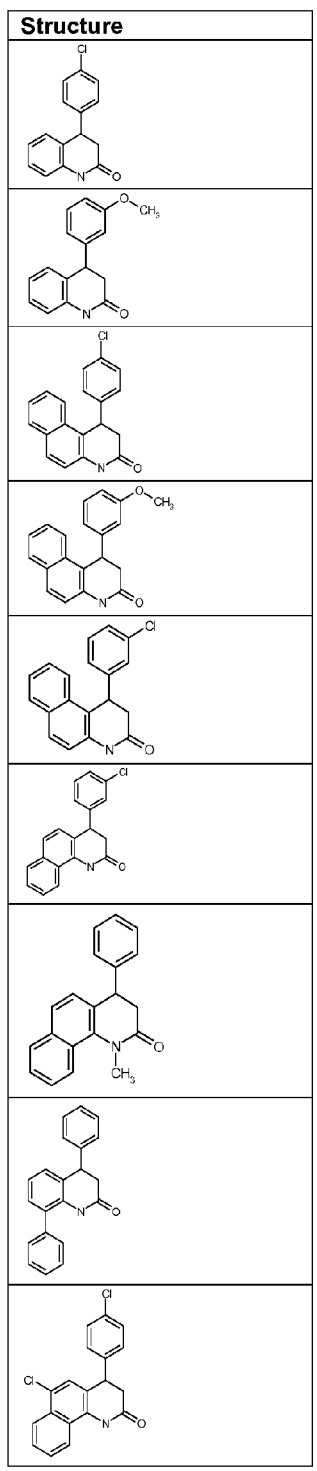
Figure 3:
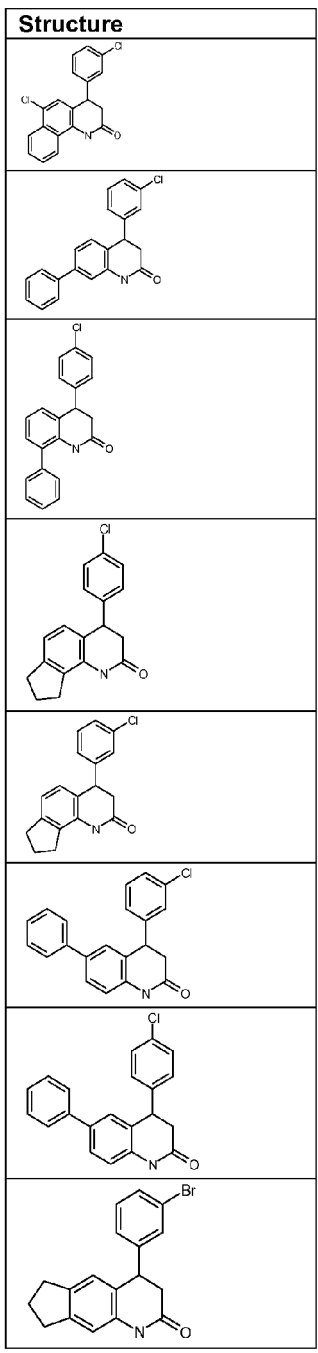
Figure 3:
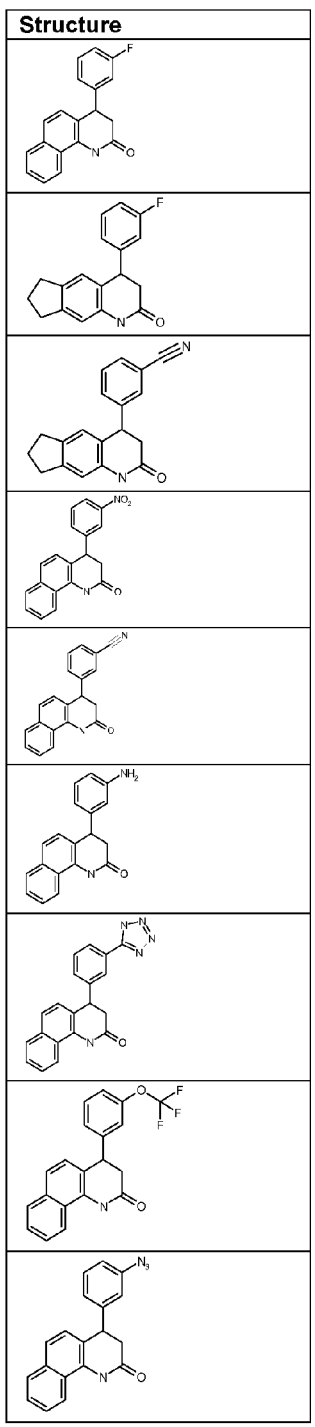
Figure 3:
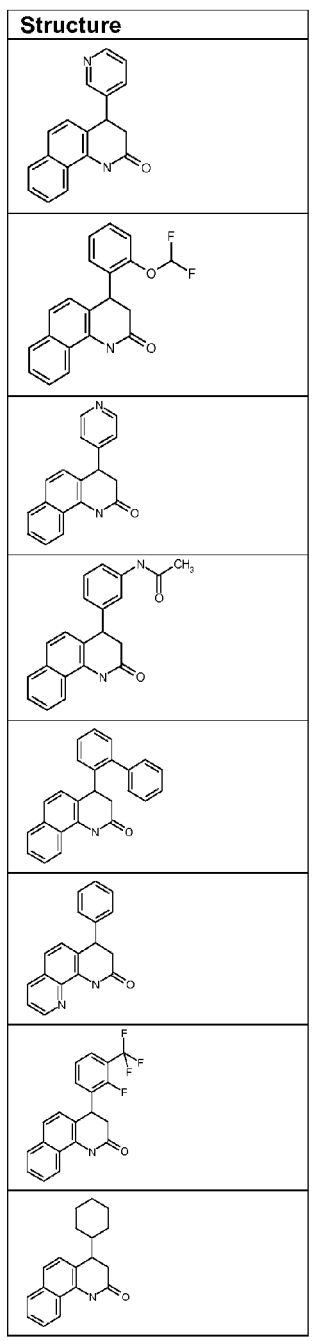
Figure 3:
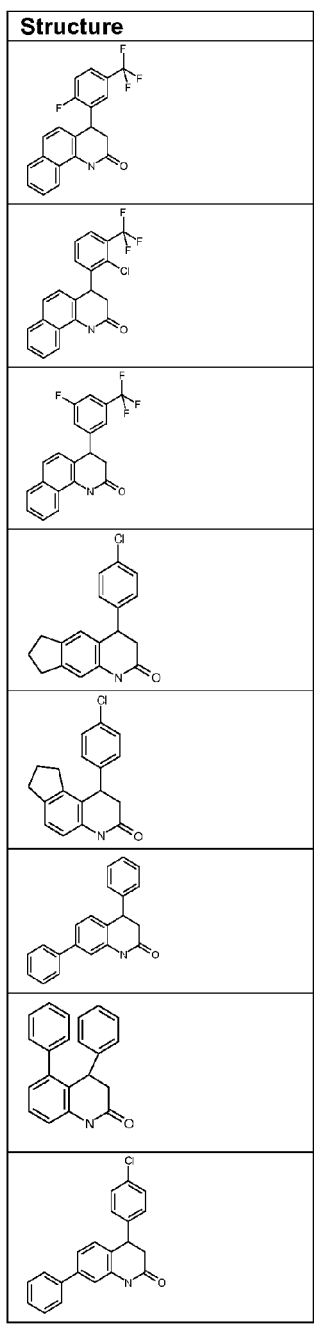
Figure 3:
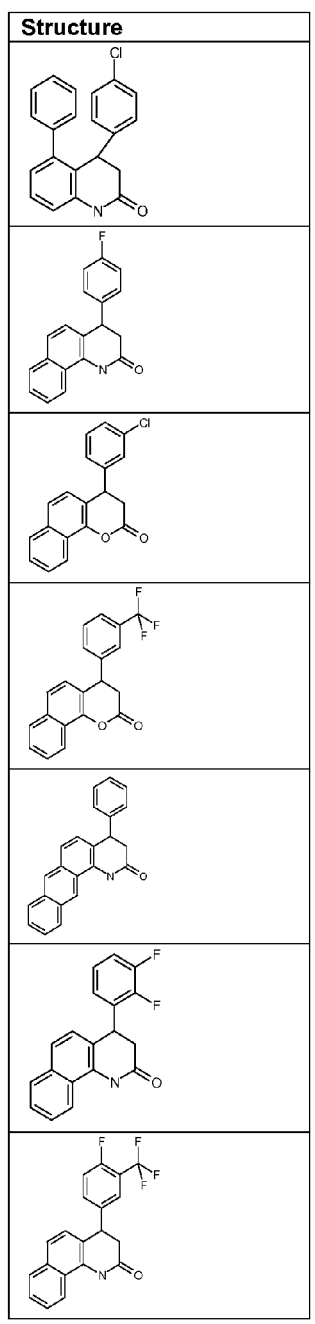
Figure 3:
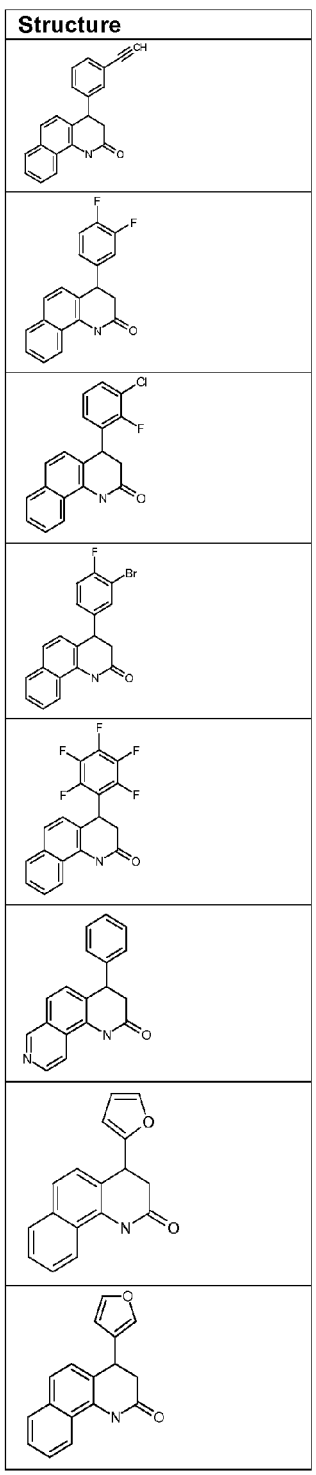
Figure 3:
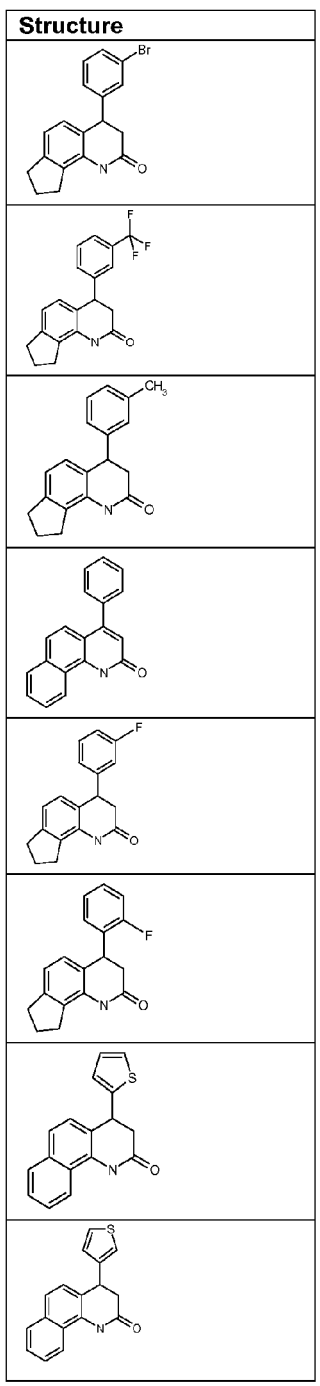
Figure 3:
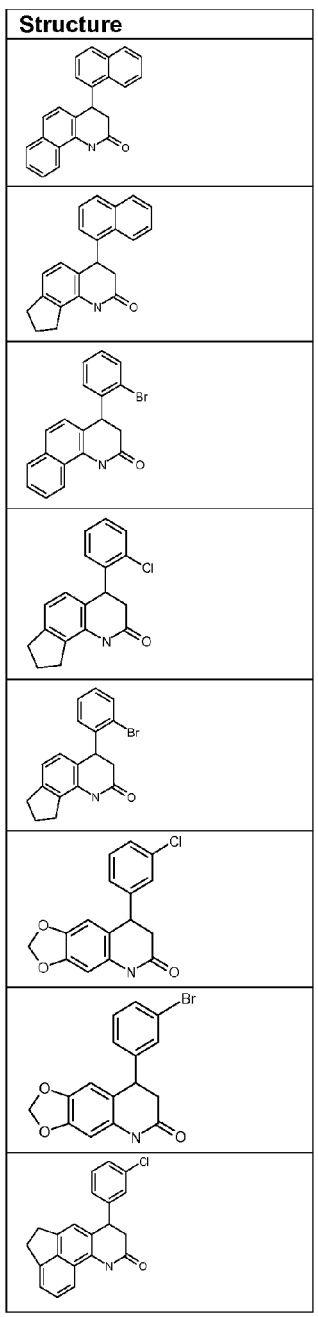
Figure 3:
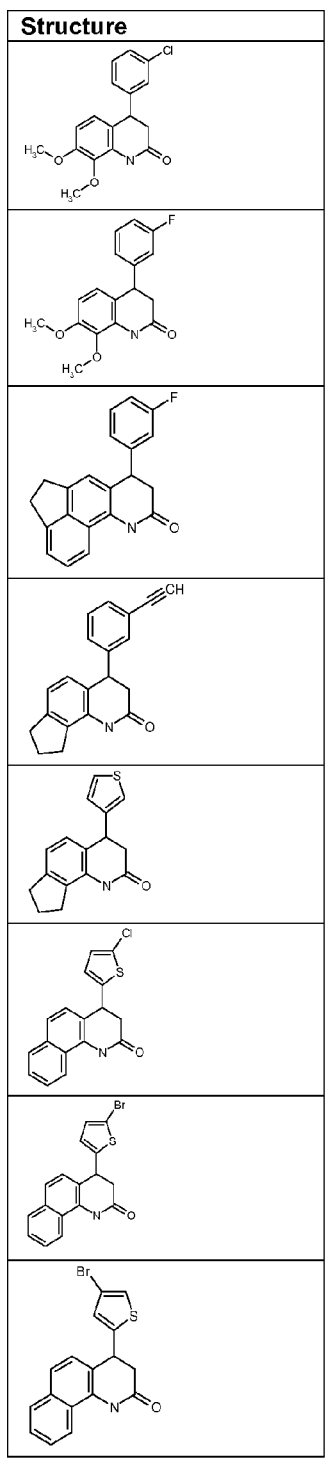
Figure 3:
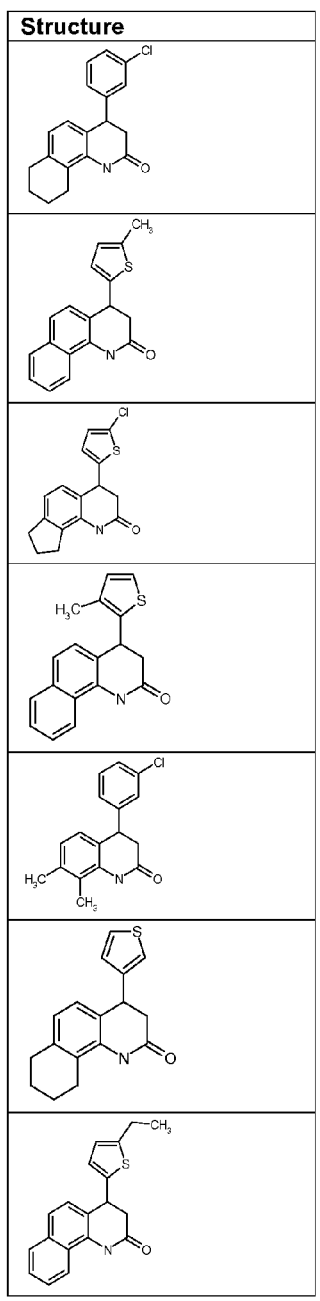
Figure 3:
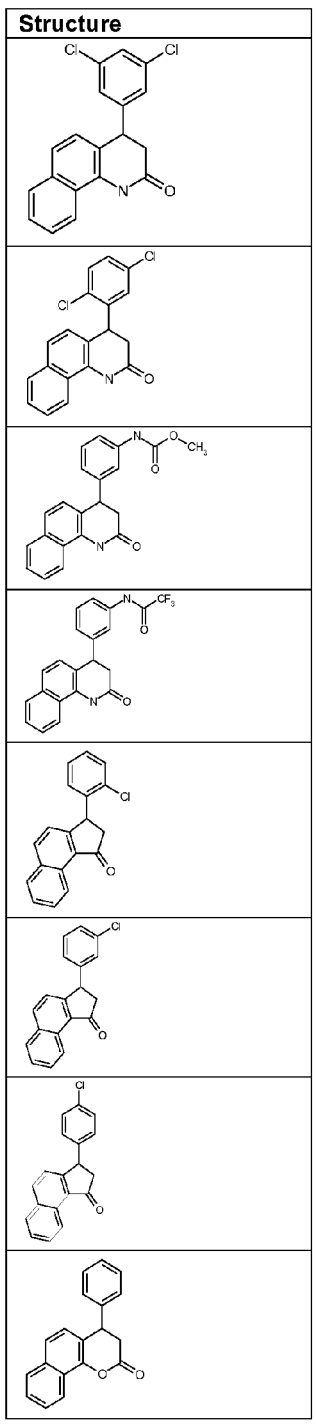
Figure 3:
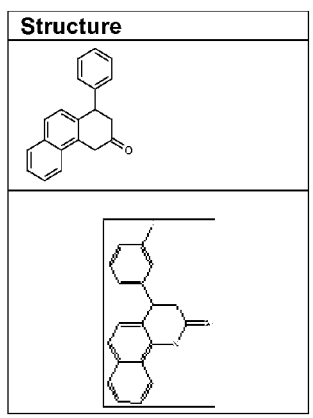

In another embodiment, compounds according to Formula III can have a structure as set forth in FIG. 3.

In another embodiment, the compounds for use in the compositions and methods provided herein have Formula IV:

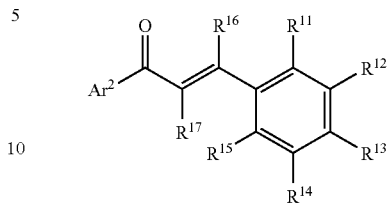

where $Ar^2$ is heteroaryl; and $R^{11}$, $R^{12}$, $R^{13}$, $R^{14}$ and $R^{15}$ are each independently hydrogen, halo, pseudohalo, nitro, alkoxy, dialkylamino or aralkoxy; and $R^{16}$ and $R^{17}$ are each hydrogen;

In another embodiment, the compounds have Formula IV where $Ar^2$ is thienyl. In another embodiment, the compounds have Formula IV where $Ar^2$ is 2-thienyl.

In another embodiment, the compounds have Formula IV where $R^{11}$, $R^{12}$, $R^{13}$, $R^{14}$ and $R^{15}$ are each independently hydrogen, chloro, nitro, methoxy, dimethylamino, benzyloxy, ethoxy or cyano.

In another embodiment, the compounds of Formula IV are:

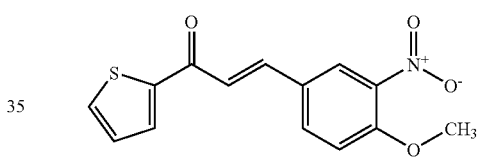

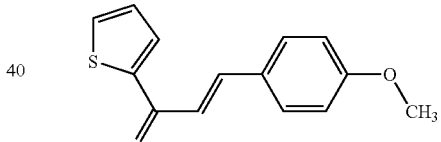

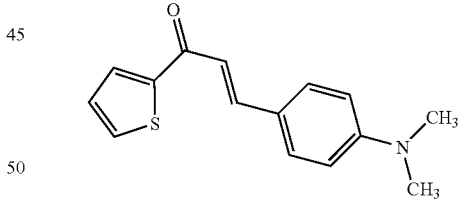

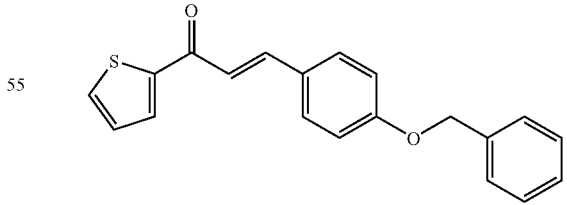

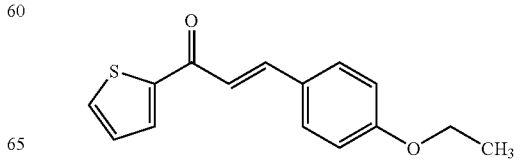

-continued

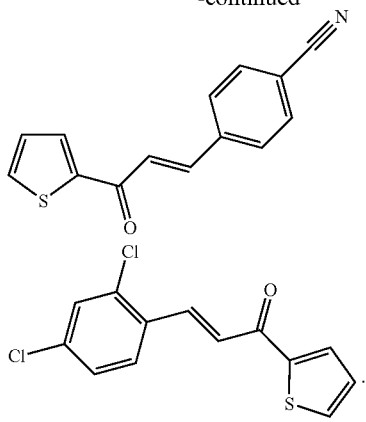

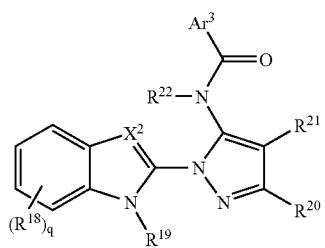

In another embodiment, the compounds for use in the compositions and methods provided herein have Formula V:

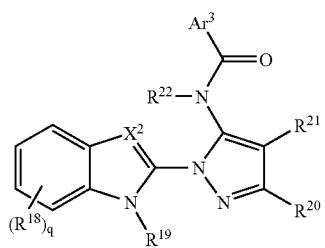

where $X^2$ is N;

$Ar^3$ is aryl, alkyl, cycloalkyl, heteroaryl or COO-alkyl, and is optionally substituted with halo, pseudohalo, alkyl or alkoxy;

q is 0;

$R^{20}$ is alkyl;

$R^{21}$ and $R^{22}$ are hydrogen; and $R^{19}$ is hydrogen, alkyl or aralkyl, optionally substituted with halo or pseudohalo.

In another embodiment, the compounds have Formula V wherein $Ar^3$ is phenyl, methyl, thienyl, cyclopropyl or COOEt, and is optionally substituted with fluoro, chloro, tert-butyl or methoxy. In another embodiment, the compounds have Formula V wherein $Ar^3$ is 4-fluorophenyl, methyl, 2-thienyl, cyclopropyl, COOEt, 4-chlorophenyl, 4-tert-butylphenyl or 4-methoxyphenyl.

In another embodiment, the compounds have Formula V wherein $R^{20}$ is methyl.

In another embodiment, the compounds have Formula V wherein $R^{19}$ is hydrogen, methyl or 2-fluorobenzyl.

In another embodiment, the compounds of Formula V are:

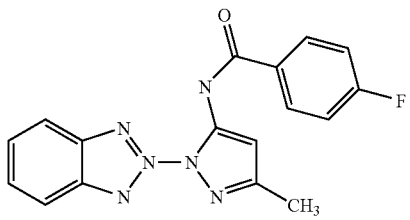

-continued

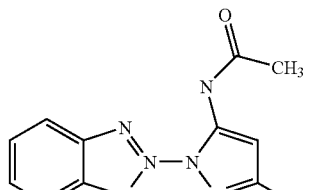

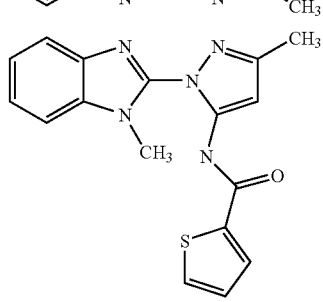

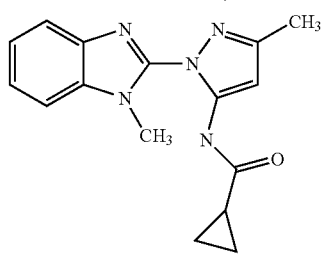

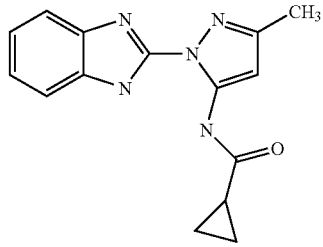

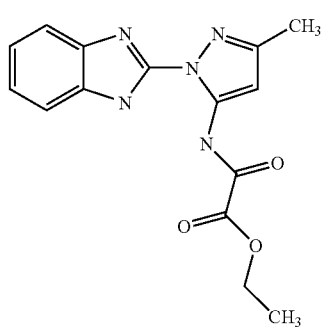

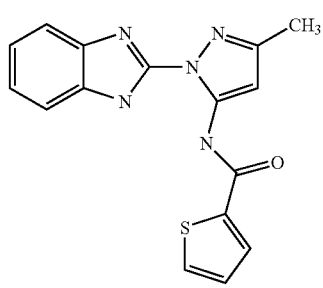

-continued

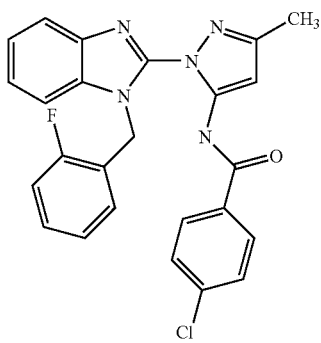

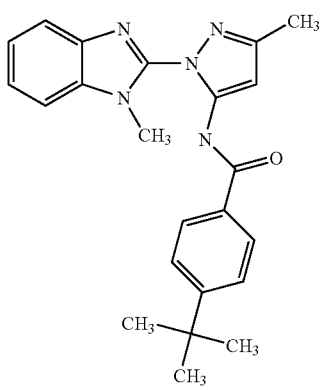

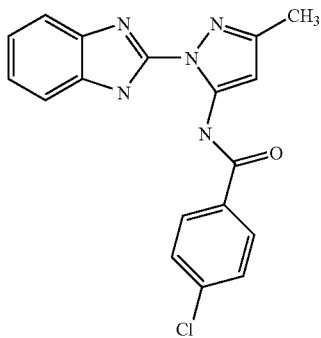

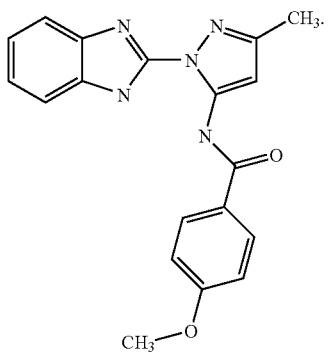

In another embodiment, the compounds for use in the compositions and methods provided herein have Formula VI:

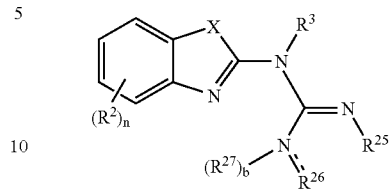

where X is O or S;

$R^2$ is alkyl;

n is 0 or 1;

$R^3$ is hydrogen;

$R^{25}$ and $R^{26}$, together with the atoms to which they are attached, form a heterocyclyl or heteroaryl ring;

b is 1 when the N—$R^{26}$ bond is a single bond;

b is 0 when the N—$R^{26}$ bond is a double bond; and $R^{27}$ is hydrogen or alkyl;

where X, $R^2$, $R^3$, $R^{25}$, $R^{26}$ and $R^{27}$ are each independently unsubstituted or substituted with one or more substituents, in one embodiment one, two or three substituents, each independently selected from $Q^1$.

In another embodiment, the compounds have Formula VI where $R^2$ is methyl.

In another embodiment, the compounds have Formula VI where $R^{25}$ and $R^{26}$, together with the atoms to which they are attached, form a imidazolidinone, pyrimidine, pyrimidinone or triazine ring system, optionally fused to an aryl or cycloalkyl ring, and optionally substituted with alkyl, alkoxycarbonylalkylidene, hydroxycarbonylalkyl, alkoxyalkyl, aralkyl, carboxy, alkoxycarbonylalkyl, arylaminocarbonyl or heterocyclylalkyl. In another embodiment, the compounds have Formula VI where $R^{25}$ and $R^{26}$, together with the atoms to which they are attached, form one of the following ring systems:

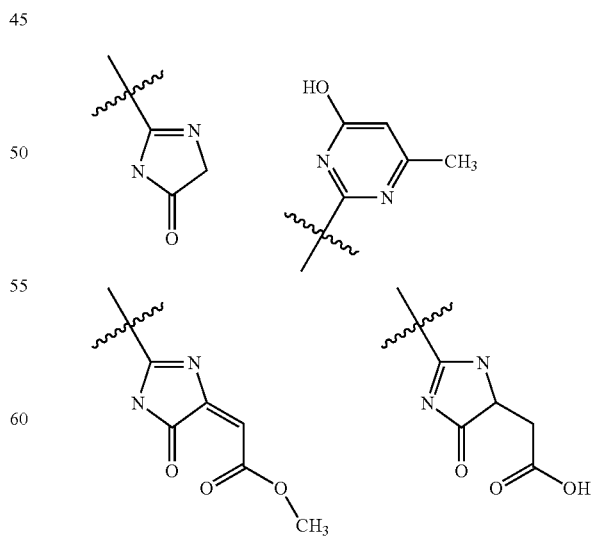

-continued
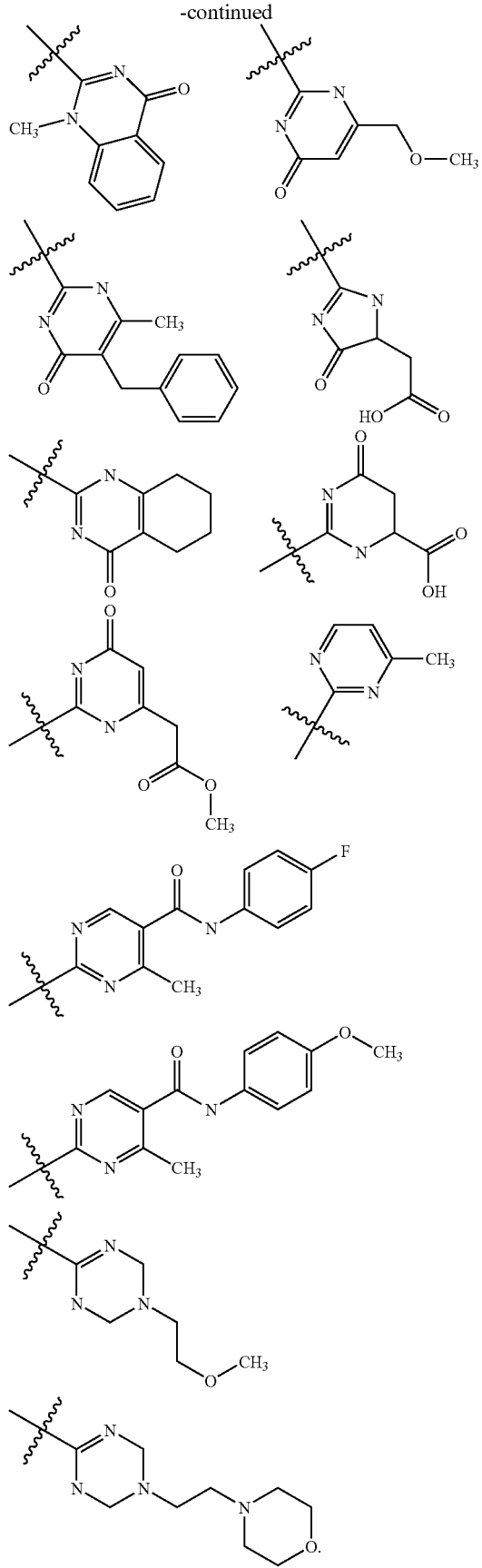
In another embodiment, the compounds have Formula VI where $R^{27}$ is hydrogen or methyl.
In another embodiment, the compounds of Formula VI are:
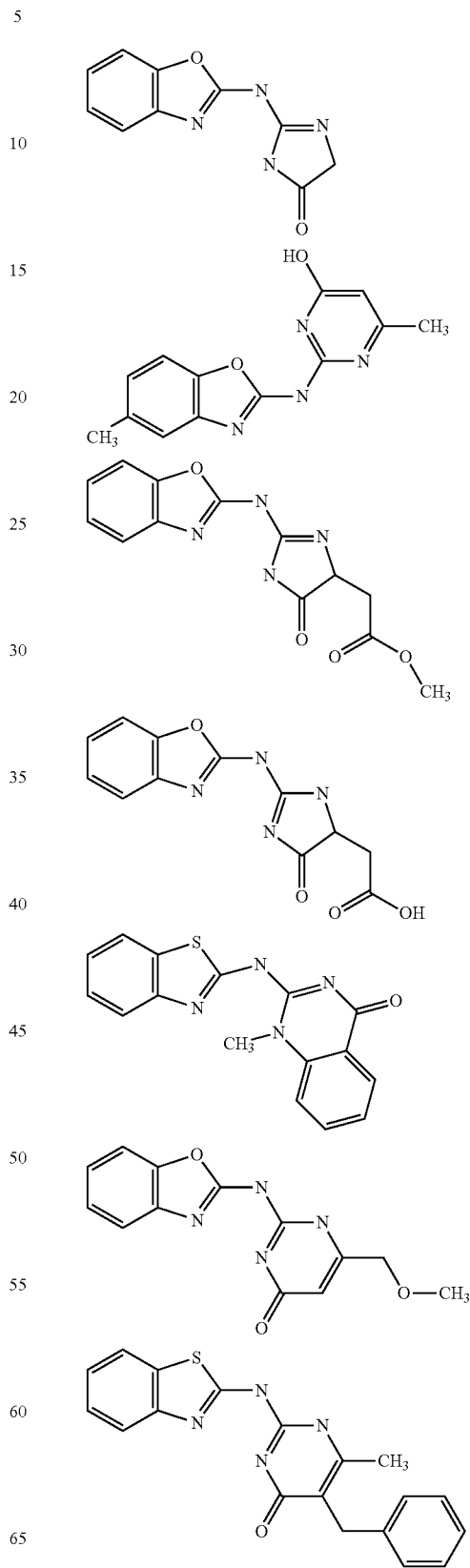

-continued

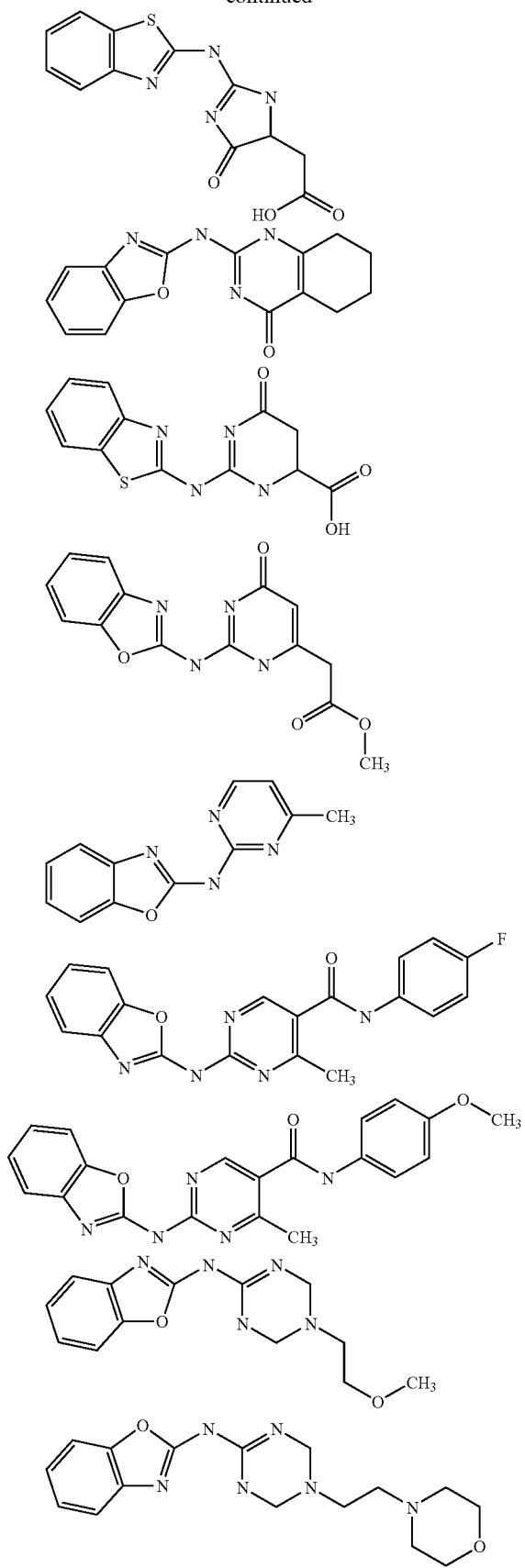

In another aspect, compounds according to Formula VII:

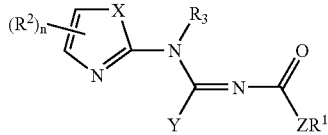

are provided for use in the compositions and methods described herein,
where X is O, S or NR,
where R is hydrogen or alkyl;
Y is NRR or OH;
Z is a direct bond or NR;
$R^1$ is allyl, alkenyl, alkynyl, cycloalkyl, aryl, heteroaryl, aralkyl, or aralkenyl;
$R^2$ is halo, pseudohalo, alkyl, cycloalkyl, alkoxy, aryl, aralkoxy, heteroaryl, aralkyl, or heteroaralkyl;
n is 0, 1, or 2;
$R^3$ is hydrogen or alkyl; and
where X, Y, Z, $R^1$, $R^2$ and $R^3$ are each independently unsubstituted or substituted with one or more substituents, in one embodiment one, two or three substituents, each independently selected from $Q^1$.

Figure 2:
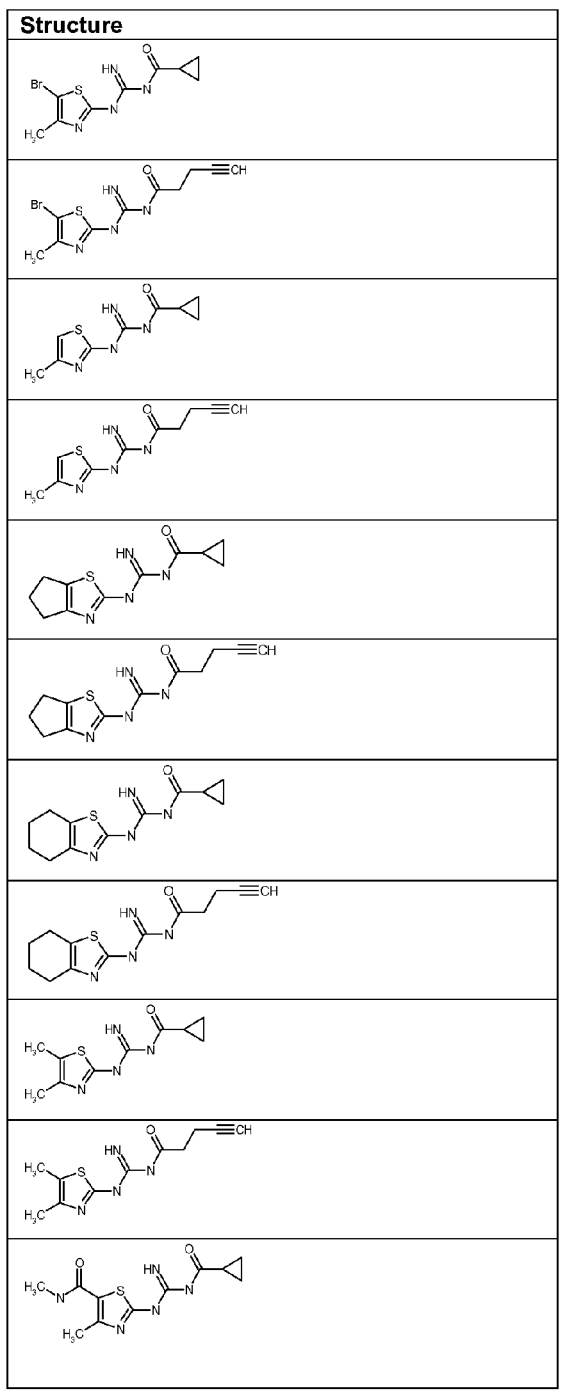
FIG. 2 sets forth the structures for certain compounds according to Formula VII, as described herein.
Figure 2:
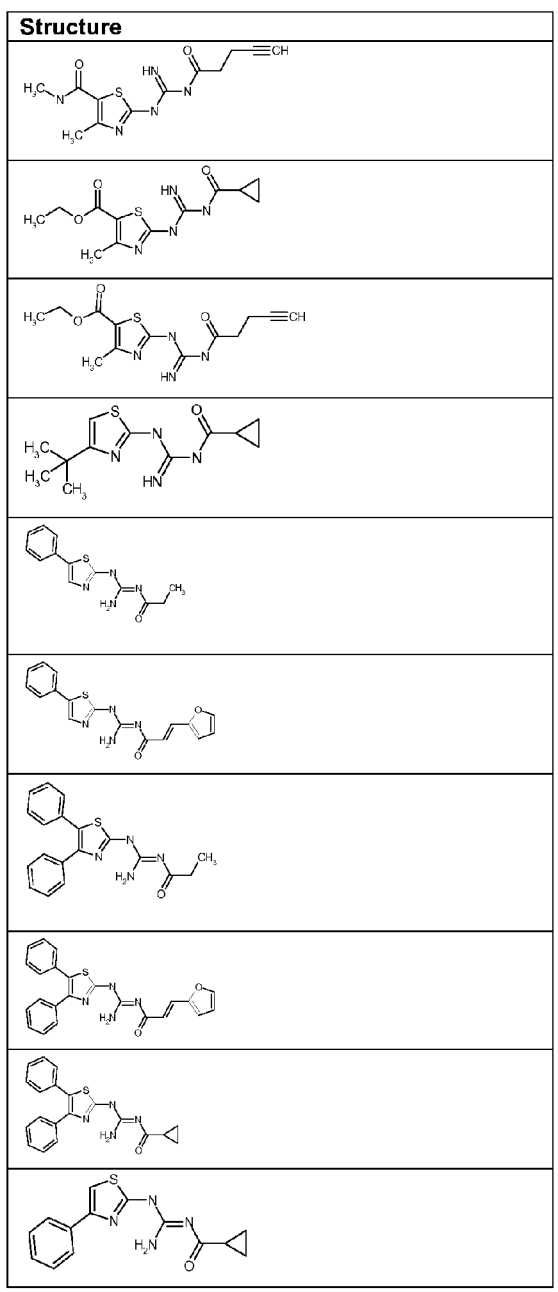
Figure 2:
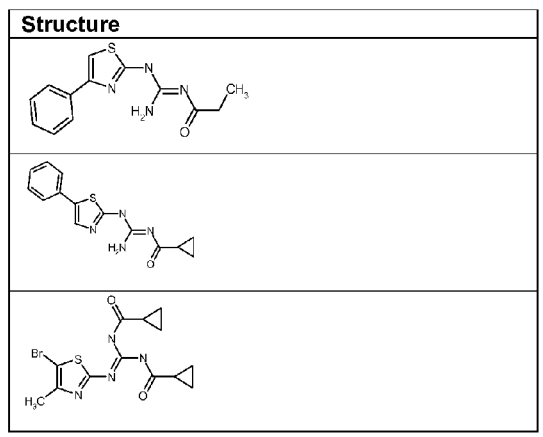

In one embodiment, Z is a direct bond.
In another embodiment, Y is $NH_2$.
In one embodiment, $R_3$ is H.
In one embodiment, $R^1$ is substituted with one or more substituents independently selected from aryloxy, aryl, heteroaryl, halo, pseudohalo, alkyl, alkoxy, cycloalkyl, alkoxycarbonyl, and hydroxycarbonyl.
In another embodiment, the compounds have Formula VII where R is hydrogen.
In another embodiment, the compounds have Formula VII where n is 0 or 1.
In another embodiment, the compounds have Formula VII where X is S, O or NH.
In another embodiment, the compounds have Formula VII where Z is a direct bond or NH.
In another embodiment, when n=2 and the $R^2$ groups substitute adjacent carbon atoms, the $R^2$ groups can form a fused cycloalkyl group (e.g., cyclopentyl, cyclohexyl group) together with the C atoms they substitute.
In another embodiment, the compounds have Formula VII where $R^1$ is ethyl, cyclopropyl or 2-(2-furyl)-ethenyl.
In another embodiment, $R^2$ is phenyl.
In another embodiment, when n=2 and the $R^2$ groups substitute adjacent carbon atoms, the $R^2$ groups are both phenyl.
Particular compounds according to Formula VII are also set forth in FIG. 2.

C. Preparation of the Compounds

The compounds for use in the compositions and methods provided herein may be obtained from commercial sources (e.g., Aldrich Chemical Co., Milwaukee, Wis.), may be prepared by methods well known to those of skill in the art, or may be prepared by the methods shown herein. One of skill in the art would be able to prepare all of the compounds for use herein by routine modification of these methods using the appropriate starting materials.
Certain of the compounds provided herein may be made by the synthetic route shown below. Briefly, aryl amines or heteroaryl amines are converted to 1 using the corresponding nitrile. Compound 1 can also be synthesized in other ways including from aryl halides or heteroaryl halides using the corresponding guanidinium salt. Compound 1 is treated with acyl halides or anhydrides to make the corresponding acylated compound 2, which can be converted to the corresponding amide 3 by reaction with ammonia. Compound 1 is converted to a five membered heterocyclic compound 4 by reagent 10 and a suitable base such as pyridine or dimethyl amino pyridine in dichloromethane. Compound 1 is converted to a six membered heterocyclic compound 5 by reagent 11 or reagent 12 and a suitable base. Compound 1 is converted to six membered heterocyclic compound 6 by reagent 13 and a base. Compound 1 is converted to six membered heterocyclic compound 7 by reagent 14 with a suitable base and solvent.

Aryl amine or a heteroaryl amine is converted to compound 8 by reagent 14 with a suitable base and solvent. Compound 8 can be further treated with ammonia to make the corresponding imine, which is acylated to yield compound 9.

Other compounds provided herein can be prepared by the scheme shown below. Briefly, heteroaryl 15 is treated with hydrazine and base in a suitable solvent to synthesize hydrazine derivative 16. 16 is converted to imine 17 by treatment with carbonyl compound 18.

Other compounds provided herein may be prepared using the general schemes set forth in the Examples, below. For example, Methods 1-4 as shown in Example 2 can be used to prepare various examples of compound 1, which can be converted to certain compounds provided herein (e.g., according to Formula I) using the methods set forth in Method L. Similarly, Methods 5 and 6 as shown in Example 2 can be used to prepare compounds according to Formula VII.

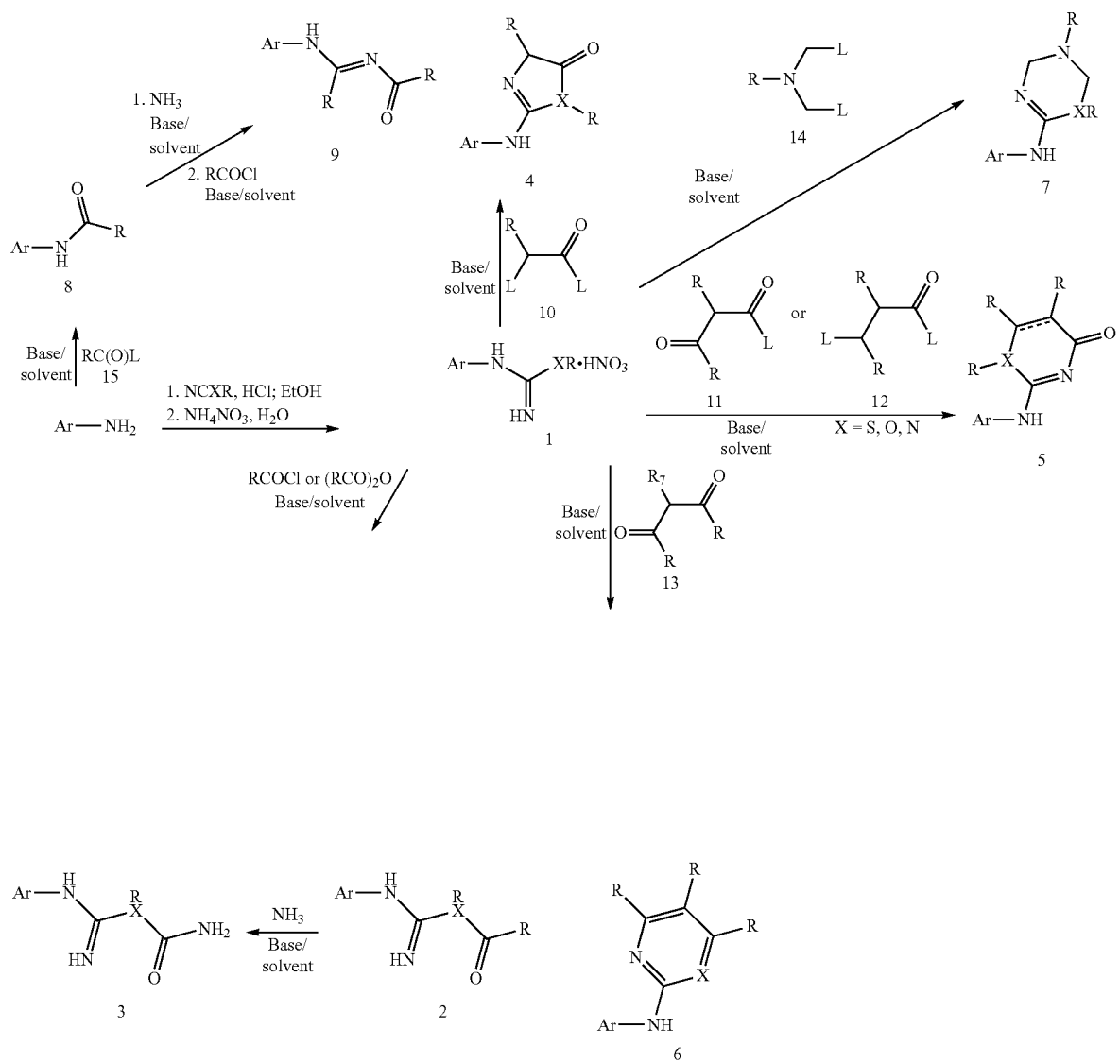

L = Leaving groups or electrophiles
e.g. halides, alkyl or aryl carboxylates, sulfonates, etc.,
Ar = aryl, or heteroary

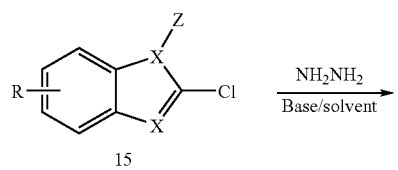

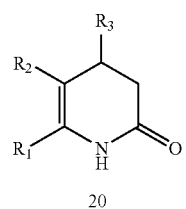

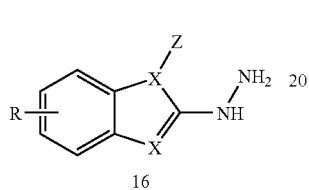

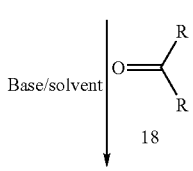

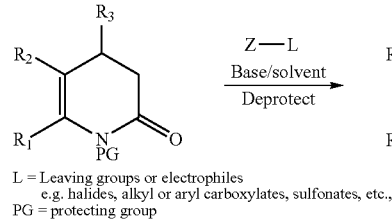

L = Leaving groups or electrophiles
  e.g. halides, alkyl or aryl carboxylates, sulfonates, etc.,
PG = protecting group Other compounds provided herein may be synthesized according to the following scheme. Briefly, aldehyde 21 and methyl acetate undergo a condensation reaction to yield an unsaturated ester, which is hydrolyzed to the corresponding acid by a suitable base. The acid can then be converted directly to unsaturated carbonyl 23 by treatment with protic acid. The acid can also be converted to the corresponding acid chloride 22 by treatment with thionyl chloride, the acid chloride 22 can then undergo a Friedel Crafts acylation with 24 to form an unsaturated carbonyl 23.

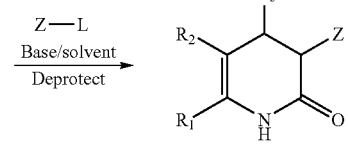

X = S, O, or N

Further compounds provided herein may be prepared by the scheme shown below. Briefly, amine 19 is acylated by treatment with acetic anhydride and base. This acyl intermediate product is then treated with a suitable aldehyde and Lewis or protic acid to synthesize lactam 20. The nitrogen of the lactam 20 can be protected and the carbon adjacent to the carbonyl functionalized by standard substitution reactions.

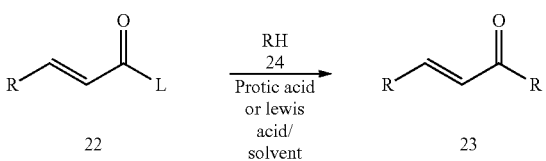

L = OH or Cl

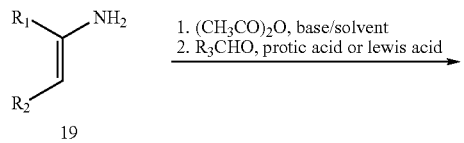

Further compounds provided herein may be synthesized according to the scheme shown below. Briefly, hydrazine 24 is converted to amine 25 by treating it with amide 28 and base. The amine 25 can be acylated with 29 to yield 26. Hydrazine 24 is converted to pyrrole 27 by treatment with a dicarbonyl compound 30.

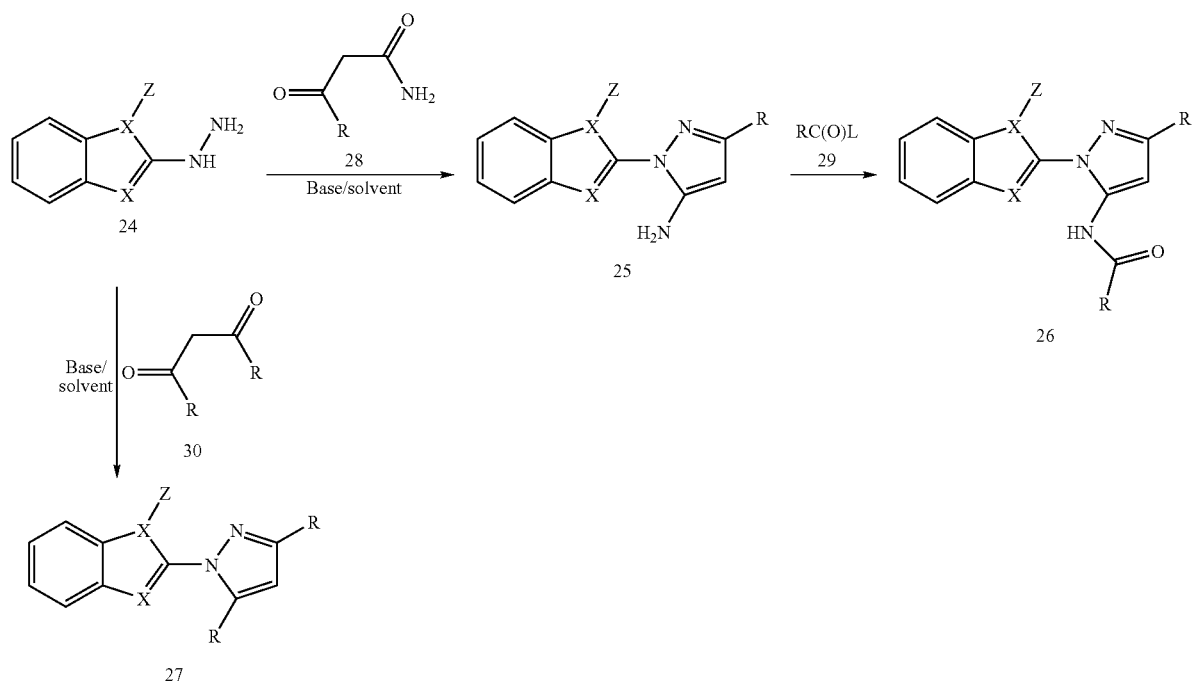

X = S, O, or N
L = Leaving groups or electrophiles e.g. halides, alkyl or aryl carboxylates, sulfonates, etc.,

D. Formulation of Pharmaceutical Compositions

The pharmaceutical compositions provided herein contain therapeutically effective amounts of one or more of the compounds provided herein that are useful in the treatment or amelioration of one or more of the symptoms of diseases or disorders associated with α-synuclein toxicity, α-synuclein fibril formation, or in which α-synuclein fibril formation is implicated, and a pharmaceutically acceptable carrier. Diseases or disorders associated with α-synuclein toxicity and/or α-synuclein fibril formation include, but are not limited to, Parkinson's disease and Lewy body dementia. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats or ameliorates one or more of the symptoms of diseases or disorders associated with α-synuclein toxicity, α-synuclein fibril formation or in which α-synuclein toxicity and/or fibril formation is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein (see, e.g., EXAMPLE 1) and in U.S. patent application Ser. No. 10/826,157, filed Apr. 16, 2004, and U.S. Patent Application Publication No. 2003/0073610, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with α-synuclein fibril formation or in which α-synuclein fibril formation is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent from with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating α-synuclein fibril formation, or for treatment or amelioration of one or more symptoms of diseases or disorders in which α-synuclein fibril formation, is implicated, within the packaging material, and a label that indicates that the compound or composition, or pharmaceutically acceptable derivative thereof, is used for modulating α-synuclein fibril formation, or for treatment or amelioration of one or more symptoms of diseases or disorders in which α-synuclein fibril formation is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which α-synuclein fibril formation is implicated as a mediator or contributor to the symptoms or cause.

8. Sustained Release Formulations

Also provided are sustained release formulations to deliver the compounds to the desired target (i.e. brain or systemic organs) at high circulating levels (between $10^{-9}$ and $10^{-4}$ M). In a certain embodiment for the treatment of Alzheimer's or Parkinson's disease, the circulating levels of the compounds is maintained up to $10^{-7}$ M. The levels are either circulating in the patient systemically, or in one embodiment, present in brain tissue, and in a another embodiments, localized to the amyloid or α-synuclein fibril deposits in brain or other tissues.

It is understood that the compound levels are maintained over a certain period of time as is desired and can be easily determined by one skilled in the art. In one embodiment, the administration of a sustained release formulation is effected so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809;

3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

E. Evaluation of the Activity of the Compounds

The activity of the compounds provided herein as modulators of α-synuclein toxicity may be measured in standard assays (see, e.g., U.S. patent application Ser. No. 10/826,157, filed Apr. 16, 2004; U.S. Patent Application Publication No. 2003/0073610; and EXAMPLE 1 herein). The activity may be measured in a whole yeast cell assay using 384-well screening protocol and an optical density measurement. Expression of human α-synuclein in yeast inhibits growth in a copy-number dependent manner (see, e.g., Outeiro, et al. (2003) *Science* 302(5651):1772-5). Expression of one copy of α-syn::GFP has no effect on growth, while two copies result in complete inhibition. The cessation of growth is accompanied by a change in α-syn::GFP localization. In cells with one copy, α-syn::GFP associates with the plasma membrane in a highly selective manner. When expression is doubled, α-synuclein migrates to the cytoplasm where it forms large inclusions that are similar to Lewy bodies seen in diseased neurons.

The compounds provided herein were screened in this assay for α-synuclein toxicity rescue. Briefly, the humanized strain is exposed to compounds in 384-well plates under conditions that induce α-synuclein expression. After incubation for 48 hours, growth is measured. Compounds that inhibit toxicity will restore growth and are detected as an increase in turbidity ($OD_{600}$).

F. Methods of Use of the Compounds and Compositions

Provided herein are methods to inhibit or prevent α-synuclein toxicity and/or fibril formation, methods to inhibit or prevent α-synuclein fibril growth, and methods to cause disassembly, disruption, and/or disaggregation of α-synuclein fibrils and α-synuclein-associated protein deposits.

In certain embodiments, the synuclein diseases or synucleinopathies treated or whose symptoms are ameliorated by the compounds and compositions provided herein include, but are not limited to diseases associated with the formation, deposition, accumulation, or persistence of synuclein fibrils, including α-synuclein fibrils. In certain embodiments, such diseases include Parkinson's disease, familial Parkinson's disease, Lewy body disease, the Lewy body variant of Alzheimer's disease, dementia with Lewy bodies, multiple system atrophy, and the Parkinsonism-dementia complex of Guam.

In practicing the methods, effective amounts of the compounds or composition provided herein are administered. Such amounts are sufficient to achieve a therapeutically effective concentration of the compound or active component of the composition in vivo.

G. Combination Therapy

The compounds and compositions provided herein may also be used in combination with other active ingredients. In another embodiment, the compounds may be administered in combination, or sequentially, with another therapeutic agent. Such other therapeutic agents include those known for treatment or amelioration of one or more symptoms of α-synuclein diseases. Such therapeutic agents include, but are not limited to, donepezil hydrochloride (ARICEPT®), rivastigmine tartrate (EXELON®), tacrine hydrochloride (COGNEX®) and galantamine hydrobromide (REMINYL®).

The following examples are provided for illustrative purposes only and are not intended to limit the scope of the invention.

EXAMPLE 1

α-Synuclein (aS) Screening

Yeast Strains

Parental W303: MAT a/α ade2-1/ade2-1 his3-11,15/his3-11,15 leu2-3,112/leu2-3,112
trp1-1/trp1-1 ura3-1/ura3-1 can1-100/can1-100

Phenotype: Requires adenine, histidine, leucine, tryptophan, and uracil for growth. Resistant to canavanine.

Fx-109: MAT a/α ade2-1/ade2-1 his3-11,15/his3-11,15 leu2-3,112/leu2-3,112
trp1-1/trp1-1    GALp-aS-GFP::TRP1/GALp-aS-GFP::TRP1 ura3-1/ura3-1
GALp-aS-GFP::URA3/GALp-aS-GFP::URA3    can1-100/can1-100    pdr1::KanMX/pdr1::KanMX    erg6::KanMX/erg6::KanMX Phenotype: Unable to grow on galactose due to expression of aS. Requires histidine, leucine, and adenine for growth. Resistant to canavanine and kanamycin. Hypersensitive to drugs.

Media and Reagents

Based on the genotype of the strain to be tested, choose the appropriate supplementation for the synthetic media. Strains containing integrated constructs (eg, aS) should be grown in medium which maintains selection for the construct (see below). CSM (Qbiogene) is a commercially-available amino acid mix for growing *Saccharomyces cerevisiae*. It can be obtained lacking one or more amino acids as required. For the aS and control strains, media lacking tryptophan and uracil (-Trp-Ura) should be used (available from Qbiogene, Inc., Carlsbad, Calif.).

To make liquid synthetic medium, mix the components listed in Table 1. After the components have dissolved, sterilize by filtration (Millipore Stericup Cat#SCGPU11RE) into a sterile bottle.

TABLE 1

| | | | | | |
|---|---|---|---|---|---|
| Synthetic Complete Medium | | | | | |
| Component | Vendor | Catalogue # | Size | Amount per L | Final Conc. |
| Yeast Nitrogen Base without amino acids | Difco | 291920 | 2 kg | 6.7 g | 0.67% (w/v) |

TABLE 1-continued

Synthetic Complete Medium

| Component | Vendor | Catalogue # | Size | Amount per L | Final Conc. |
|---|---|---|---|---|---|
| Carbon source: one of glucose, galactose, raffinose-see Table 2 | See below | See below | See below | 20 g | 2% (w/v) |
| CSM: strain determines type-see Table 3 | Qbiogene | See below | See below | ~0.8 g (according to manufacturer) | |
| MilliQ Water | — | — | | 1 L | — |

TABLE 2

Carbon Sources

| | | | | | |
|---|---|---|---|---|---|
| Glucose (also known as dextrose) | Fisher | D16-10 | 10 kg | 20 g | 2% (w/v) |
| Galactose | SIGMA | G-0750 | 1 kg | 20 g | 2% (w/v) |
| Raffinose | Difco | 217410 | 100 g | 20 g | 2% (w/v) |

TABLE 3

CSM

| | | | | | |
|---|---|---|---|---|---|
| CSM-Trp-Ura for aS and control strain | Qbiogene | 4520-522 | 100 g | 0.72 g | See Qbiogene web page |
| CSM for the parental strain | Qbiogene | 4500-022 | 100 g | 0.79 g | See Qbiogene web page |

384-Well Screening Protocol Using Optical Density
Day 1
Innoculate an appropriate volume of SRaffinose-Trp-Ura medium with Fx-109 strain.
Incubate with shaking at 30° C. overnight until cells reach log or mid-log phase ($OD_{600}$ 0.5-1.0; 0.1 OD600 corresponds to ~1.75×10 E6 cells).
Day2
Spin down cells at room temperature, remove medium, and resuspend in an equivalent volume of SGalactose-Trp-Ura medium. Measure the $OD_{600}$ and dilute cells to 0.001. Robotically transfer 30 μl of cell suspension (MicroFill, Biotek) to each well of a 384-well plate (NUNC 242757).
Add 100 nl drug in DMSO (Cybio) to each well (final conc. 17 μg/ml drug and 0.333% DMSO)
For the positive controls add glucose to final concentrations of 0.1% and 1%. (Note: daunorubicin may be an additional control based on Biochem J. 368:131-6, 2002, but we have not tested it.)
Incubate plates at 30° C. without shaking in a humidified chamber for 48 hours.
Day 4
Read $OD_{650}$ (Envision, Perkin Elmer) and also visually inspect wells for growth of yeast culture.
Results
The compounds provided herein were assayed as described above and showed an MRC (minimum rescue concentration) of less than about 300 μM.

EXAMPLE 2

Certain compounds according to Formulae I-IX can be prepared as described below.

Preparation of Guanidines
Method 1

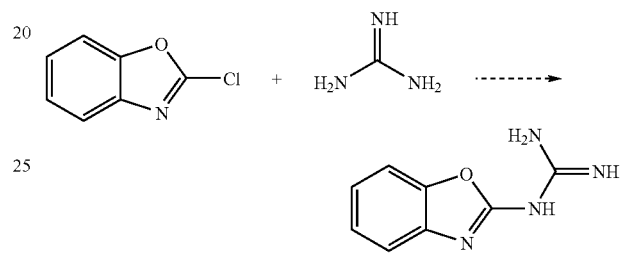

A mixture of guanidine-carbonate (22 g, 120 mmol) and 2-chlorobenzoxazole (7 ml, 60 mmol) in a solution of N,N-diisopropylethylamine (45 ml, 259 mmol) and DMF (100 ml) was heated at 60° C. overnight. It was evaporated and treated with water (100 ml). The ppt was collected, washed with ether and dried. Yield: 9.3 g (88%) of desired intermediate product, off-white solid. Purity: 95%.
Method 2

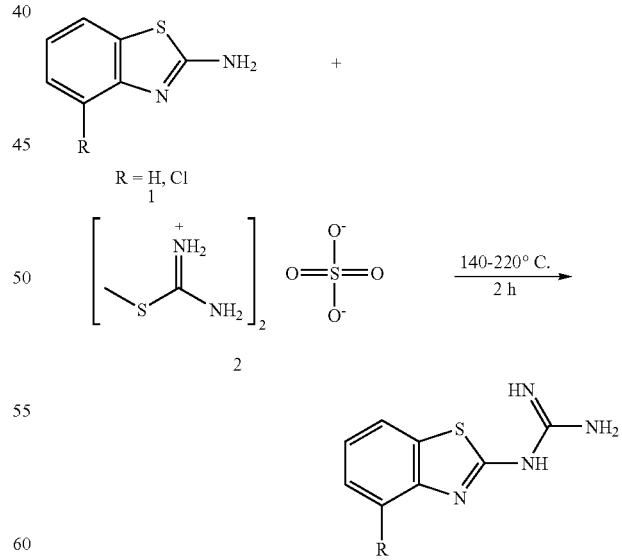

2-Aminobenzothiazole 1 (1 eq) and 2-methyl-2-thiopseudourea sulfate (1 eq) were mixed in a vial and heated in oil bath above the melting point of the mixture (140-220° C.) for 2 h at stirring. The mixture was allowed to cool, thoroughly triturated with hot MeOH, filtered, and washed with MeOH. The resulting grey solid product (apparently, in a mixed sulfate with S-methyl-2-thiopseudourea form), which is insoluble in organic solvents, was mixed with saturated aqueous $Na_2CO_3$ and EtOAc, the water layer was extracted with EtOAc, the combined organic extracts were dried with $MgSO_4$, and concentrated. The resulting crude product was purified by recrystallization from ether-hexanes or EtOAc-hexanes.

% Yield, 25-60

Method 3

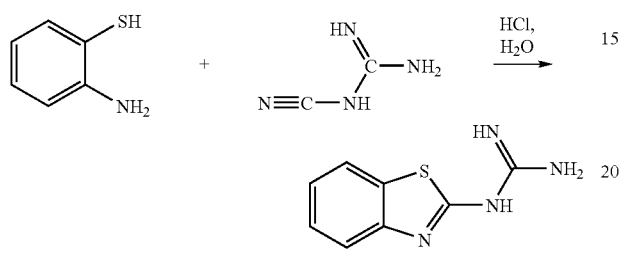

Reference: Krommer, Prietzel, Weiss. 2-Benzothiazolylguanidine. Ger. Offen. (1975), 9 pp. DE 2418913 19751030 CAN 84:31048

2-Aminothiophenol, 12.5 g (0.10 mol) and water, 30 ml, were placed in a 0.25 L round-bottom flask with efficient magnetic stirrer. Concentrated aqueous HCl, 20 ml (0.22 mol) was added slowly (in ~1-2 min) at stirring. The yellow aminothiophenol dissolved, and white precipitate of its salt formed. The mixture was heated to 70° C., and dicyandiamide, 8.4 g (0.10 mol) was added in small portions (~10 min) at stirring.

The resulting suspension was refluxed for 20-30 min (oil bath temp 120-130° C.), then the heating was removed, the mixture allowed to cool to 60-80° C., and the solution of NaOH, 8.4 g (0.21 mol) in water, 8.4 ml, was added dropwise by pipette (slight heating observed).

The mixture was allowed to cool down, filtered, washed with water (4×20 ml), and dried under oil pump vacuum for 2 days (the solid holds nearly equal amount of water and dries very slowly). The dried light-grey solid of 2-benzothiazolylguanidine, 18.1 g (94%) was pure by HPLC and NMR.

Method 4

Stage 1

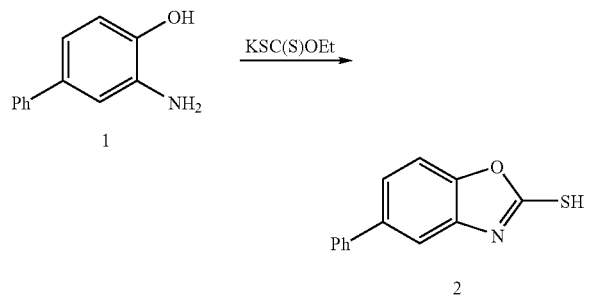

4-Phenyl-2-aminophenol, 11.4 mmol (2.10 g) was dissolved in ethanol, 30 ml, and added potassium ethyl xanthate, 11.4 mmol (1.82 g). The reaction mixture was refluxed overnight, cooled, and excess of ethanol was distilled off, then the reaction mixture was poured into crushed ice. The pH was adjusted to 5 by the addition of acetic acid. The white precipitate formed was filtered and dried to give the crude 5-phenylbenzo[d]oxazole-2-thiol, 2.32 g (90%) that was directly used in the next step without any purification.

Stage 2

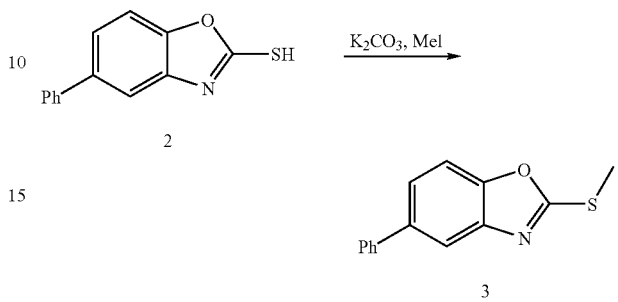

5-Phenylbenzo[d]oxazole-2-thiol 2, 10 mmol (2.32 g) was dissolved in dry acetone, 40 ml, and anhydrous potassium carbonate, 12 mml (1.68 g) was added. To this reaction mixture, methyl iodide, 12 mmol (1.7 ml) was added and the mixture was refluxed at in a 70° C. bath overnight. The reaction was cooled; excess of acetone was distilled out and the residue was extracted with ethyl acetate. The combined organic layer was washed with water followed by brine water. The organic layer was dried with anhydrous sodium sulfate, and evaporation of the solvent yielded a crude product. The crude product obtained was purified by column chromatography, using 60-120 mesh silica and eluting with petroleum ether:ethyl acetate (96:4) to give compound 3, 2.15 g (87%) as off-white solid.

Stage 3

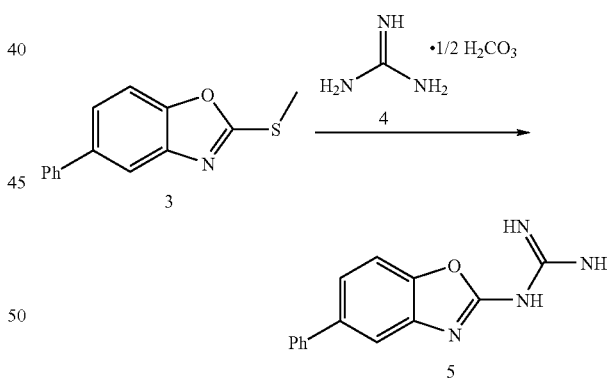

To a solution of 2-(methylthio)-5-phenylbenzo[d]oxazole 3, 9 mmol (2.15 g) in acetonitrile, 20 ml, guanidine carbonate, 18 mmol (2.11 g) and triethylamine, 36 mmol (3.60 g) was added. The reaction mixture was refluxed on an oil bath for 48 h. The reaction mixture was cooled and excess of acetonitrile was distilled out. Cold water was added and the contents were extracted with ethyl acetate (3×50 mL). The combined organic layers were washed with water followed by brine solution and dried over anhydrous sodium sulfate. Evaporation of ethyl acetate gave the crude product. The crude product obtained was purified by column chromatography over silica gel using petroleum ether: ethyl acetate [50:50] as eluent to give 0.630 g (28%) of the product as white solid.

Method 5

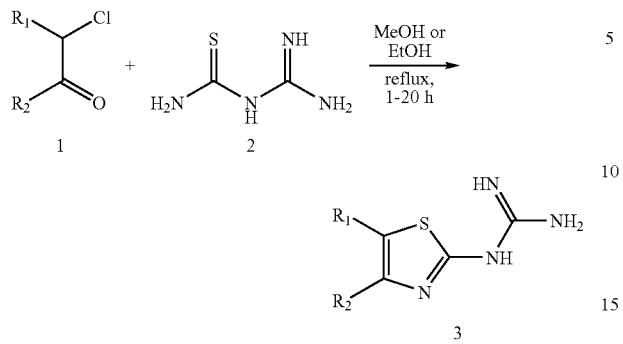

2-Chloroketone 1 (1 eq) 2-imino-4-thiobiuret 2 (1 eq) were dissolved in methanol or ethanol and refluxed until the product precipitates or until reaction is complete. The mixture was cooled down, and the product obtained by filtration or concentration was purified, if necessary, by recrystallization from methanol or chromatography on silica gel, eluent EtOAc-hexanes.

% Yield, 20-80

Method 6

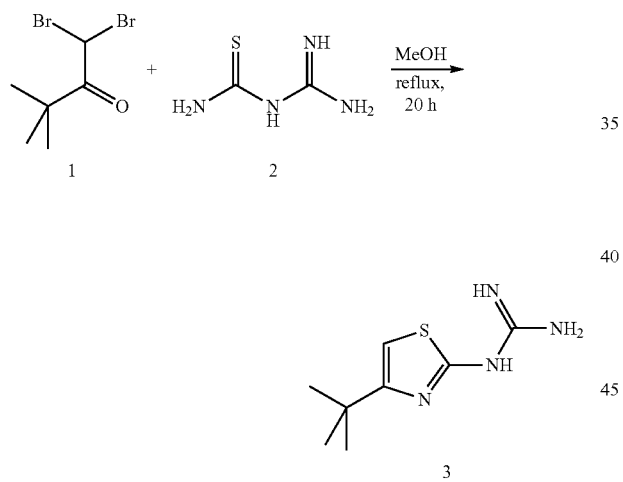

1,1-Dibromopinacolone, 10 mmol (2.58 g) and 2-Imino-4-thiobiuret, 10 mmol (1.18 g) were mixed with 20 ml methanol and refluxed overnight. The white precipitate formed was filtered off; and the filtrate was concentrated to give 0.773 g (39%) of 3 as a cream colored solid.

Preparation of Acylguanidines

Method H

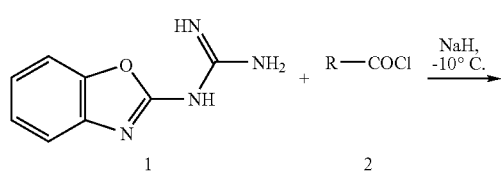

-continued

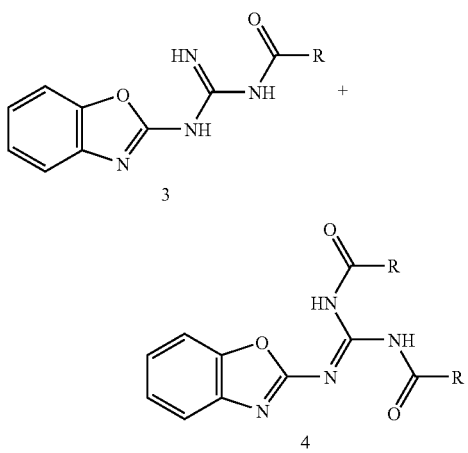

A solution of starting material 1 (1 mmol) in THF (10 ml) is cooled to −10° C. To it is added NaH (60%, 5 mmol). After 20 min stirring, a solution of acid chloride 2 (1.2 mmol) in THF (3 ml) is dropped slowly. The reaction mixture is stirred at −10° C. for 1 h, and evaporated to dry. To the residue is added water (10 ml). The mixture is shaken for a while. The insoluble solid is collected, washed with water and ether, and dried. The crude product contains ~50% of product 3, 40% of starting material 2 and no significant di-amide formed. The product is isolated by silica gel chromatography using 20% ethyl acetate in hexanes. First band is collected, evaporated to dry to give desired product 3.

% Yield, 5-67

Method I:

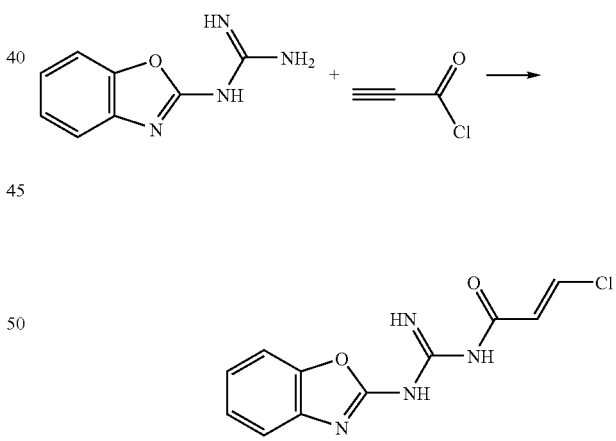

Similar to method H, Yield 8%

Method J

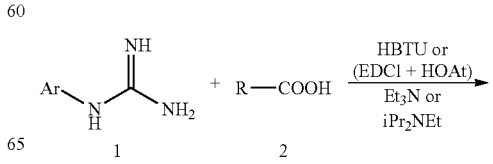

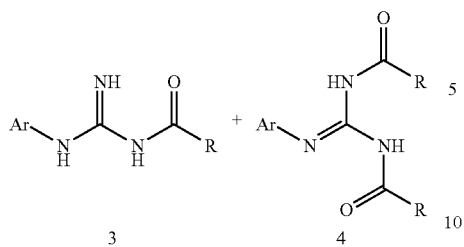

The mono-substituted guanidine 1 (1 eq), acid 2 (1 eq), HBTU (1 eq) (or: EDCI.HCl (N-(3-Dimethylaminopropyl)-N'-ethylcarbodiimide hydrochloride) (1 eq) and HOAt (1 eq.)), were dissolved in DMF, triethylamine or diisopropylethylamine (5 eq) was added, and the mixture was stirred at rt for 15-48 h. The excess of the amine was evaporated and the mixture was purified by prep-HPLC, eluent $H_2O$—$CH_3CN$-TFA, 95:5:0.05 to 5:95:0.05. When necessary, analytically pure sample was obtained by second prep-HPLC purification or recrystallization from ether/hexanes.

% Yield, 0.4-81

Method K

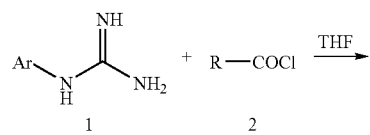

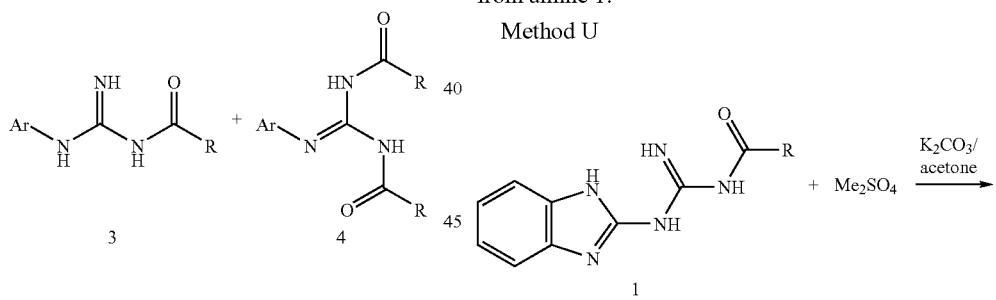

The guanidine (2 eq) was dissolved in THF, cooled to 0° C., then acid chloride (1 eq) was added dropwise in ~10 min at stirring under Ar atmosphere. Stirring continued at 0° C. for 1 h, then at rt overnight. The white solid formed was filtered off; the filtrate was concentrated under vacuum and recrystallized from MeOH or ether/hexanes.

% Yield, 10-30

Method L

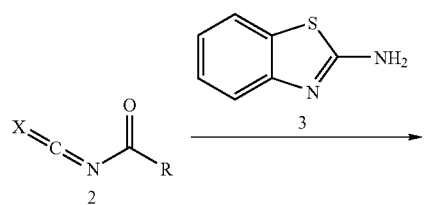

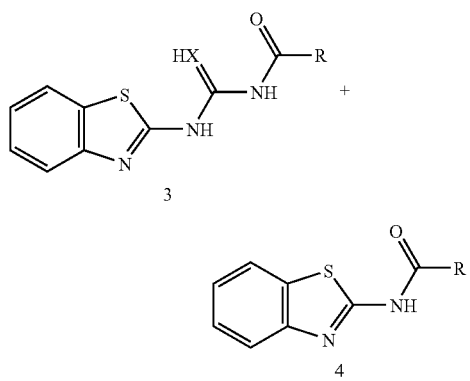

Aminobenzothiazole 1 (eq) and isocyanate or isothiocyanate 2 (1 eq) were refluxed in acetone overnight. The product was purified by chromatography on silica gel, eluent hexanes-EtOAc (100:0 to 0:100), followed by pepr-HPLC, eluent $H_2O$—$CH_3CN$-TFA (95:5:0.05 to 5:95:0.05).

% Yield, 2-13

Method T

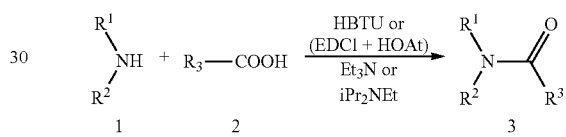

The method is the same as Method J (above), but starts from amine 1.

Method U

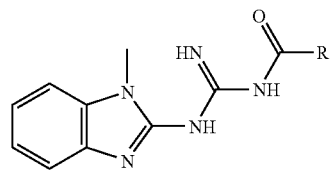

To the stirring suspension of imidazole 1 (1 eq) and $K_2CO_3$ (100 eq) in acetone-water (3:1), dimethylsulfate (7 eq) was added and the mixture was stirred overnight and purified by prep-HPLC.

% Yield, 20

EXAMPLE 3

Compounds according to Formula III can be prepared as indicated below.
Method D

General Procedure:

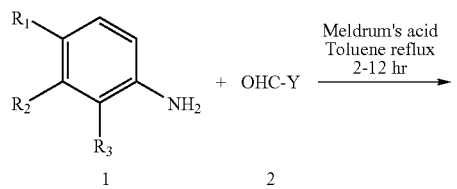

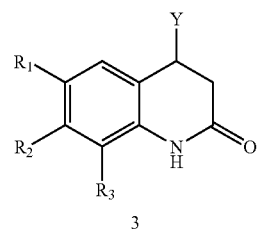

Y = aromatic, heteroaromatic, alicy (substituted or unsubstituted)

Compound 1 and compound 2 (1 equivalent) were mixed in anhydrous toluene and heated at 100° C. for 0.5 hr. Meldrum's acid (2,2-Dimethyl-[1,3]dioxane-4,6-dione) (1 equivalent) was added slowly and the solution heated at 100° C. for 2-12 hr. Upon cooling the product precipitated that was separated by filtration. The product (3) was purified by flash chromatography on silica gel (eluent, hexane:ethyl acetate, 20-50%).

% Yield, 30-80.
Method M
Stage 1

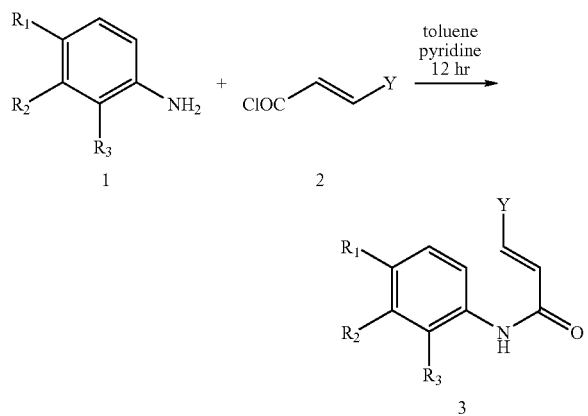

Compound 1 was dissolved in toluene and pyridine (1.2 equivalent) was added. Solution was stirred at 0° C. and compound 2 dissolved in toluene was added slowly. The solution was stirred at ambient temperature for 12 hr. Precipitated salt was separated by filtration and the filtrate was partitioned between water and ethyl acetate. The organic layer was washed with aqueous saturated sodium bicarbonate, 10% citric acid and water. Evaporation of the solvent afforded the product that was purified by crystallization from ether or hexane-ethyl acetate.

% Yield, 70-95.

Stage 2

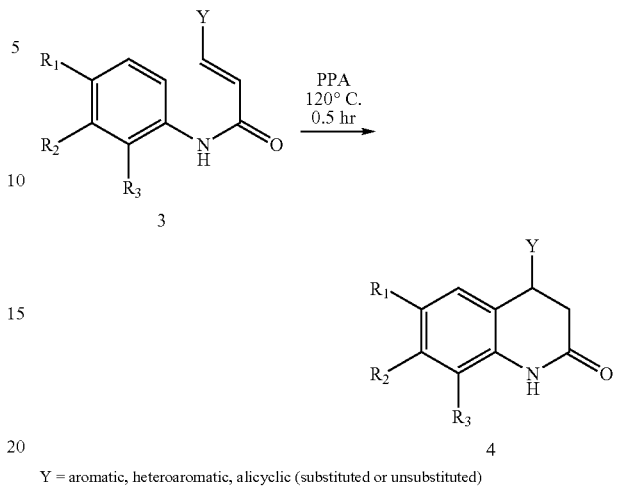

Y = aromatic, heteroaromatic, alicyclic (substituted or unsubstituted)

Compound 3 was mixed with polyphosphoric acid and heated at 120° C. for 0.5 hr. The warm solution was poured onto ice-water and the precipitate separated by filtration. The product (4) was purified by column chromatography on silica gel (eluent, hexane:ethyl acetate, 20-50%).

% Yield, 5-10.
Method N

Preparation of 3-(2-Oxo-2,3,4,6,7,8-hexahydro-1H-cyclopenta[g]quinolin-4-yl)-benzonitrile A mixture of 4-(3-Bromo-phenyl)-1,3,4,6,7,8-hexahydro-cyclopenta[g]quinolin-2-one (160 mg, 0.47 mmol) and cuprous cyanide (50.3 mg, 0.56 mmol) in N,N'-dimethylpropyleneurea was heated at 195° C. for 14 hr under an atmosphere of argon. Water was added and the product extracted with ethyl acetate. The product (12 mg) was purified by flash chromatography on silica gel (eluent, hexane:ethyl acetate, 8:2, 7:3, 6:4) followed by reverse phase HPLC (water-acetonitrile gradient, 0.05% trifluoroacetic acid, 70:30 to 10:90, 20 min, linear gradient; flow, 15 ml/min; column, Phenomenex Luna 5μ C18, 100×21.2 mm; UV 254 and 218 nm).
Method O Preparation of 4-(3-Amino-phenyl)-3,4-dihydro-1H-benzo[h]quinolin-2-one To a stirred suspension of 4-(3-Nitro-phenyl)-3,4-dihydro-1H-benzo[h]quinolin-2-one (1.0 g, 3.14 mmol) and 10% Pd/C (0.10 g) in ethanol (50 ml) was slowly added hydrazine hydrate (0.40 g, 12.6 mmol). The solution was refluxed for 2 hr and the catalyst separated by filtration. The filtrate was concentrated in vacuo to 20 ml and the solution stored in a refrigerator overnight. The precipitate was separated by filtration, washed with small amount of ethanol and vacuum dried to afford the product (0.77 g, 2.67 mmol).
Method P Preparation of 4-[3-(1H-Tetrazol-5-yl)-phenyl]-3,4-dihydro-1H-benzo[h]quinolin-2-one A mixture of 3-(2-Oxo-1,2,3,4-tetrahydro-benzo[h]quinolin-4-yl)-benzonitrile (0.50 g, 1.68 mmol), sodium azide (0.13 g, 2.0 mmol) and ammonium chloride (0.11 g, 2.01 mmol) in dimethylformamide (3.5 ml) was heated with stirring at 130° C. for 18 hr. The solvent was removed in vacuo and water was added. The solution was acidified with dilute hydrochloric acid to afford a precipitate which was separated by filtration. Crystallization from methanol afforded the title compound (0.23 g, 0.67 mmol).

Method Q

Preparation of 4-(3-Azido-phenyl)-3,4-dihydro-1H-benzo[h]quinolin-2-one 4-(3-Amino-phenyl)-3,4-dihydro-1H-benzo[h]quinolin-2-one (0.29 g, 1 mmol) was dissolved in a mixture of con. sulfuric acid (2.5 ml), water (2.5 ml) and methanol (2.5 ml). The solution was stirred at 0° C. and a solution of sodium nitrite (0.83 g, 1.2 mmol) in water (1 ml) was slowly added. The solution was stirred at 0° C. for 0.5 hr and a solution of sodium azide (0.13 g, 2 mmol) in water (1 ml) was added. The mixture was stirred at 0° C. for 0.5 hr followed by overnight stirring at ambient temperature. Water was added and the precipitate separated by filtration. The product was purified by reverse phase HPLC (0.05 g, 0.15 mmol) (water-acetonitrile gradient, 0.05% formic acid, 90:10 to 10:90, 20 min, linear gradient; flow, 15 ml/min; column, Phenomenex Luna 5μ C18, 100×21.2 mm; UV 254 and 218 nm).

Method R

Preparation of N-[3-(2-Oxo-1,2,3,4-tetrahydro-benzo[h]quinolin-4-yl)-phenyl]-acetamide A mixture of 4-(3-Amino-phenyl)-3,4-dihydro-1H-benzo[h]quinolin-2-one (0.25 g, 0.87 mmol), acetic anhydride (1 ml) and anhydrous pyridine (1 ml) was stirred at ambient temperature overnight. Water was added and the precipitate was separated by filtration. Crystallization from methanol-acetonitrile afforded the title compound (0.06 g, 0.18 mmol).

Method S

Preparation of 4-Phenyl-1H-benzo[h]quinolin-2-one

A mixture of 4-Phenyl-3,4-dihydro-1H-benzo[h]quinolin-2-one (0.55 g, 2.0 mmol) and sulfur (0.06 g, 2 mmol) was stirred at 205° C. for 0.5 hr under a nitrogen atmosphere. A second batch of sulfur (0.06 g, 2 mmol) was added and the solution stirred for 12 hr at 205° C. The product was dissolved in hot acetic acid and filtered. The clear filtrate upon cooling deposited crystals that were separated by filtration and washed with acetic acid and water followed by vacuum drying to afford the title compound (0.08 g, 0.30 mmol).

Since modifications will be apparent to those of skill in the art, it is intended that the invention be limited only by the scope of the appended claims.

What is claimed is:

1. A method of inhibiting or preventing α-synuclein toxicity and/or fibril formation, inhibiting or preventing α-synuclein fibril growth, and/or causing disassembly, disruption, and/or disaggregation of α-synuclein fibrils and α-synuclein-associated protein deposits in a patient, comprising administering to the patient a compound of Formula I:

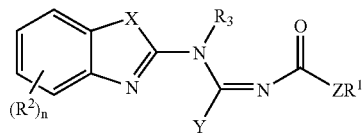

or a pharmaceutically acceptable salt thereof, wherein:

X is S;

Y is NRR'; where R is hydrogen, alkyl, alkenyl, alkynyl, cycloalkyl, heterocyclyl, aryl, heteroaryl or aralkyl, and R' is hydrogen, alkyl, alkenyl, alkynyl, cycloalkyl, heterocyclyl, aryl, heteroaryl or aralkyl;

Z is a direct bond or NR;

$R^1$ is cycloalkyl;

n is 0 to 4;

$R^2$ is selected from (i) or (ii) as follows:

(i) hydrogen, alkyl, alkenyl, alkynyl, aryl, heteroaryl, heteroarylium, cycloalkyl, heterocyclyl, $C(A)R^{110}$, halo, pseudohalo, $OR^{111}$, $S(D)_aR^{112}$, $NR^{115}R^{116}$ or $N^+R^{115}R^{116}R^{117}$; or (ii) any two $R^2$ groups, which substitute adjacent atoms on the ring, together form alkylene, alkenylene, alkynylene or heteroalkylene;

A is O, S or $NR^{125}$;

$R^{110}$ is hydrogen, alkyl, alkenyl, alkynyl, aryl, heteroaryl, heteroarylium, cycloalkyl, heterocyclyl, $C(A)R^{126}$, halo, pseudohalo, $OR^{125}$, $SR^{125}$, $NR^{127}R^{128}$ or $SiR^{122}R^{123}R^{124}$;

$R^{111}$ is hydrogen, alkyl, alkenyl, alkynyl, aryl, heteroaryl, heteroarylium, cycloalkyl, heterocyclyl, $C(A)R^{129}$, $NR^{130}R^{131}$ or $SiR^{122}R^{123}R^{124}$;

D is O or $NR^{125}$;

a is 0, 1 or 2;

when a is 1 or 2, $R^{112}$ is selected from hydrogen, alkyl, alkenyl, alkynyl, aryl, heteroaryl, heteroarylium, cycloalkyl, heterocyclyl, halo, pseudohalo, $OR^{125}$, $SR^{125}$ and $NR^{132}R^{133}$;

when a is 0, $R^{112}$ is selected from hydrogen, alkyl, alkenyl, alkynyl, aryl, heteroaryl, heteroarylium, cycloalkyl, heterocyclyl, $SR^{125}$ and $C(A)R^{129}$;

$R^{115}$, $R^{116}$ and $R^{117}$ are each independently selected from (a) and (b) as follows:

(a) hydrogen, alkyl, alkenyl, alkynyl, aryl, heteroaryl, heteroarylium, cycloalkyl, heterocyclyl, $C(A)R^{129}$, $OR^{125}$ or $NR^{132}R^{133}$; or (b) any two of $R^{115}$, $R^{116}$ and $R^{117}$ together form alkylene, alkenylene, alkynylene, or heteroalkylene, and the other is selected as in (a);

$R^{122}$, $R^{123}$ and $R^{124}$ are selected as in (i) or (ii) as follows:

(i) $R^{122}$, $R^{123}$ and $R^{124}$ are each independently hydrogen, alkyl, alkenyl, alkynyl, aryl, heteroaryl, heteroarylium, cycloalkyl, heterocyclyl, $OR^{125}$ or $NR^{132}R^{133}$; or (ii) any two of $R^{122}$, $R^{123}$ and $R^{124}$ together form alkylene, alkenylene, alkynylene, or heteroalkylene; and the other is selected as in (i);

$R^{125}$ is hydrogen, alkyl, alkenyl, alkynyl, aryl, heteroaryl, heteroarylium, cycloalkyl or heterocyclyl;

$R^{126}$ is hydrogen, alkyl, alkenyl, alkynyl, aryl, heteroaryl, heteroarylium, cycloalkyl, heterocyclyl, $OR^{125}$ or $NR^{134}R^{135}$; where $R^{134}$ and $R^{135}$ are each independently hydrogen, alkyl, alkenyl, alkynyl, aryl, heteroaryl, heteroarylium, cycloalkyl, heterocyclyl, $OR^{136}$ or $NR^{132}R^{133}$, or $R^{134}$ and $R^{135}$ together form alkylene, alkenylene, alkynylene, or heteroalkylene, where $R^{136}$ is hydrogen, alkyl, alkenyl, alkynyl, aryl, heteroaryl, heteroarylium, cycloalkyl or heterocyclyl;

$R^{127}$ and $R^{128}$ are selected as in (i) or (ii) as follows:

(i) $R^{127}$ and $R^{128}$ are each independently hydrogen, alkyl, alkenyl, alkynyl, aryl, heteroaryl, heteroarylium, cycloalkyl, heterocyclyl, $OR^{125}$, $NR^{137}R^{138}$ or $C(A)R^{139}$, where $R^{137}$ and $R^{138}$ are each independently hydrogen, alkyl, alkenyl, alkynyl, aryl, heteroaryl, heteroarylium, cycloalkyl or heterocyclyl, or together form alkylene, alkenylene, alkynylene, or heteroalkylene; and $R^{139}$ is hydrogen, alkyl, alkenyl, alkynyl, aryl, heteroaryl, heteroarylium, cycloalkyl, heterocyclyl, $OR^{140}$ or $NR^{132}R^{133}$, where $R^{140}$ is alkyl, alkenyl, alkynyl, aryl, heteroaryl, heteroarylium, cycloalkyl, or heterocyclyl; or (ii) $R^{127}$ and $R^{128}$ together form alkylene, alkenylene, alkynylene, or heteroalkylene;

$R^{129}$ is hydrogen, alkyl, alkenyl, alkynyl, aryl, heteroaryl, heteroarylium, cycloalkyl, heterocyclyl, $OR^{140}$ or $NR^{132}R^{133}$;

$R^{130}$ and $R^{131}$ are each independently hydrogen, alkyl, alkenyl, alkynyl, aryl, heteroaryl, heteroarylium, cycloalkyl, heterocyclyl or $C(A)R^{141}$, where $R^{141}$ is alkyl, alkenyl, alkynyl, aryl, heteroaryl, heteroarylium, cycloalkyl, heterocyclyl, $OR^{125}$ or $NR^{132}R^{133}$; or $R^{130}$ and $R^{131}$ together form alkylene, alkenylene, alkynylene, or heteroalkylene;

$R^{132}$ and $R^{133}$ are each independently hydrogen, alkyl, alkenyl, alkynyl, aryl, heteroaryl, heteroarylium, cycloalkyl, or heterocyclyl, or $R^{132}$ and $R^{133}$ together form alkylene, alkenylene, alkynylene, or heteroalkylene; and $R^3$ is hydrogen, alkyl, alkenyl, alkynyl, cycloalkyl, heterocyclyl, aryl or heteroaryl;

wherein Y, Z, $R^1$, $R^2$ and $R^3$ are each independently unsubstituted or substituted with one, two or three substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, hydroxycarbonylalkenyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, alkoxycarbonylalkoxy, aryloxycarbonyl, aryloxycarbonylalkyl, aralkoxycarbonyl, aralkoxycarbonylalkyl, aralkoxycarbonylalkoxy, arylcarbonylalkyl, aminocarbonyl, aminocarbonylalkyl, aminocarbonylalkoxy, alkylaminocarbonyl, alkylaminocarbonylalkyl, alkylaminocarbonylalkoxy, dialkylaminocarbonyl, dialkylaminocarbonylalkyl, dialkylaminocarbonylalkoxy, arylaminocarbonyl, arylaminocarbonylalkyl, arylaminocarbonylalokoxy, diarylaminocarbonyl, diarylaminocarbonylalkyl, diarylaminocarbonyl alkoxy, arylalkylaminocarbonyl, arylalkylaminocarbonylalkyl, arylalkylaminocarbonylalkoxy, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $-N^+R^{151}R^{152}R^{153}$, $P(R^{150})_2$, $P(=O)(R^{150})_2$, $OP(=O)(R^{150})_2$, $-NR^{160}C(=O)R^{163}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; azido, tetrazolyl or two $Q^1$ groups, which substitute atoms in a 1,2 or 1,3 arrangement, together form alkylenedioxy (i.e., $-O-(CH_2)_y-O-$), thioalkylenoxy (i.e., $-S-(CH_2)_y-O-$) or alkylenedithioxy (i.e., $-S-(CH_2)_y-S-$) where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, hydroxycarbonylalkenyl alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N⁺R¹⁵¹R¹⁵²R¹⁵³, P(R¹⁵⁰)₂, P(=O)(R¹⁵⁰)₂, OP(=O)(R¹⁵⁰)₂, —NR¹⁶⁰C(=O)R¹⁶³, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q² groups, which substitute atoms in a 1,2 or 1,3 arrangement, together form alkylenedioxy (i.e., —O—(CH₂)ᵧ—O—), thioalkylenoxy (i.e., —S—(CH₂)ᵧ—O—) or alkylenedithioxy (i.e., —S—(CH₂)ᵧ—S—) where y is 1 or 2; or two Q² groups, which substitute the same atom, together form alkylene;

R¹⁵⁰ is hydroxy, alkoxy, aralkoxy, alkyl, heteroaryl, heterocyclyl, aryl or —NR¹⁷⁰R¹⁷¹, where R¹⁷⁰ and R¹⁷¹ are each independently hydrogen, alkyl, aralkyl, aryl, heteroaryl, heteroaralkyl or heterocyclyl, or R¹⁷⁰ and R¹⁷¹ together form alkylene, azaalkylene, oxaalkylene or thiaalkylene;

R¹⁵¹, R¹⁵² and R¹⁵³ are each independently hydrogen, alkyl, aryl, aralkyl, heteroaryl, heteroaralkyl, heterocyclyl or heterocyclylalkyl;

R¹⁶⁰ is hydrogen, alkyl, aryl, aralkyl, heteroaryl, heteroaralkyl, heterocyclyl or heterocyclylalkyl; and R¹⁶³ is alkoxy, aralkoxy, alkyl, heteroaryl, heterocyclyl, aryl or —NR¹⁷⁰R¹⁷¹.

2. The method of claim 1, wherein:
X is S;
Y is NRR', where R is hydrogen or alkyl;
Z is a direct bond or NR;
R¹ is cycloalkyl;
R² is halo, pseudohalo, alkoxy or alkyl;
n is 0 or 1;
R³ is hydrogen or alkyl;
wherein Y, Z, R¹, R² and R³ are each independently unsubstituted or substituted with one, two or three substituents, each independently selected from Q¹.

3. The method of claim 1 wherein R is hydrogen.
4. The method of claim 1 wherein n is 0 or 1.
5. The method of claim 1 wherein Y is NH₂.
6. The method of claim 1 wherein Z is a direct bond or NH.

7. The method of claim 1 wherein R¹ is cycloalkyl and is unsubstituted or substituted with aryloxy, aryl, heteroaryl, halo, pseudohalo, alkyl, alkoxy, cycloalkyl, alkoxycarbonyl, hydroxycarbonyl, alkylamino, or dialkylamino.

8. The method of claim 1 wherein R¹ is cyclopropyl, cyclopropylmethyl, 2-cyclopentylethyl, cyclopentylmethyl, cyclopentyl, cyclohexyl, cyclobutyl, 2-fluorocyclopropyl, 2-methylcyclopropyl, 2-phenylcyclopropyl, 1-methyl-2,2-dichlorocyclopropyl, or 2,2-difluorocyclopropyl.

9. The method of claim 1 wherein R² is halo or alkyl.
10. The method of claim 1 wherein R² is chloro or methyl.
11. The method of claim 1 wherein R³ is hydrogen.
12. A composition, comprising a compound of Formula I:

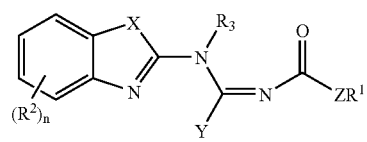

or a pharmaceutically acceptable salt thereof, wherein:
X is S;
Y is NRR'; where R is hydrogen, alkyl, alkenyl, alkynyl, cycloalkyl, heterocyclyl, aryl, heteroaryl or aralkyl, and R' is hydrogen, alkyl, alkenyl, alkynyl, cycloalkyl, heterocyclyl, aryl, heteroaryl or aralkyl;
Z is a direct bond or NR;
R¹ is cycloalkyl;
n is 0 to 4;
R² is selected from (i) or (ii) as follows:
(i) hydrogen, alkyl, alkenyl, alkynyl, aryl, heteroaryl, heteroarylium, cycloalkyl, heterocyclyl, C(A)R¹¹⁰, halo, pseudohalo, OR¹¹¹, S(D)ₐR¹¹², NR¹¹⁵R¹¹⁶ or N⁺R¹¹⁵R¹¹⁶R¹¹⁷; or
(ii) any two R² groups, which substitute adjacent atoms on the ring, together form alkylene, alkenylene, alkynylene or heteroalkylene;
A is O, S or NR¹²⁵;
R¹¹⁰ is hydrogen, alkyl, alkenyl, alkynyl, aryl, heteroaryl, heteroarylium, cycloalkyl, heterocyclyl, C(A)R¹²⁶, halo, pseudohalo, OR¹²⁵, SR¹²⁵, NR¹²⁷R¹²⁸ or SiR¹²²R¹²³R¹²⁴;
R¹¹¹ is hydrogen, alkyl, alkenyl, alkynyl, aryl, heteroaryl, heteroarylium, cycloalkyl, heterocyclyl, C(A)R¹²⁹, NR¹³⁰R¹³¹ or SiR¹²²R¹²³R¹²⁴;
D is O or NR¹²⁵;
a is 0, 1 or 2;
when a is 1 or 2, R¹¹² is selected from hydrogen, alkyl, alkenyl, alkynyl, aryl, heteroaryl, heteroarylium, cycloalkyl, heterocyclyl, halo, pseudohalo, OR¹²⁵, SR¹²⁵ and NR¹³²R¹³³;
when a is 0, R¹¹² is selected from hydrogen, alkyl, alkenyl, alkynyl, aryl, heteroaryl, heteroarylium, cycloalkyl, heterocyclyl, SR¹²⁵ and C(A)R¹²⁹;
R¹¹⁵, R¹¹⁶ and R¹¹⁷ are each independently selected from (a) and (b) as follows:
(a) hydrogen, alkyl, alkenyl, alkynyl, aryl, heteroaryl, heteroarylium, cycloalkyl, heterocyclyl, C(A)R¹²⁹, OR¹²⁵ or NR¹³²R¹³³; or
(b) any two of R¹¹⁵, R¹¹⁶ and R¹¹⁷ together form alkylene, alkenylene, alkynylene, or heteroalkylene, and the other is selected as in (a);

R$^{122}$, R$^{123}$ and R$^{124}$ are selected as in (i) or (ii) as follows:
(i) R$^{122}$, R$^{123}$ and R$^{124}$ are each independently hydrogen, alkyl, alkenyl, alkynyl, aryl, heteroaryl, heteroarylium, cycloalkyl, heterocyclyl, OR$^{125}$ or NR$^{132}$R$^{133}$; or
(ii) any two of R$^{122}$, R$^{123}$ and R$^{124}$ together form alkylene, alkenylene, alkynylene, or heteroalkylene; and the other is selected as in (i);

R$^{125}$ is hydrogen, alkyl, alkenyl, alkynyl, aryl, heteroaryl, heteroarylium, cycloalkyl or heterocyclyl;

R$^{126}$ is hydrogen, alkyl, alkenyl, alkynyl, aryl, heteroaryl, heteroarylium, cycloalkyl, heterocyclyl, OR$^{125}$ or NR$^{134}$R$^{135}$; where R$^{134}$ and R$^{135}$ are each independently hydrogen, alkyl, alkenyl, alkynyl, aryl, heteroaryl, heteroarylium, cycloalkyl, heterocyclyl, OR$^{136}$ or NR$^{132}$R$^{133}$, or R$^{134}$ and R$^{135}$ together form alkylene, alkenylene, alkynylene, or heteroalkylene, where R$^{136}$ is hydrogen, alkyl, alkenyl, alkynyl, aryl, heteroaryl, heteroarylium, cycloalkyl or heterocyclyl;

R$^{127}$ and R$^{128}$ are selected as in (i) or (ii) as follows:
(i) R$^{127}$ and R$^{128}$ are each independently hydrogen, alkyl, alkenyl, alkynyl, aryl, heteroaryl, heteroarylium, cycloalkyl, heterocyclyl, OR$^{125}$, NR$^{137}$R$^{138}$ or C(A)R$^{139}$, where R$^{137}$ and R$^{138}$ are each independently hydrogen, alkyl, alkenyl, alkynyl, aryl, heteroaryl, heteroarylium, cycloalkyl or heterocyclyl, or together form alkylene, alkenylene, alkynylene, or heteroalkylene; and R$^{139}$ is hydrogen, alkyl, alkenyl, alkynyl, aryl, heteroaryl, heteroarylium, cycloalkyl, heterocyclyl, OR$^{140}$ or NR$^{132}$R$^{133}$, where R$^{140}$ is alkyl, alkenyl, alkynyl, aryl, heteroaryl, heteroarylium, cycloalkyl, or heterocyclyl; or
(ii) R$^{127}$ and R$^{128}$ together form alkylene, alkenylene, alkynylene, or heteroalkylene;

R$^{129}$ is hydrogen, alkyl, alkenyl, alkynyl, aryl, heteroaryl, heteroarylium, cycloalkyl, heterocyclyl, OR$^{140}$ or NR$^{132}$R$^{133}$;

R$^{130}$ and R$^{131}$ are each independently hydrogen, alkyl, alkenyl, alkynyl, aryl, heteroaryl, heteroarylium, cycloalkyl, heterocyclyl or C(A)R$^{141}$, where R$^{141}$ is alkyl, alkenyl, alkynyl, aryl, heteroaryl, heteroarylium, cycloalkyl, heterocyclyl, OR$^{125}$ or NR$^{132}$R$^{133}$; or R$^{130}$ and R$^{131}$ together form alkylene, alkenylene, alkynylene, or heteroalkylene;

R$^{132}$ and R$^{133}$ are each independently hydrogen, alkyl, alkenyl, alkynyl, aryl, heteroaryl, heteroarylium, cycloalkyl, or heterocyclyl, or R$^{132}$ and R$^{133}$ together form alkylene, alkenylene, alkynylene, or heteroalkylene; and R$^3$ is hydrogen, alkyl, alkenyl, alkynyl, cycloalkyl, heterocyclyl, aryl or heteroaryl;

wherein Y, Z, R$^1$, R$^2$ and R$^3$ are each independently unsubstituted or substituted one, two or three substituents, each independently selected from Q$^1$, where Q$^1$ is halo, pseudohalo, hydroxy, oxo, thia, nitrile, nitro, formyl, mercapto, hydroxycarbonyl, hydroxycarbonylalkyl, hydroxycarbonylalkenyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, alkoxycarbonylalkoxy, aryloxycarbonyl, aryloxycarbonylalkyl, aralkoxycarbonyl, aralkoxycarbonylalkyl, aralkoxycarbonylalkoxy, arylcarbonylalkyl, aminocarbonyl, aminocarbonylalkyl, aminocarbonylalkoxy, alkylaminocarbonyl, alkylaminocarbonylalkyl, alkylaminocarbonylalkoxy, dialkylaminocarbonyl, dialkylaminocarbonylalkyl, dialkylaminocarbonylalkoxy, arylaminocarbonyl, arylaminocarbonylalkyl, arylaminocarbonylalokoxy, diarylaminocarbonyl, diarylaminocarbonylalkyl, diarylaminocarbonyl alkoxy, arylalkylaminocarbonyl, arylalkylaminocarbonylalkyl, arylalkylaminocarbonylalkoxy, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{151}$R$^{152}$R$^{153}$, P(R$^{150}$)$_2$, P(=O)(R$^{150}$)$_2$, OP(=O)(R$^{150}$)$_2$, —NR$^{160}$C(=O)R$^{163}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; azido, tetrazolyl or two Q$^1$ groups, which substitute atoms in a 1,2 or 1,3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two Q$^1$ groups, which substitute the same atom, together form alkylene; and each Q$^1$ is independently unsubstituted or substituted with one, two or three substituents, each independently selected from Q$^2$;

each Q$^2$ is independently halo, pseudohalo, hydroxy, oxo, thia, nitrile, nitro, formyl, mercapto, hydroxycarbonyl, hydroxycarbonylalkyl, hydroxycarbonylalkenyl alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{151}$R$^{152}$R$^{153}$, P(R$^{150}$)$_2$, P(=O)(R$^{150}$)$_2$, OP(=O)(R$^{150}$)$_2$, —NR$^{160}$C(=O)R$^{163}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q$^2$ groups, which substitute atoms in a 1,2 or 1,3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two Q$^2$ groups, which substitute the same atom, together form alkylene;

R$^{150}$ is hydroxy, alkoxy, aralkoxy, alkyl, heteroaryl, heterocyclyl, aryl or —NR$^{170}$R$^{171}$, where R$^{170}$ and R$^{171}$ are each independently hydrogen, alkyl, aralkyl, aryl, heteroaryl, heteroaralkyl or heterocyclyl, or R$^{170}$ and R$^{171}$ together form alkylene, azaalkylene, oxaalkylene or thiaalkylene;

R$^{151}$, R$^{152}$ and R$^{153}$ are each independently hydrogen, alkyl, aryl, aralkyl, heteroaryl, heteroaralkyl, heterocyclyl or heterocyclylalkyl;

R$^{160}$ is hydrogen, alkyl, aryl, aralkyl, heteroaryl, heteroaralkyl, heterocyclyl or heterocyclylalkyl; and R$^{163}$ is alkoxy, aralkoxy, alkyl, heteroaryl, heterocyclyl, aryl or —NR$^{170}$R$^{171}$;

and one or more of the following: donepezil hydrochloride (ARICEPT®), rivastigmine tartrate (EXELON®), tacrine hydrochloride (COGNEX®) and galantamine hydrobromide (REMINYL®).

13. A method of treating or ameliorating a synucleinopathy comprising administering to a patient a compound of Formula I:

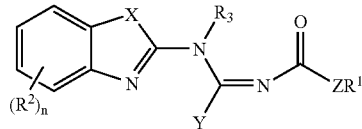

or a pharmaceutically acceptable salt thereof, wherein:
X is S;
Y is NRR'; where R is hydrogen, alkyl, alkenyl, alkynyl, cycloalkyl, heterocyclyl, aryl, heteroaryl or aralkyl, and R' is hydrogen, alkyl, alkenyl, alkynyl, cycloalkyl, heterocyclyl, aryl, heteroaryl or aralkyl;
Z is a direct bond or NR;
R$^1$ is cycloalkyl;
n is 0 to 4;
R$^2$ is selected from (i) or (ii) as follows:
(i) hydrogen, alkyl, alkenyl, alkynyl, aryl, heteroaryl, heteroarylium, cycloalkyl, heterocyclyl, C(A)R$^{110}$, halo, pseudohalo, OR$^{111}$, S(D)$_a$R$^{112}$, NR$^{115}$R$^{116}$ or N$^+$R$^{115}$R$^{116}$R$^{117}$; or
(ii) any two R$^2$ groups, which substitute adjacent atoms on the ring, together form alkylene, alkenylene, alkynylene or heteroalkylene;
A is O, S or NR$^{125}$;
R$^{110}$ is hydrogen, alkyl, alkenyl, alkynyl, aryl, heteroaryl, heteroarylium, cycloalkyl, heterocyclyl, C(A)R$^{126}$, halo, pseudohalo, OR$^{125}$, SR$^{125}$, NR$^{127}$R$^{128}$ or SiR$^{122}$R$^{123}$R$^{124}$;
R$^{111}$ is hydrogen, alkyl, alkenyl, alkynyl, aryl, heteroaryl, heteroarylium, cycloalkyl, heterocyclyl, C(A)R$^{129}$, NR$^{130}$R$^{131}$ or SiR$^{122}$R$^{123}$R$^{124}$;
D is O or NR$^{125}$;
a is 0, 1 or 2;
when a is 1 or 2, R$^{112}$ is selected from hydrogen, alkyl, alkenyl, alkynyl, aryl, heteroaryl, heteroarylium, cycloalkyl, heterocyclyl, halo, pseudohalo, OR$^{125}$, SR$^{125}$ and NR$^{132}$R$^{133}$;
when a is 0, R$^{112}$ is selected from hydrogen, alkyl, alkenyl, alkynyl, aryl, heteroaryl, heteroarylium, cycloalkyl, heterocyclyl, SR$^{125}$ and C(A)R$^{129}$;
R$^{115}$, R$^{116}$ and R$^{117}$ are each independently selected from (a) and (b) as follows:
(a) hydrogen, alkyl, alkenyl, alkynyl, aryl, heteroaryl, heteroarylium, cycloalkyl, heterocyclyl, C(A)R$^{129}$, OR$^{125}$ or NR$^{132}$R$^{133}$; or
(b) any two of R$^{115}$, R$^{116}$ and R$^{117}$ together form alkylene, alkenylene, alkynylene, or heteroalkylene, and the other is selected as in (a);
R$^{122}$, R$^{123}$ and R$^{124}$ are selected as in (i) or (ii) as follows:
(i) R$^{122}$, R$^{123}$ and R$^{124}$ are each independently hydrogen, alkyl, alkenyl, alkynyl, aryl, heteroaryl, heteroarylium, cycloalkyl, heterocyclyl, OR$^{125}$ or NR$^{132}$R$^{133}$; or
(ii) any two of R$^{122}$, R$^{123}$ and R$^{124}$ together form alkylene, alkenylene, alkynylene, or heteroalkylene; and the other is selected as in (i);
R$^{125}$ is hydrogen, alkyl, alkenyl, alkynyl, aryl, heteroaryl, heteroarylium, cycloalkyl or heterocyclyl;

$R^{126}$ is hydrogen, alkyl, alkenyl, alkynyl, aryl, heteroaryl, heteroarylium, cycloalkyl, heterocyclyl, $OR^{125}$ or $NR^{134}R^{135}$; where $R^{134}$ and $R^{135}$ are each independently hydrogen, alkyl, alkenyl, alkynyl, aryl, heteroaryl, heteroarylium, cycloalkyl, heterocyclyl, $OR^{136}$ or $NR^{132}R^{133}$, or $R^{134}$ and $R^{135}$ together form alkylene, alkenylene, alkynylene, or heteroalkylene, where $R^{136}$ is hydrogen, alkyl, alkenyl, alkynyl, aryl, heteroaryl, heteroarylium, cycloalkyl or heterocyclyl;

$R^{127}$ and $R^{128}$ are selected as in (i) or (ii) as follows:
(i) $R^{127}$ and $R^{128}$ are each independently hydrogen, alkyl, alkenyl, alkynyl, aryl, heteroaryl, heteroarylium, cycloalkyl, heterocyclyl, $OR^{125}$, $NR^{137}R^{138}$ or $C(A)R^{139}$, where $R^{137}$ and $R^{138}$ are each independently hydrogen, alkyl, alkenyl, alkynyl, aryl, heteroaryl, heteroarylium, cycloalkyl or heterocyclyl, or together form alkylene, alkenylene, alkynylene, or heteroalkylene; and $R^{139}$ is hydrogen, alkyl, alkenyl, alkynyl, aryl, heteroaryl, heteroarylium, cycloalkyl, heterocyclyl, $OR^{140}$ or $NR^{132}R^{133}$, where $R^{140}$ is alkyl, alkenyl, alkynyl, aryl, heteroaryl, heteroarylium, cycloalkyl, or heterocyclyl; or
(ii) $R^{127}$ and $R^{128}$ together form alkylene, alkenylene, alkynylene, or heteroalkylene;

$R^{129}$ is hydrogen, alkyl, alkenyl, alkynyl, aryl, heteroaryl, heteroarylium, cycloalkyl, heterocyclyl, $OR^{140}$ or $NR^{132}R^{133}$;

$R^{130}$ and $R^{131}$ are each independently hydrogen, alkyl, alkenyl, alkynyl, aryl, heteroaryl, heteroarylium, cycloalkyl, heterocyclyl or $C(A)R^{141}$, where $R^{141}$ is alkyl, alkenyl, alkynyl, aryl, heteroaryl, heteroarylium, cycloalkyl, heterocyclyl, $OR^{125}$ or $NR^{132}R^{133}$; or $R^{130}$ and $R^{131}$ together form alkylene, alkenylene, alkynylene, or heteroalkylene;

$R^{132}$ and $R^{133}$ are each independently hydrogen, alkyl, alkenyl, alkynyl, aryl, heteroaryl, heteroarylium, cycloalkyl, or heterocyclyl, or $R^{132}$ and $R^{133}$ together form alkylene, alkenylene, alkynylene, or heteroalkylene; and $R^3$ is hydrogen, alkyl, alkenyl, alkynyl, cycloalkyl, heterocyclyl, aryl or heteroaryl;

wherein Y, Z, $R^1$, $R^2$ and $R^3$ are each independently unsubstituted or substituted with one, two or three substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, hydroxycarbonylalkenyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, alkoxycarbonylalkoxy, aryloxycarbonyl, aryloxycarbonylalkyl, aralkoxycarbonyl, aralkoxycarbonylalkyl, aralkoxycarbonylalkoxy, arylcarbonylalkyl, aminocarbonyl, aminocarbonylalkyl, aminocarbonylalkoxy, alkylaminocarbonyl, alkylaminocarbonylalkyl, alkylaminocarbonylalkoxy, dialkylaminocarbonyl, dialkylaminocarbonylalkyl, dialkylaminocarbonylalkoxy, arylaminocarbonyl, arylaminocarbonylalkyl, arylaminocarbonylalkoxy, diarylaminocarbonyl, diarylaminocarbonyl alkoxy, arylalkylaminocarbonyl, arylalkylaminocarbonylalkyl, arylalkylaminocarbonylalkoxy, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $—N^+R^{151}R^{152}R^{153}$, $P(R^{150})_2$, $P(=O)(R^{150})_2$, $OP(=O)(R^{150})_2$, $—NR^{160}C(=O)R^{163}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; azido, tetrazolyl or two $Q^1$ groups, which substitute atoms in a 1,2 or 1,3 arrangement, together form alkylenedioxy (i.e., $—O—(CH_2)_y—O—$), thioalkylenoxy (i.e., $—S—(CH_2)_y—O—$) or alkylenedithioxy (i.e., $—S—(CH_2)_y—S—$) where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, hydroxycarbonylalkenyl alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, $-N^+R^{151}R^{152}R^{153}$, $P(R^{150})_2$, $P(=O)(R^{150})_2$, $OP(=O)(R^{150})_2$, $-NR^{160}C(=O)R^{163}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^2$ groups, which substitute atoms in a 1,2 or 1,3 arrangement, together form alkylenedioxy (i.e., $-O-(CH_2)_y-O-$), thioalkylenoxy (i.e., $-S-(CH_2)_y-O-$) or alkylenedithioxy (i.e., $-S-(CH_2)_y-S-$) where y is 1 or 2; or two $Q^2$ groups, which substitute the same atom, together form alkylene;

$R^{150}$ is hydroxy, alkoxy, aralkoxy, alkyl, heteroaryl, heterocyclyl, aryl or $-NR^{170}R^{171}$, where $R^{170}$ and $R^{171}$ are each independently hydrogen, alkyl, aralkyl, aryl, heteroaryl, heteroaralkyl or heterocyclyl, or $R^{170}$ and $R^{171}$ together form alkylene, azaalkylene, oxaalkylene or thiaalkylene;

$R^{151}$, $R^{152}$ and $R^{153}$ are each independently hydrogen, alkyl, aryl, aralkyl, heteroaryl, heteroaralkyl, heterocyclyl or heterocyclylalkyl;

$R^{160}$ is hydrogen, alkyl, aryl, aralkyl, heteroaryl, heteroaralkyl, heterocyclyl or heterocyclylalkyl; and $R^{163}$ is alkoxy, aralkoxy, alkyl, heteroaryl, heterocyclyl, aryl or $-NR^{170}R^{171}$.

14. A compound, or a pharmaceutically acceptable salt thereof, selected from the group consisting of:

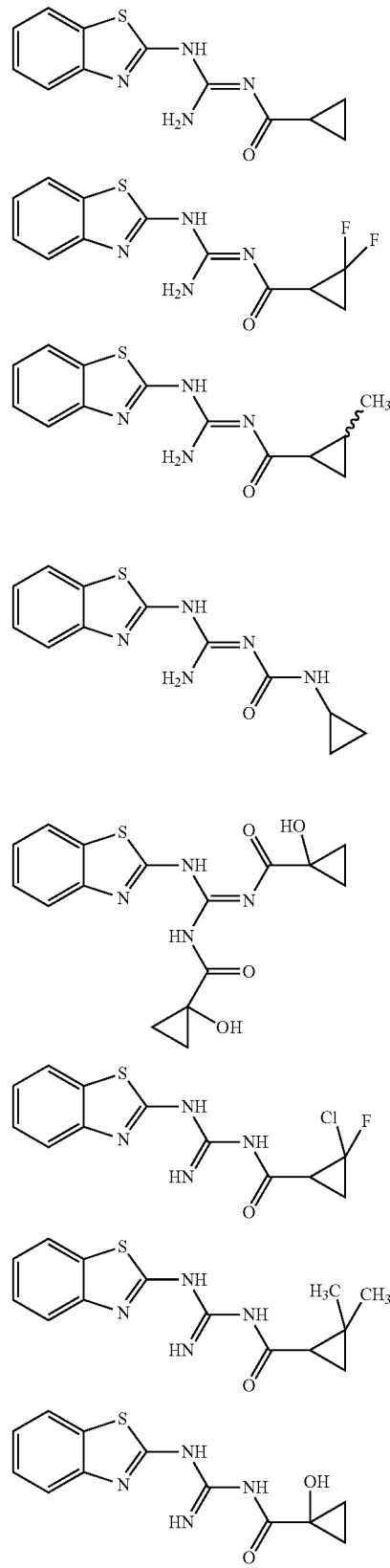

-continued

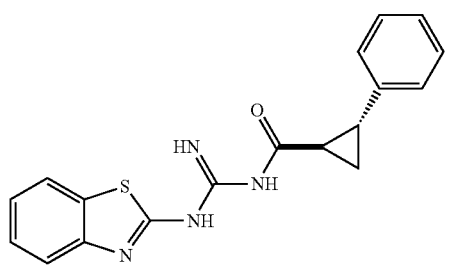

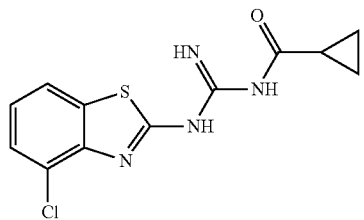

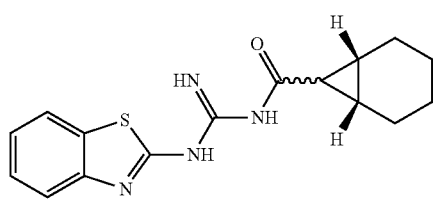

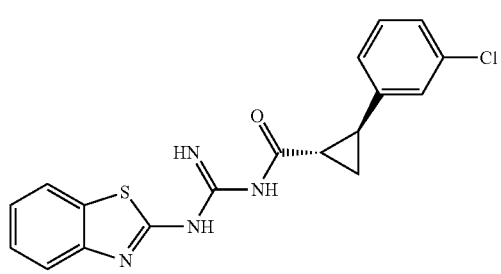

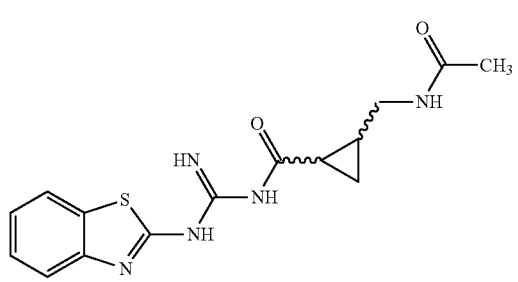

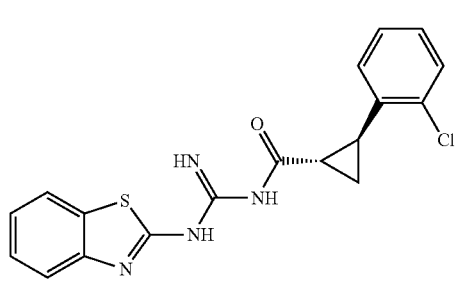

-continued

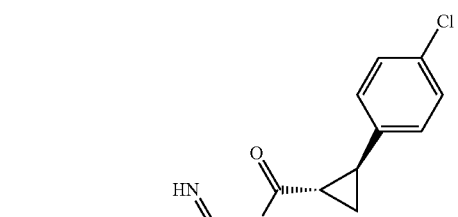

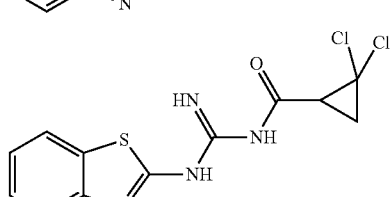

and

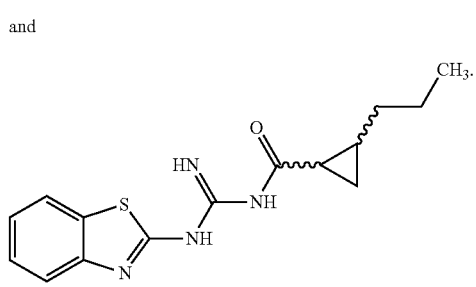

15. A composition, comprising a compound of the formula:

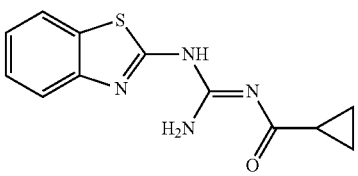 [SMILES: N/C(=N\C(=O)C1CC1)Nc1nc2ccccc2s1]

or a pharmaceutically acceptable salt thereof, and a pharmaceutically acceptable excipient.

16. A compound of the formula:

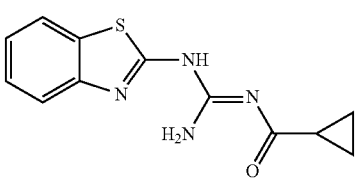 [SMILES: N/C(=N\C(=O)C1CC1)Nc1nc2ccccc2s1]

or a pharmaceutically acceptable salt thereof.

17. A method of inhibiting or preventing α-synuclein toxicity and/or fibril formation, inhibiting or preventing α-synuclein fibril growth, and/or causing disassembly, disruption, and/or disaggregation of α-synuclein fibrils and α-synuclein-associated protein deposits in a patient, comprising administering to the patient a compound:

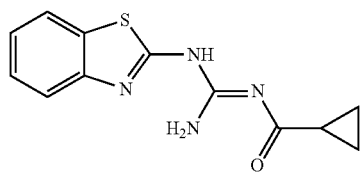 [SMILES: N/C(=N\C(=O)C1CC1)Nc1nc2ccccc2s1]
or a pharmaceutically acceptable salt thereof.
18. A method of treating or ameliorating a synucleinopathy comprising administering to a patient a compound:
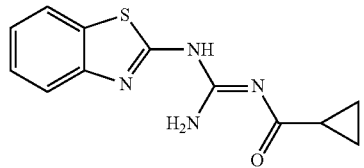 [SMILES: N/C(=N\C(=O)C1CC1)Nc1nc2ccccc2s1]
or a pharmaceutically acceptable salt thereof.
* * * * *